United States Patent
Jeong et al.

(10) Patent No.: US 10,236,452 B2
(45) Date of Patent: Mar. 19, 2019

(54) COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Eunjae Jeong, Yongin-si (KR); Youngkook Kim, Yongin-si (KR); Junha Park, Yongin-si (KR); Munki Sim, Yongin-si (KR); Eunyoung Lee, Yongin-si (KR); Hyoyoung Lee, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 154 days.

(21) Appl. No.: 15/085,763

(22) Filed: Mar. 30, 2016

(65) Prior Publication Data
US 2017/0040549 A1    Feb. 9, 2017

(30) Foreign Application Priority Data
Aug. 4, 2015 (KR) .................. 10-2015-0110237

(51) Int. Cl.
*H01L 27/32* (2006.01)
*H01L 51/00* (2006.01)
(Continued)

(52) U.S. Cl.
CPC ........ *H01L 51/0073* (2013.01); *C07D 307/77* (2013.01); *C07D 307/92* (2013.01);
(Continued)

(58) Field of Classification Search
CPC ............... H01L 51/006; H01L 51/0059; H01L 51/5056; H01L 51/0052; H01L 51/0058;
(Continued)

(56) References Cited

U.S. PATENT DOCUMENTS 5,645,948 A    7/1997   Shi et al.
6,465,115 B2   10/2002  Shi et al.
(Continued)

FOREIGN PATENT DOCUMENTS

CN    103396386 A    11/2013
EP    2 295 421 A1    3/2011
(Continued)

OTHER PUBLICATIONS

Adachi, Chihaya, et al., Confinement of charge carriers and molecular excitons within 5nmthick emitter layer in organic electroluminescent devices with a double heterostructure, *Applied Physics Letters*, 1990, pp. 531-533, vol. 57, AIP Publishing LLC.
(Continued)

*Primary Examiner* — Shane Fang
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including a compound represented by Formula 1. The organic light-emitting device including the compound of Formula 1 may have high efficiency, low driving voltage, high brightness, and long lifespan characteristics.

(Continued)

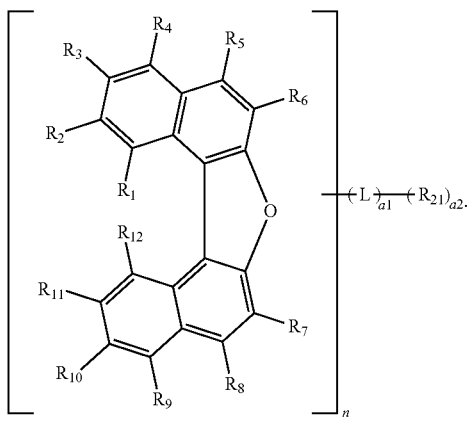

Formula 1

19 Claims, 1 Drawing Sheet

(51) Int. Cl.
*H01L 51/50* (2006.01)
*C07D 307/77* (2006.01)
*C07D 307/92* (2006.01)
*C07D 405/14* (2006.01)
*C07D 409/14* (2006.01)

(52) U.S. Cl.
CPC ......... *C07D 405/14* (2013.01); *C07D 409/14* (2013.01); *H01L 27/3244* (2013.01); *H01L 51/00* (2013.01); *H01L 51/0052* (2013.01); *H01L 51/0067* (2013.01); *H01L 51/0077* (2013.01); *H01L 51/5056* (2013.01); *H01L 51/5072* (2013.01); *H01L 2251/50* (2013.01)

(58) Field of Classification Search
CPC .. H01L 51/0012; C07C 211/54; C07C 211/58
See application file for complete search history.

(56) References Cited

U.S. PATENT DOCUMENTS

| 6,596,415 | B2 | 7/2003 | Shi et al. | |
|---|---|---|---|---|
| 2003/0165715 | A1 | 9/2003 | Yoon et al. | |
| 2010/0001636 | A1* | 1/2010 | Yabunouchi | C07D 307/91 313/504 |
| 2014/0034915 | A1 | 2/2014 | Lee et al. | |
| 2014/0124748 | A1* | 5/2014 | Kim | C07D 403/12 257/40 |
| 2014/0183500 | A1 | 7/2014 | Ikeda et al. | |
| 2015/0014673 | A1 | 1/2015 | Takeya et al. | |

FOREIGN PATENT DOCUMENTS

| JP | 10-17860 A | 1/1998 | |
|---|---|---|---|
| JP | 11-87067 A | 3/1999 | |
| KR | 10-0691543 B1 | 3/2007 | |
| KR | 10-2014-0017400 A | 2/2014 | |
| WO | WO 2013/125599 A1 | 8/2013 | |
| WO | WO 2014/104144 A1 | 7/2014 | |
| WO | WO 2016131918 | * 8/2016 | ........... C07D 401/04 |

OTHER PUBLICATIONS

Johansson, Nicklas, et al., Solid-State Amplified Spontaneous Emission in Some Spiro-Type Molecules: A New Concept for the Design of Solid-State Lasing Molecules, *Advanced Materials*, 1998, pp. 1136-1141, vol. 10, No. 14, Wiley-VCH Verlag GmbH, Weinheim, Germany.
Sakamoto, Youichi, et al., Synthesis, Characterization, and Electron-Transport Property of Perfluorinated Phenylene Dendrimers, *J. Am. Chem. Soc.*, 2000, pp. 1832-1833, vol. 122, American Chemical Society.
Tang, C. W., et al., Organic electroluminescent diodes, *Applied Physics Letters*, 1987, pp. 913-915, vol. 51, AIP Publishing LLC.
Tao, Y. T., et al., Sharp green electroluminescence from 1H-pyrazolo[3,4-b]quinoline-based light-emitting diodes, *Applied Physics Letters*, 2000, pp. 1575-1577, vol. 77, American Institute of Physics.
Yamaguchi, Shigehiro, et al., Diphenylamino-Substituted 2,5-Diarylsiloles for Single-Layer Organic Electroluminescent Devices, *Chemistry Letters*, 2001, pp. 98-99, The Chemical Society of Japan.
Nakanishi et al., "Oligonaphthofurans: Fan-Shaped and Three-Dimensional π-Compounds," Journal of the American Chemical Society, vol. 136, Apr. 2014, pp. 7101-7109.
EPO Search Report dated Jun. 30, 2016, for corresponding European Patent Application No. 16168481.6 (8 pages).

* cited by examiner

| 190 |
|---|
| 150 |
| 110 |

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0110237, filed on Aug. 4, 2015, in the Korean Intellectual Property Office, the disclosure of which is incorporated herein in its entirety by reference.

BACKGROUND

1. Field

One or more aspects of example embodiments of the present disclosure relate a compound and an organic light-emitting device including the same.

2. Description of the Related Art

Organic light-emitting devices (OLEDs) are self-emitting devices that have wide viewing angles, high contrast ratios, and short response times. OLEDs also exhibit excellent brightness, driving voltage, and response speed characteristics, and can produce multicolored images.

An OLED may include a first electrode disposed (e.g., positioned) on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are then recombined in the emission layer to produce excitons. These excitons change from an excited state to a ground state, thereby generating light.

SUMMARY

One or more aspects of example embodiments of the present disclosure are directed toward a compound for an electron transporting material. One or more aspects of example embodiments of the present disclosure are directed toward an electron transporting material and organic light-emitting device including the same.

Additional aspects will be set forth in part in the description which follows and, in part, will be apparent from the description, or may be learned by practice of the presented embodiments.

According to one or more example embodiments, there is provided a compound represented by Formula 1:

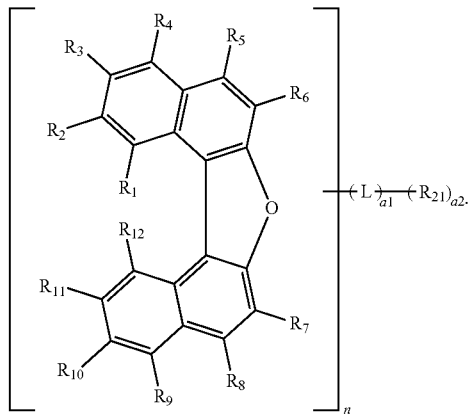

Formula 1

In Formula 1, $R_1$ to $R_{12}$ may each independently be selected from a bond, hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{21}$ may be selected from hydrogen, deuterium, a halogen, a cyano group, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n may be an integer selected from 2 to 4, a1 and a2 may each independently be an integer selected from 0 to 3, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, a substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$);

wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments, an organic light-emitting device includes: a first electrode; a second electrode facing the first electrode; and an organic layer between the first electrode and the second electrode, the organic layer including an emission layer, wherein the organic layer includes the compound represented by Formula 1.

According to one or more example embodiments, a display apparatus includes a thin film transistor, the thin film transistor including a source electrode and a drain electrode; and the organic light-emitting device, wherein the first electrode of the organic light-emitting device is electrically coupled to the source electrode or the drain electrode of the thin film transistor.

BRIEF DESCRIPTION OF THE DRAWING

These and/or other aspects will become apparent and more readily appreciated from the following description of the example embodiments, taken in conjunction with the accompanying drawing, which illustrates a schematic view of an organic light-emitting device according to an example embodiment.

DETAILED DESCRIPTION

Reference will now be made in more detail to example embodiments, examples of which are illustrated in the accompanying drawing, wherein like reference numerals refer to like elements throughout. In this regard, the present example embodiments may have different forms and should not be construed as being limited to the descriptions set forth herein. Accordingly, the example embodiments are merely described below, by referring to the drawing, to explain aspects of the present description. As used herein, the term "and/or" includes any and all combinations of one or more of the associated listed items. Expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

According to one or more embodiments of the present disclosure, there is provided a compound represented by Formula 1:

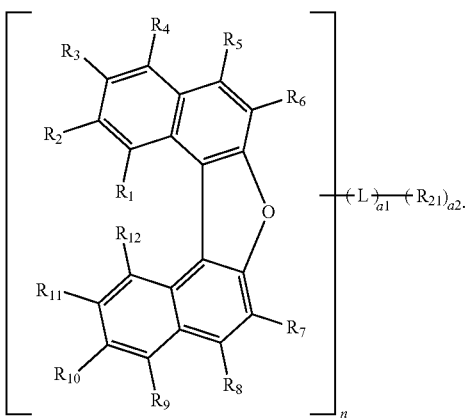

Formula 1

In Formula 1, $R_1$ to $R_{12}$ may each independently be selected from a bond (e.g., a single bond), hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{21}$ may be selected from hydrogen, deuterium, a halogen, a cyano group, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n may be an integer selected from 2 to 4, a1 and a2 may each independently be an integer selected from 0 to 3, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. When $R_1$ to $R_{12}$ are each independently a bond, L and/or $R_{21}$ in Formula 1 may be bonded (e.g., coupled) to a dinaphthofuran moiety at the position of the respective $R_1$ to $R_{12}$.

As electron transporting materials in organic light-emitting devices, organic metal complexes, that are unimolecular materials and have relatively good stability and movement speed of electrons, may be used.

For example, $Alq_3$ (having good stability and high affinity for electrons) has often been utilized as the organic unimolecular material. However, if $Alq_3$ is used in a blue light-emitting device, light emission may occur along with exciton diffusion, and thus color purity of the light-emitting device may be reduced.

Additional organic metal complexes may include flavone derivatives, germanium derivatives, and silicon chloropentadiene derivative. Non-limiting examples of the organic metal complexes include a 2-biphenyl-4-yl-5-(4-t-butylphenyl)-1,3,4-oxadiazole derivative (PBD) bonded to a spiro compound, and a 2,2',2"-(benzene-1,3,5-triyl)-tris(1-phenyl-1H-benzimidazole) derivative (TPBI), which has both hole blocking capability and excellent electron transporting characteristics.

For example, a benzoimidazole derivative has been recognized as a material having excellent durability. However, if the benzoimidazole derivative is used for an electron transport layer, the organic light-emitting device including the electron transport layer may have a short lifespan, poor preserving durability, and low reliability.

Some of the above-described shortcomings may be caused by physical and/or chemical changes in organic materials, photochecmial and/or electrochemical changes in organic materials, oxidation of a cathode, exfoliation, and/or a lack of durability.

One or more embodiments of the present inventive concept provide a novel heterocyclic compound represented by Formula 1, and an organic light-emitting device including an organic layer, wherein the organic layer includes the heterocyclic compound.

A related dinaphthofuran compound including only one dinaphthofuran moiety may be utilized as a material for forming an emission layer of an organic light-emitting device, or may be used in an organic semiconductor.

The compound of Formula 1 according to an example embodiment may include two or three dinaphthofuran moieties and various substituents and may have improved electron transporting capability. In this regard, an electron transport layer including the compound of Formula 1 may exhibit high efficiency and long lifespan characteristics.

Substituents of the compound of Formula 1 will be described hereinafter in more detail.

According to an example embodiment, in Formula 1, $R_1$ to $R_5$ and $R_7$ to $R_{12}$ may each independently be hydrogen or deuterium, and $R_6$ in Formula 1 may be a bond. In some embodiments, $R_1$ to $R_6$ and $R_8$ to $R_{12}$ may each independently be hydrogen or deuterium, and $R_7$ may be a bond.

According to an example embodiment, in Formula 1, $R_1$ to $R_4$ and $R_6$ to $R_{12}$ may each independently be hydrogen or deuterium, and $R_5$ may be a bond. In some embodiments, $R_1$ to $R_7$ and $R_9$ to $R_{12}$ may each independently be hydrogen or deuterium, and $R_8$ may be a bond.

When $R_5$ to $R_8$ are each independently a bond, L and/or $R_{21}$ in Formula 1 may be bonded (e.g., coupled) to a dinaphthofuran moiety of Formula 1 at the position of the respective $R_5$ to $R_8$.

According to an example embodiment, in Formula 1, L may be a substituted or unsubstituted $C_6$-$C_{60}$ arylene group or a substituted or unsubstituted $C_1$-$C_{60}$ heteroarylene group.

According to an example embodiment, in Formula 1, L may be a compound represented by one of the following Formulae 2a to 2c. For example, L may be a divalent or trivalent linking group. For example, in compounds represented by Formulae 2a to 2c, two or three hydrogens may be substituted:

2a

2b

2c

According to an example embodiment, in Formula 1, $R_{21}$ may be selected from a halogen, a cyano group, and a compound represented by one of Formulae 3a to 3h:

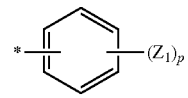

3a

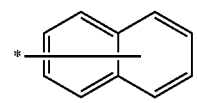

3b

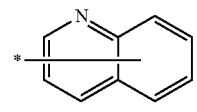

3c

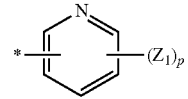

3d

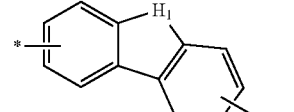

3e

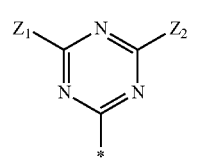

3f

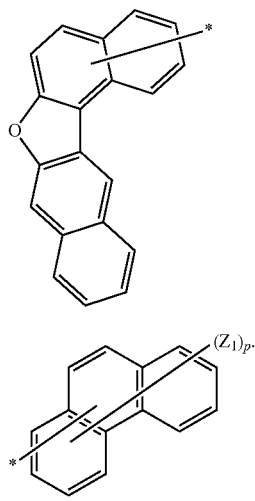

In Formulae 3a to 3h, $H_1$ may be selected from $NR_{31}$, $CR_{32}R_{33}$, O, and S, $R_{31}$ to $R_{33}$, $Z_1$ and $Z_2$ may each independently be selected from hydrogen, deuterium, a cyano group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p in Formula 3a may be an integer selected from 1 to 5, p in Formulae 3d and 3e may be an integer selected from 1 to 4, and p in Formula 3h may be an integer selected from 1 to 9, and

* may indicate a binding site.

According to an example embodiment, in Formula 1, n may be 2 or 3.

According to an example embodiment, the compound of Formula 1 may be represented by Formula 2:

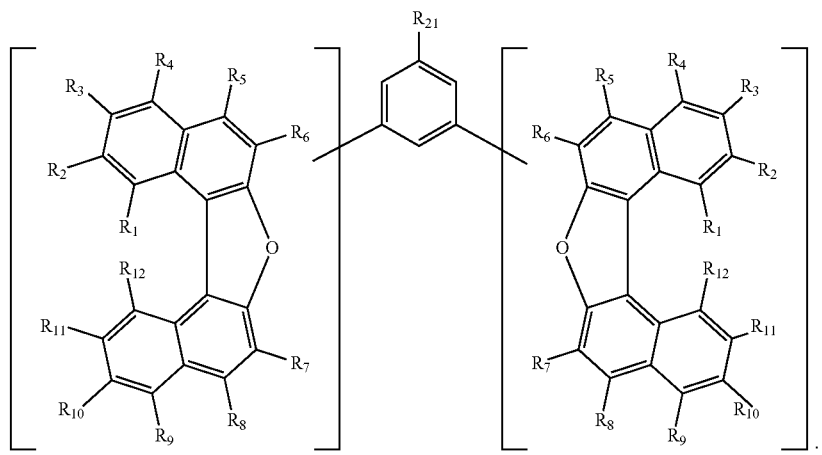

Formula 2

According to an example embodiment, the compound of Formula 1 may be represented by Formula 3:

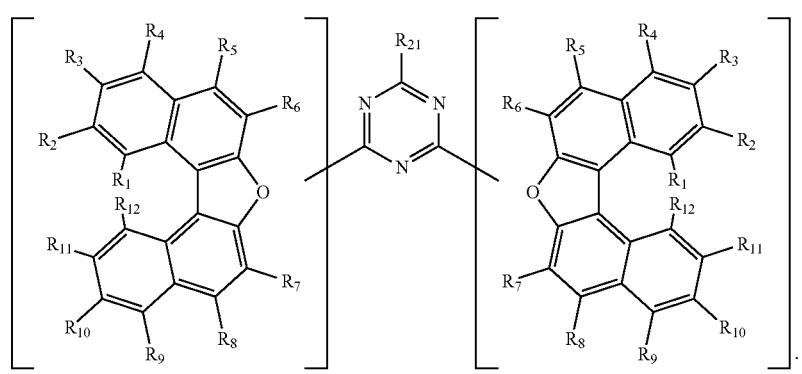

Formula 3

According to an example embodiment, the compound of Formula 1 may be represented by Formula 4:

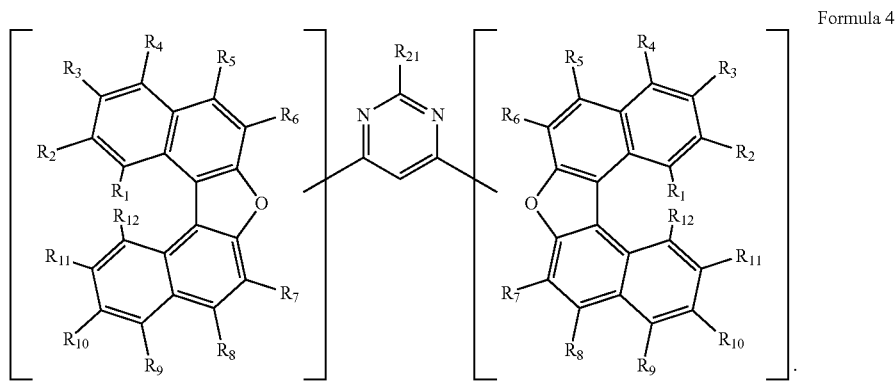

Formula 4

According to an example embodiment, the compound of Formula 1 may be represented by Formula 5:

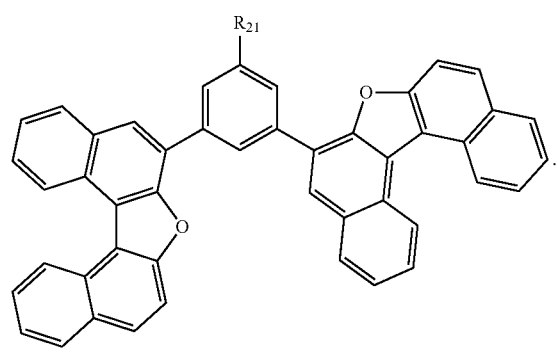

Formula 5

According to an example embodiment, the compound of Formula 1 may be represented by Formula 6:

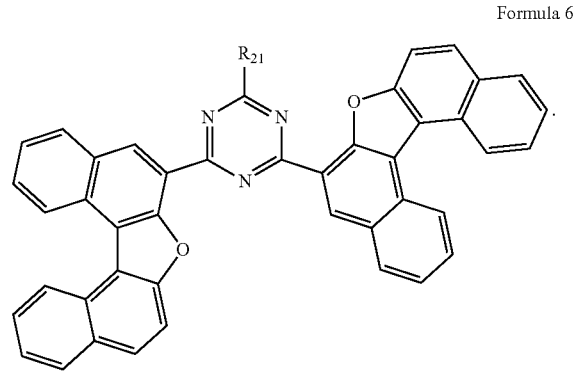

Formula 6

According to an example embodiment, the compound of Formula 1 may be represented by Formula 7:

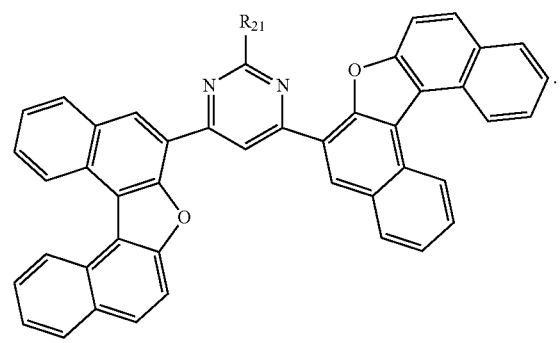

Formula 7

Descriptions of substituents of Formulae 2 to 7 may be inferred based on the descriptions provided above.

According to an example embodiment, the compound of Formula 1 may be one of Compounds 1 to 70:

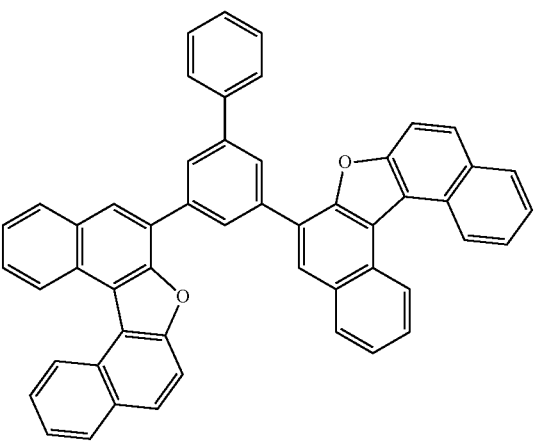

1

2
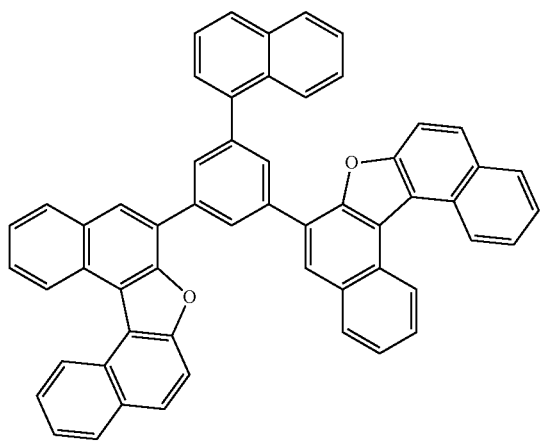
3
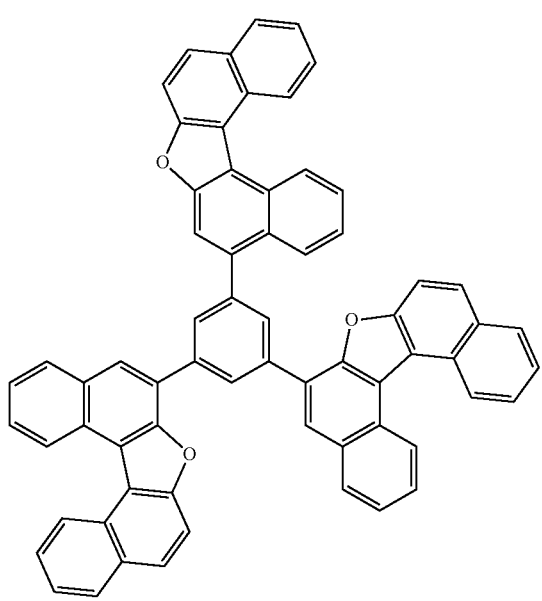
4
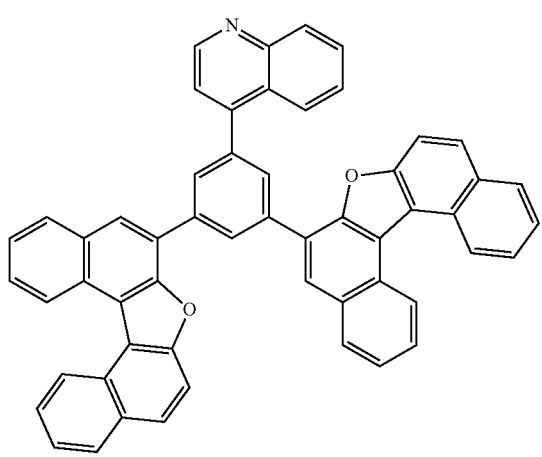
5
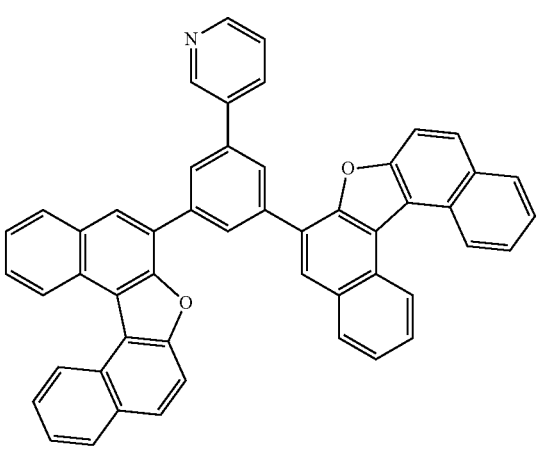
6
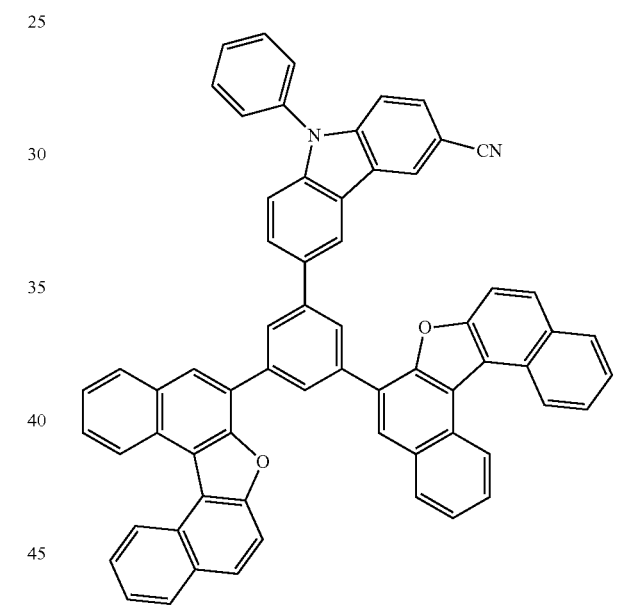
7
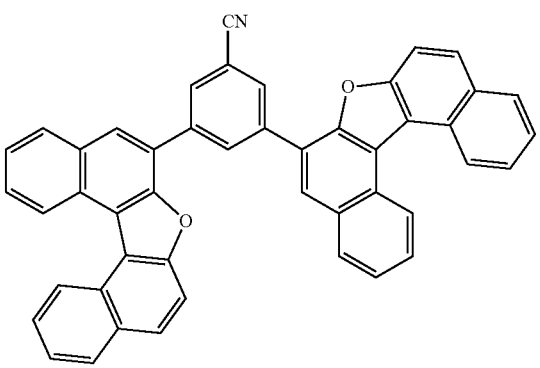

8
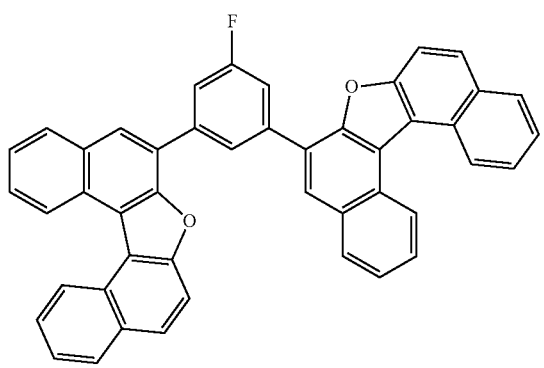
9
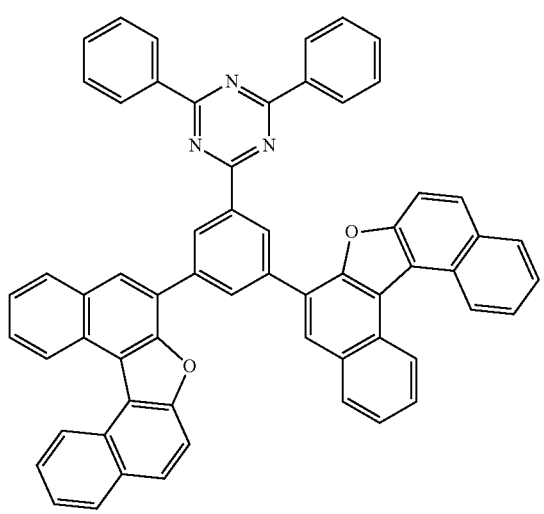
10
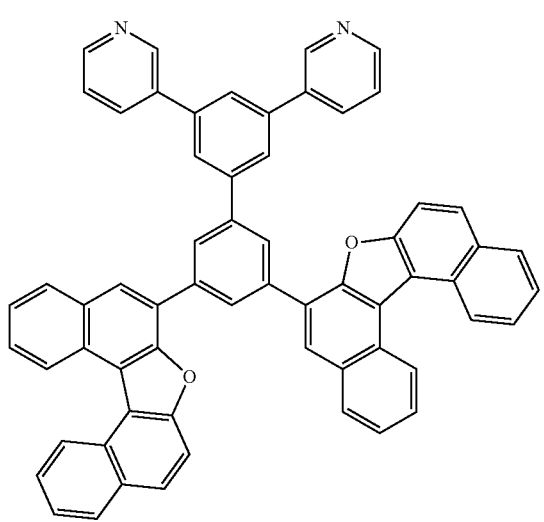
11
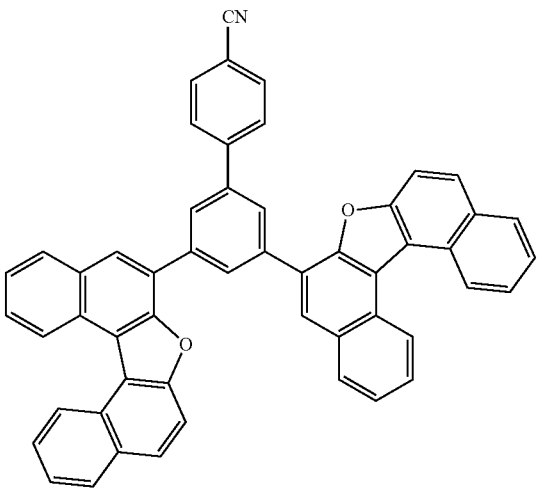
12
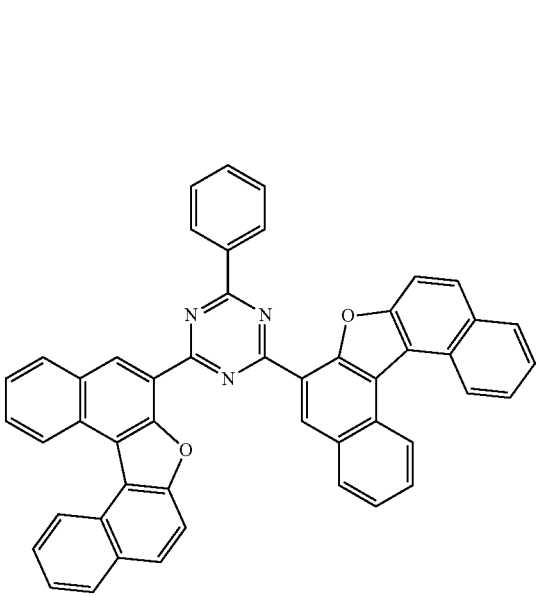
13
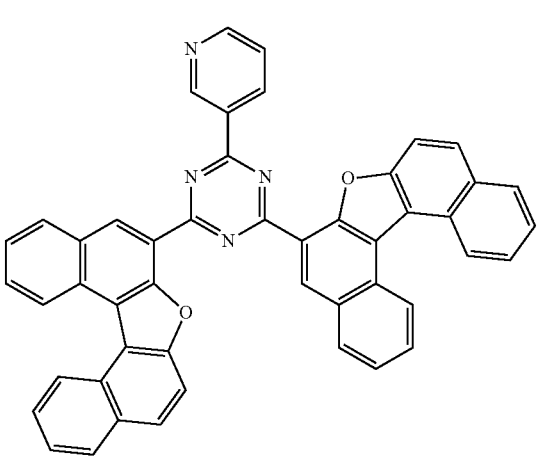

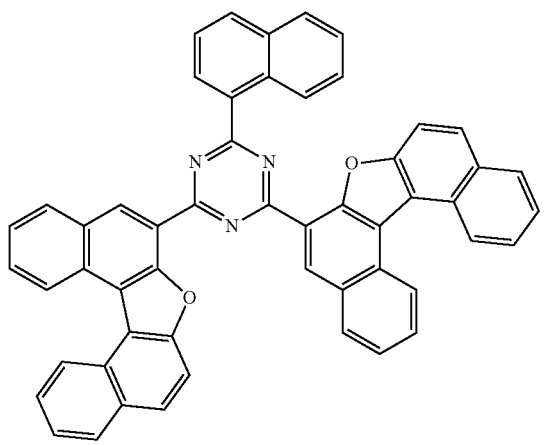
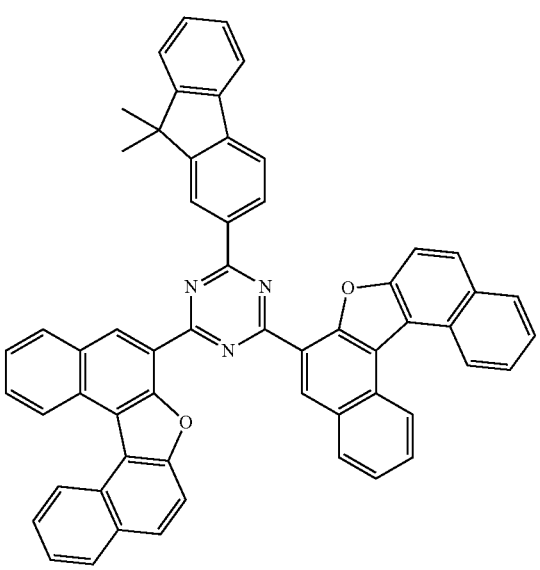
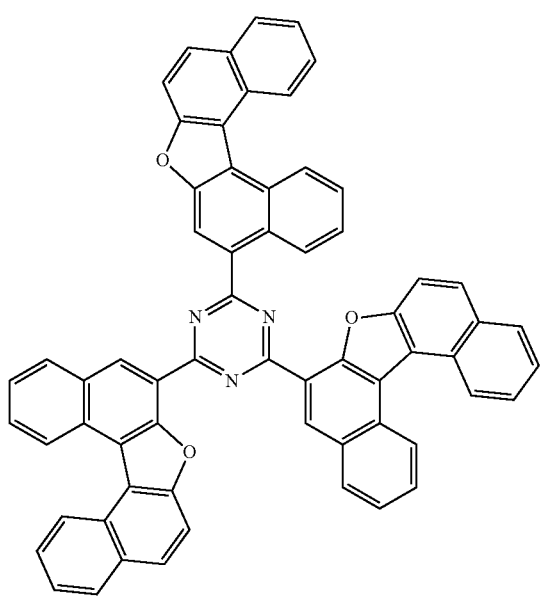
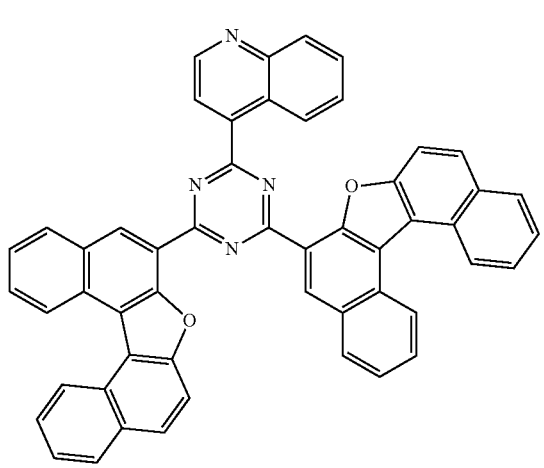
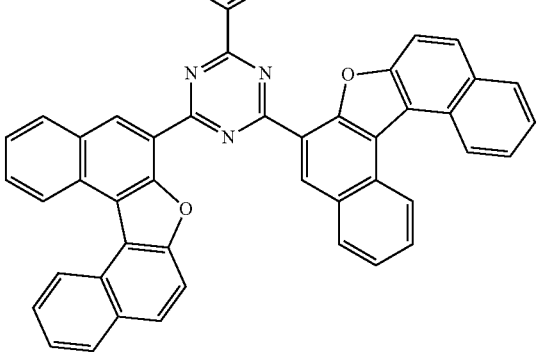

19
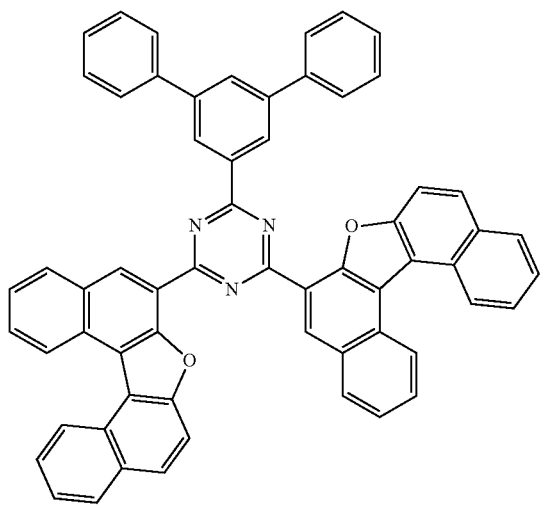
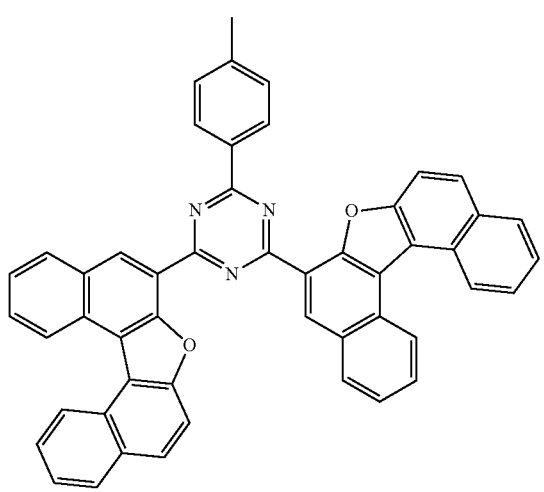
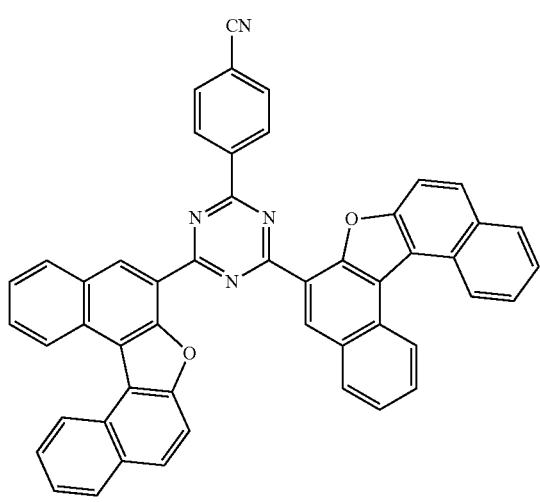
20
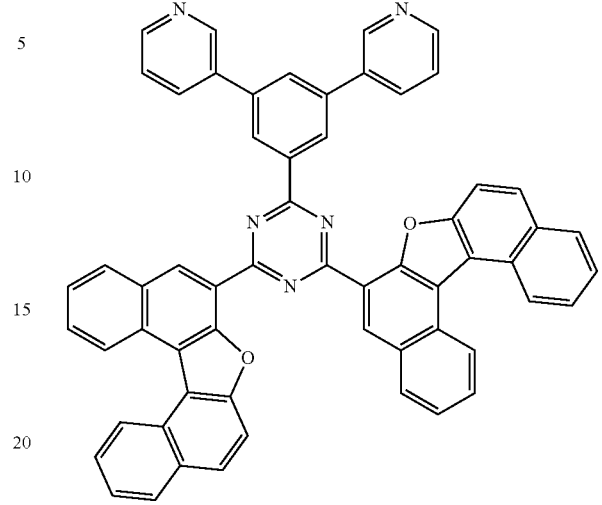
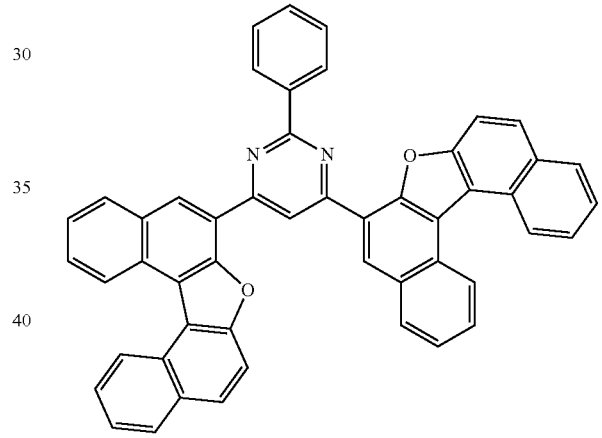
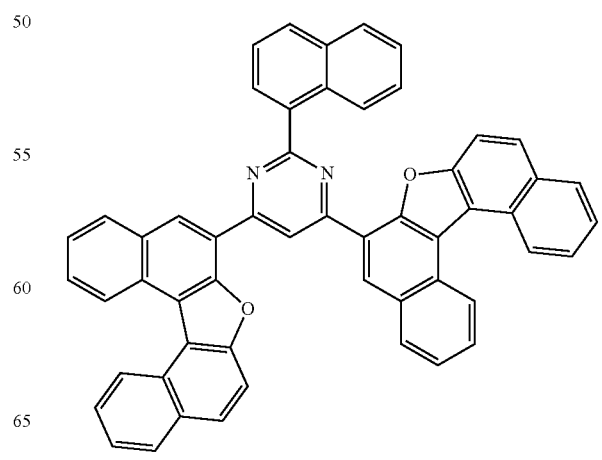

25
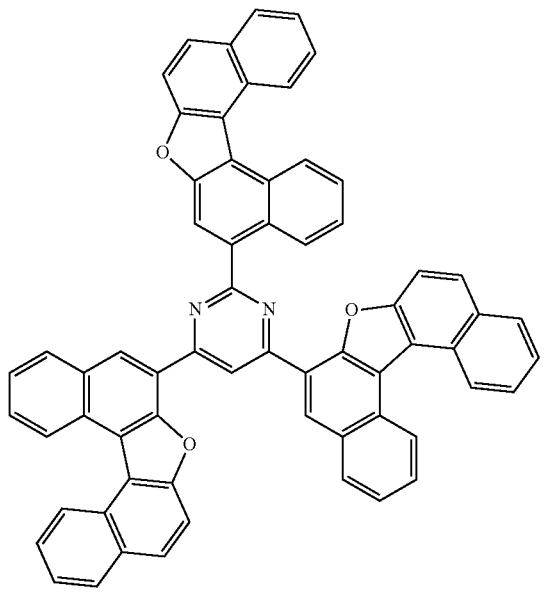
26
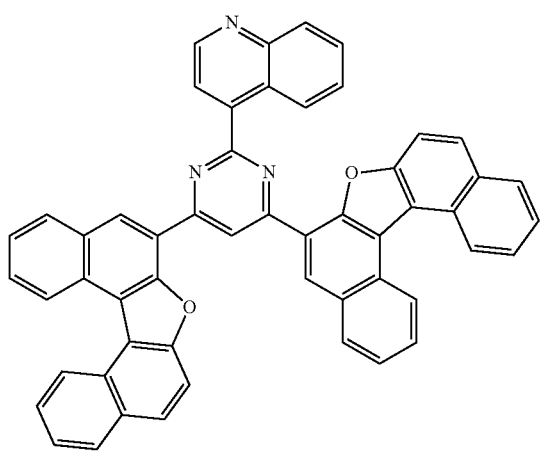
28
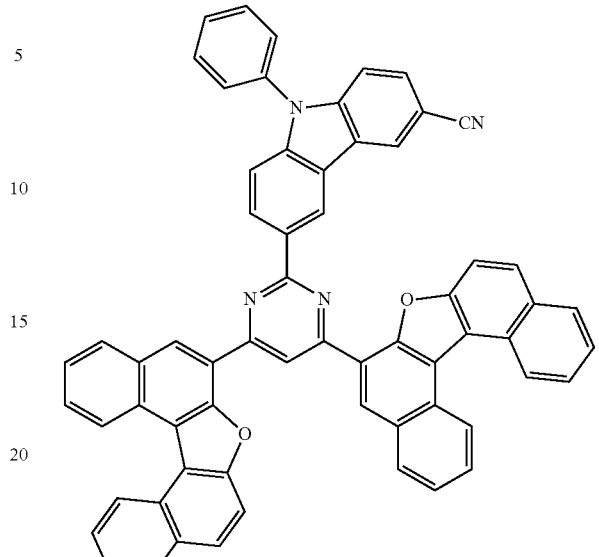
29
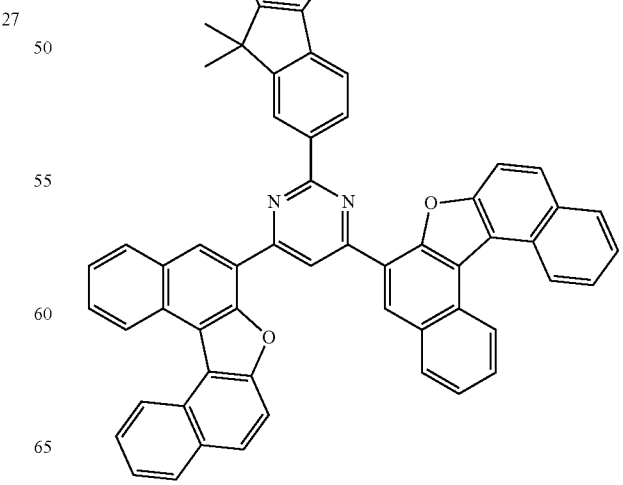

30
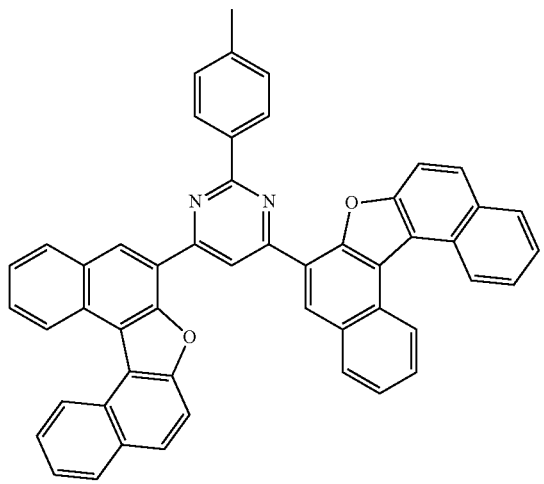
31
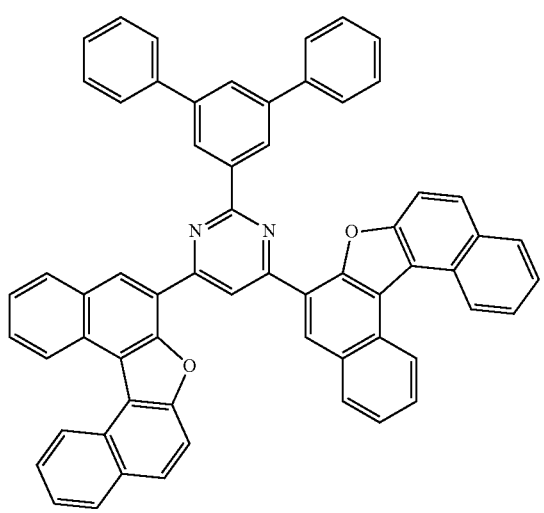
32
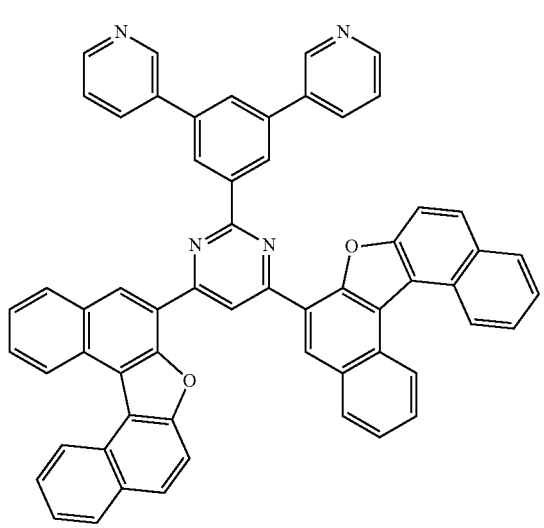
33
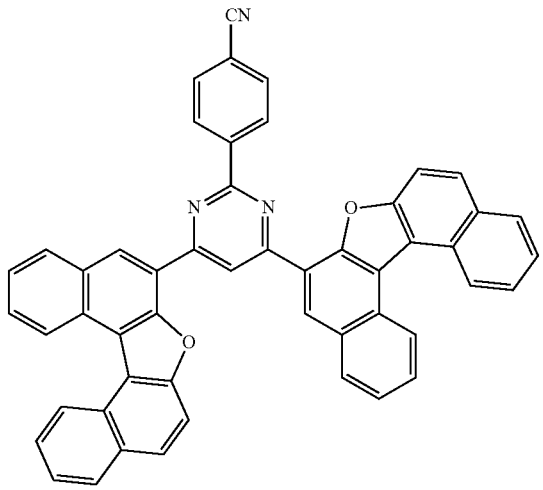
34
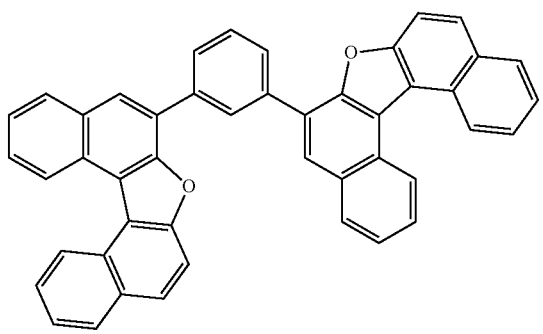
35
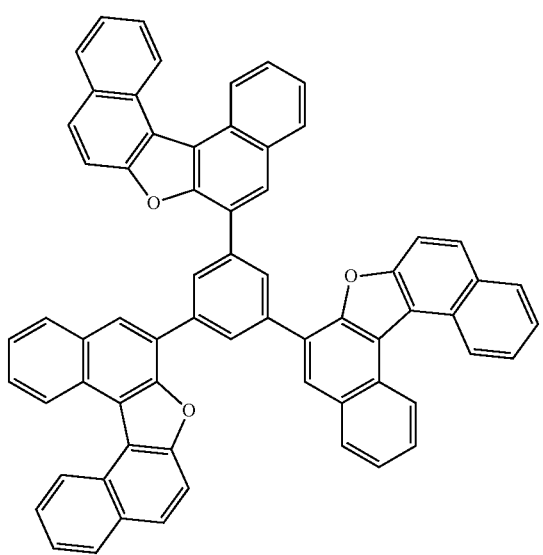

36
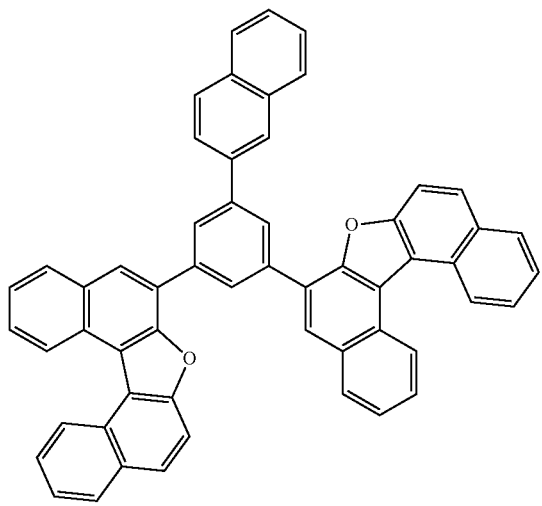
37
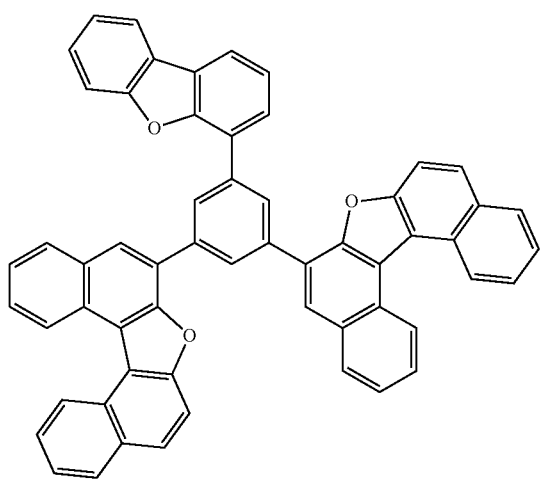
38
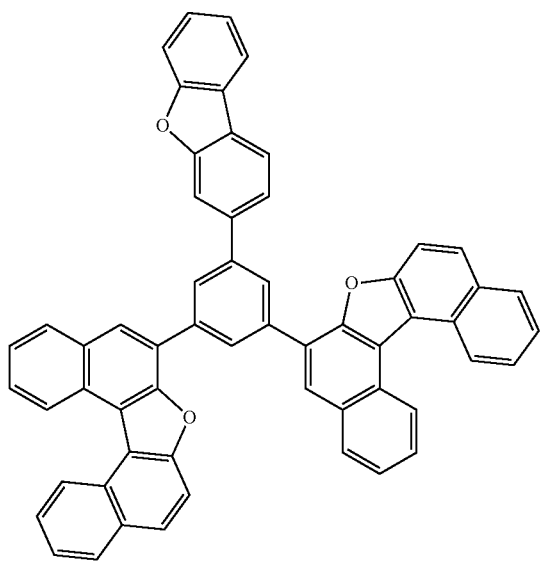
39
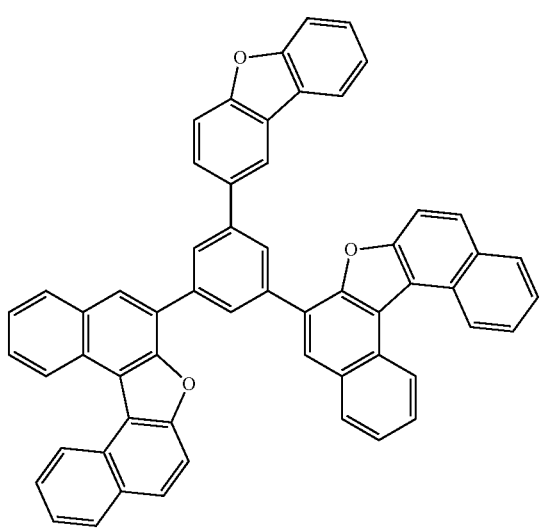
40
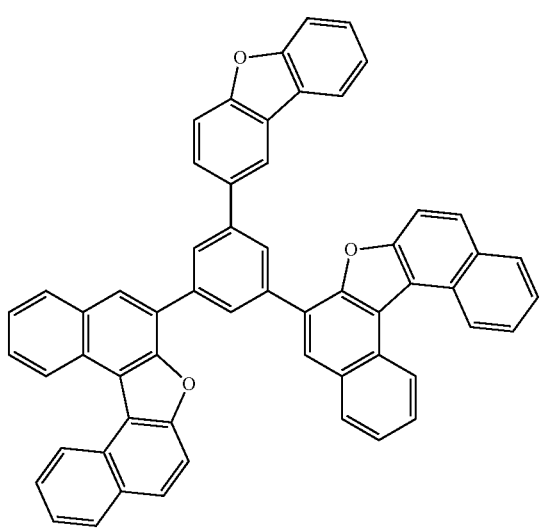
41
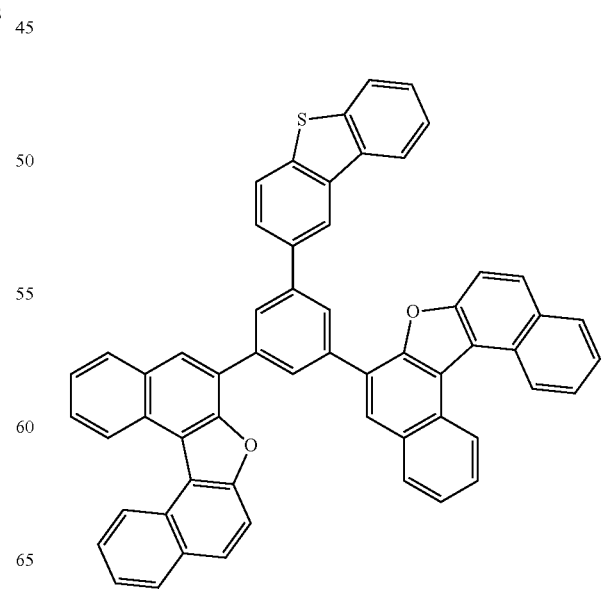

42
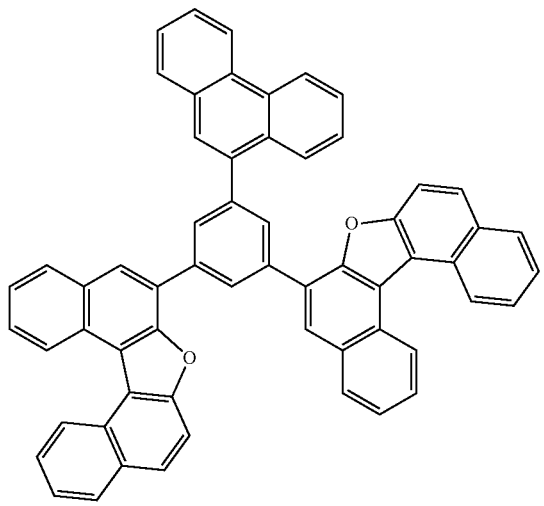
43
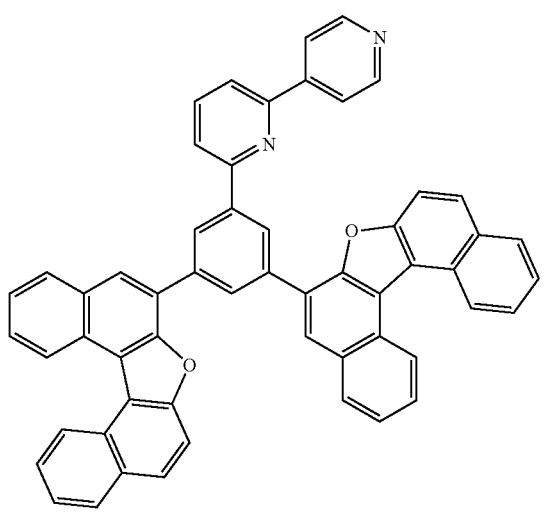
44
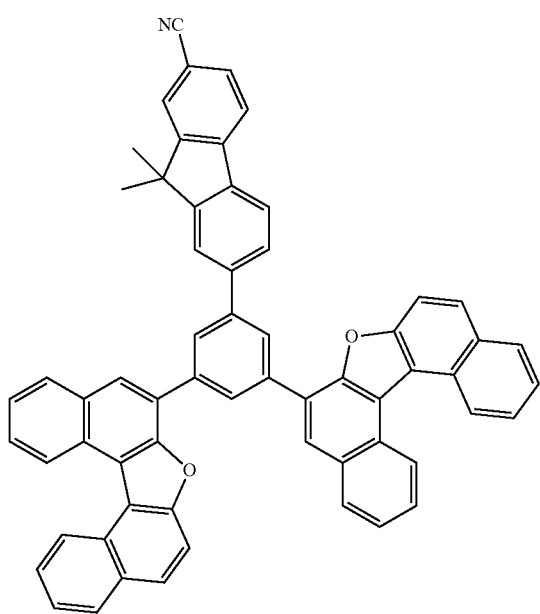
45
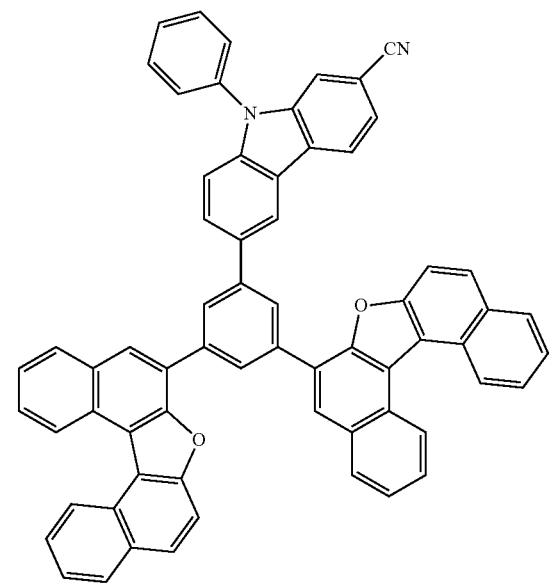
46
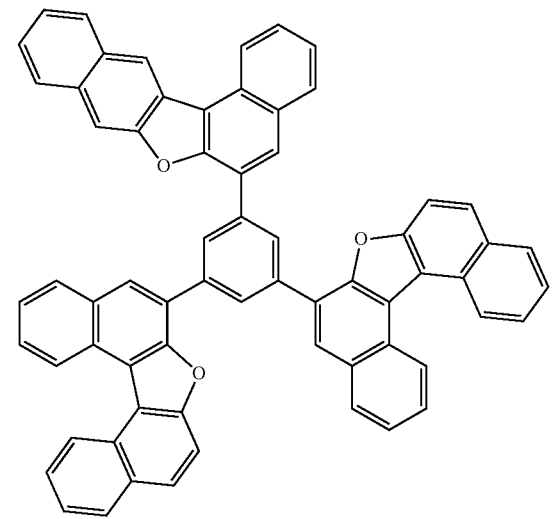

47
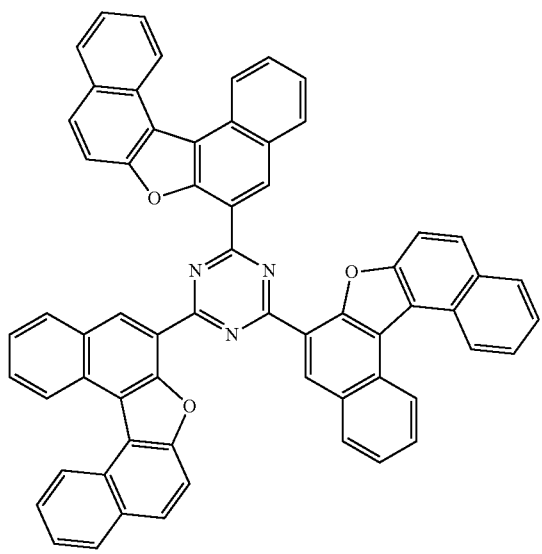
48
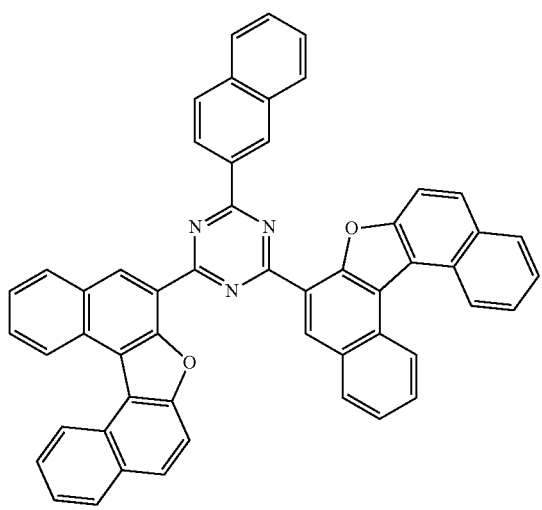
49
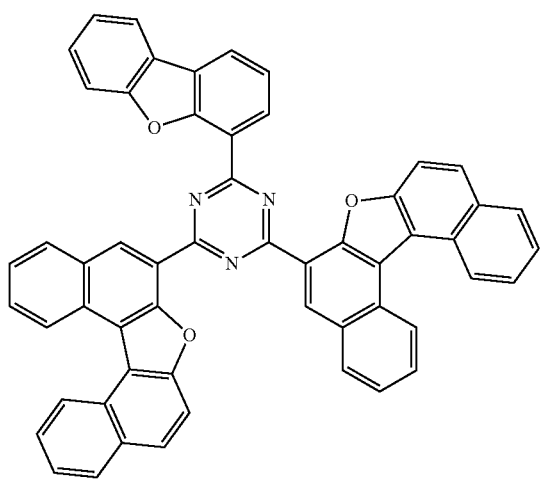
50
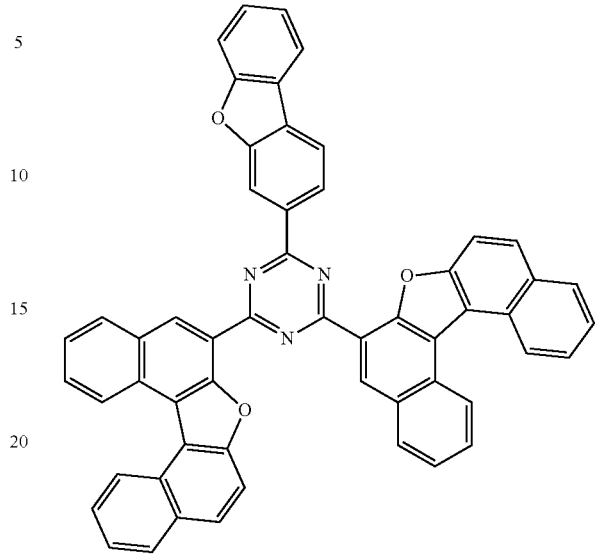
51
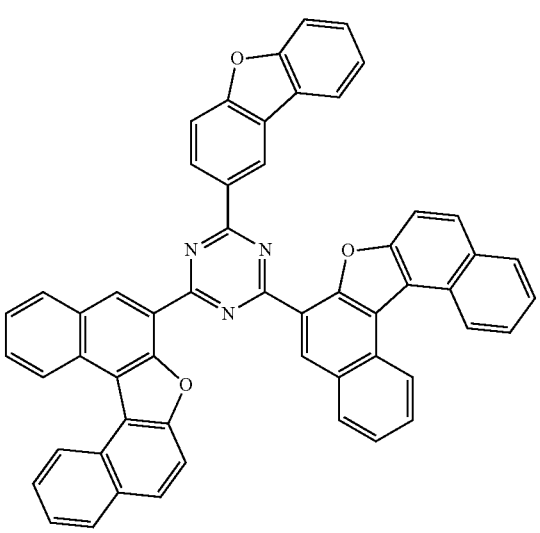
52
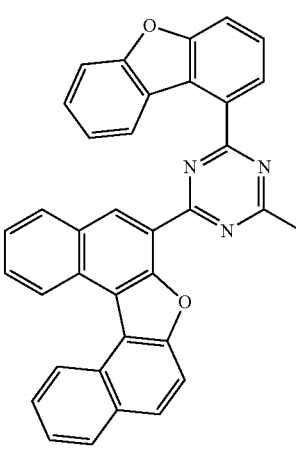

31
-continued
53
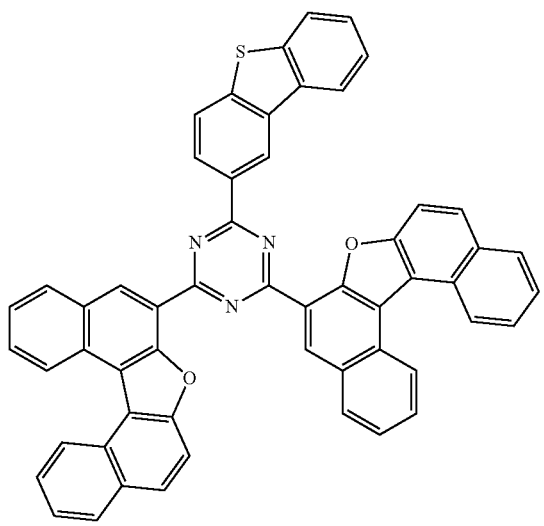
54
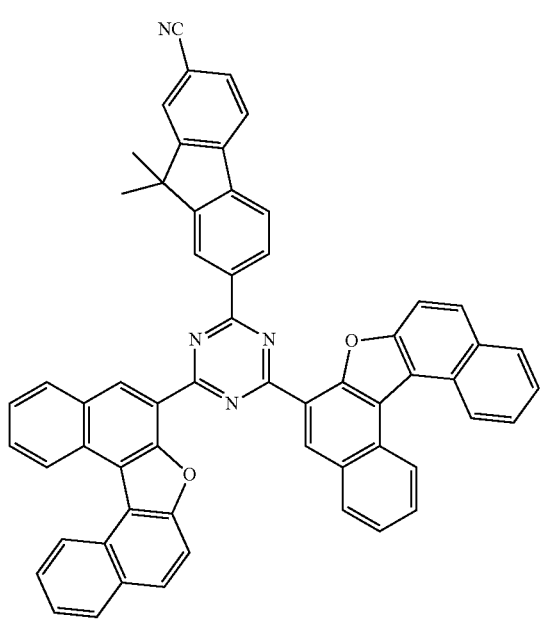
32
-continued
55
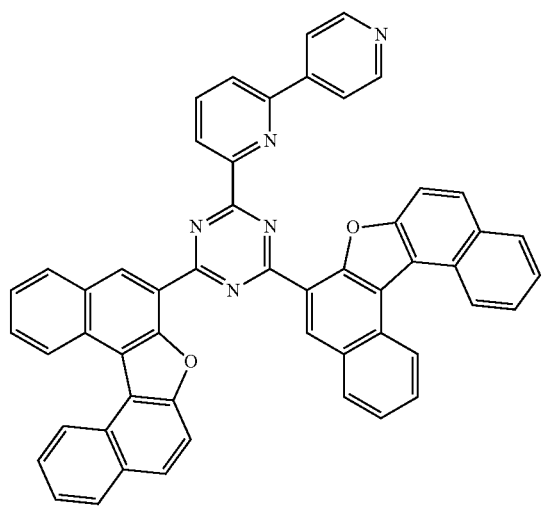
56
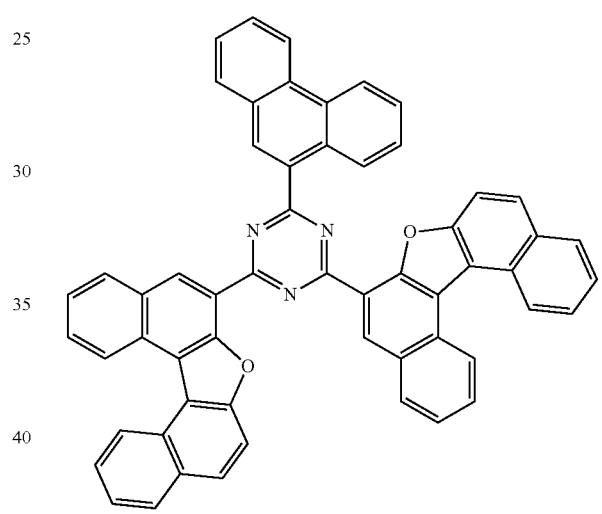
57
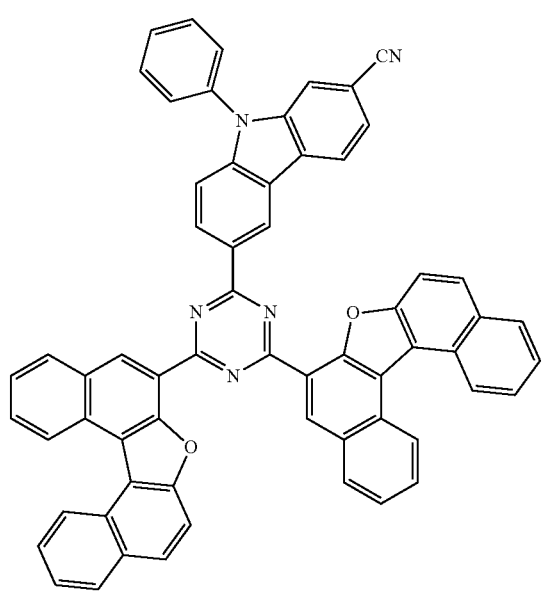

58
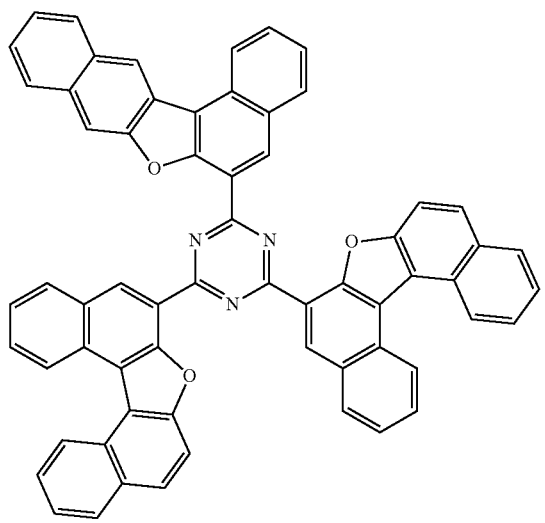
59
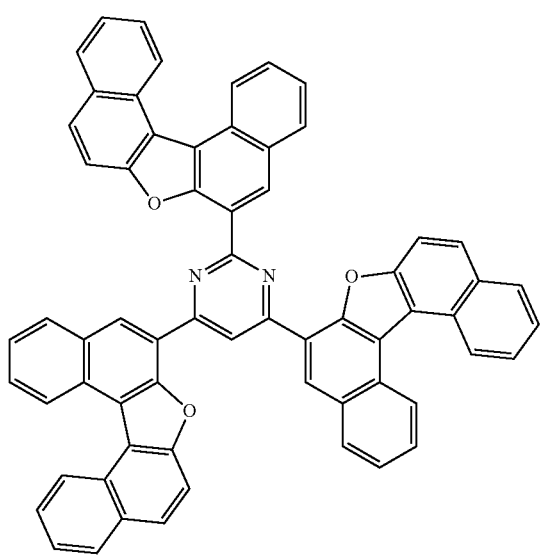
60
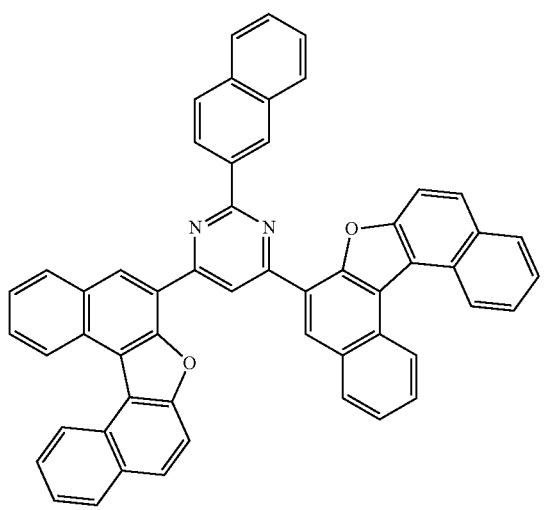
61
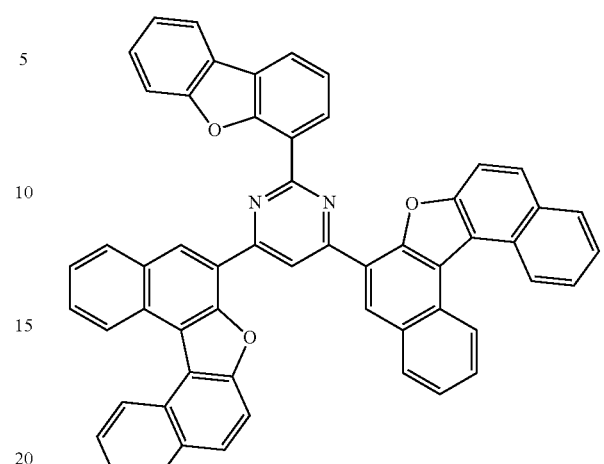
62
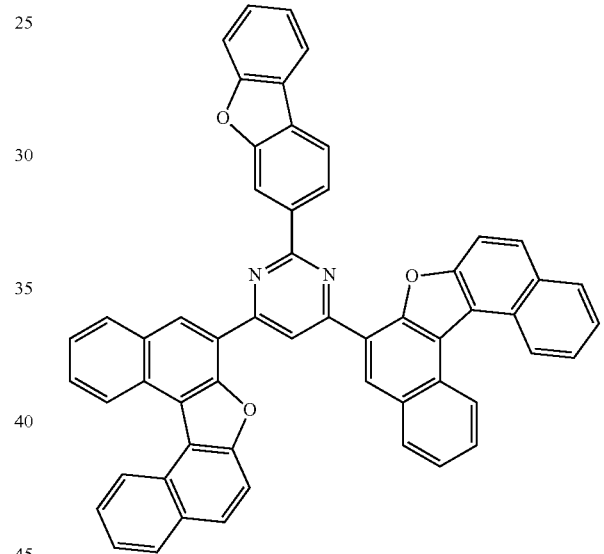
63
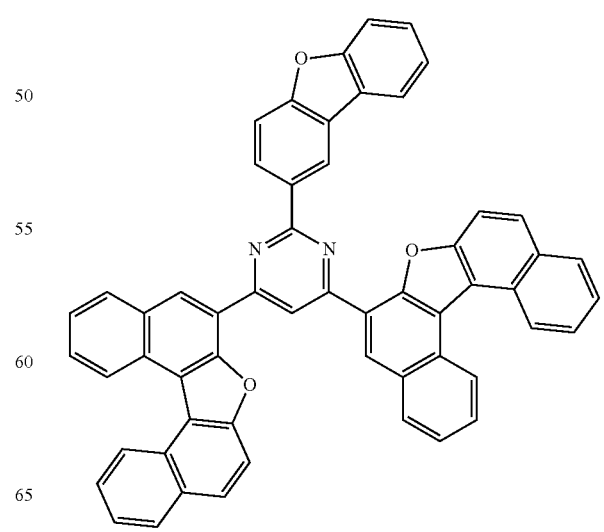

64
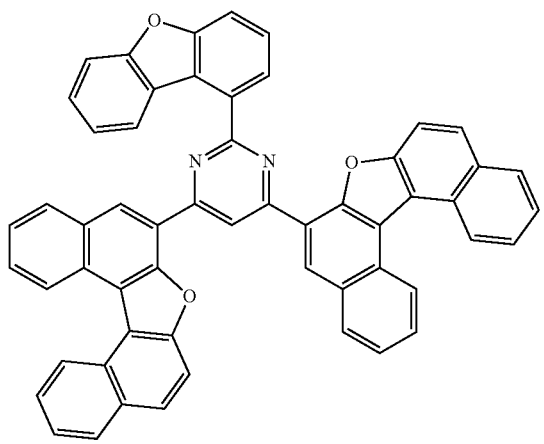
65
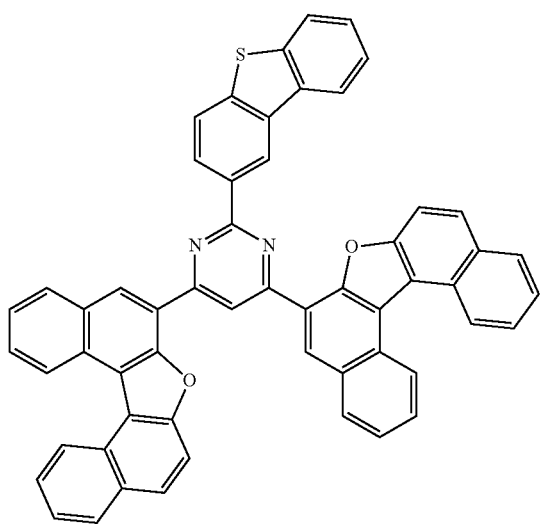
66
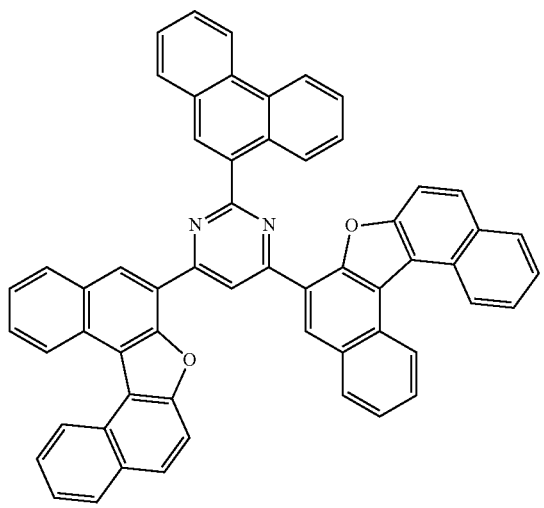
67
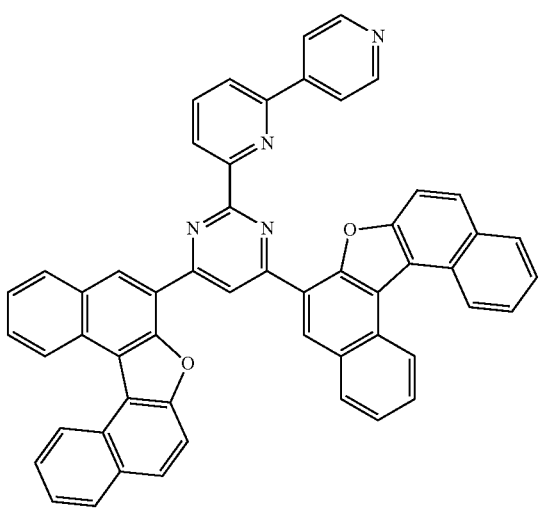
68
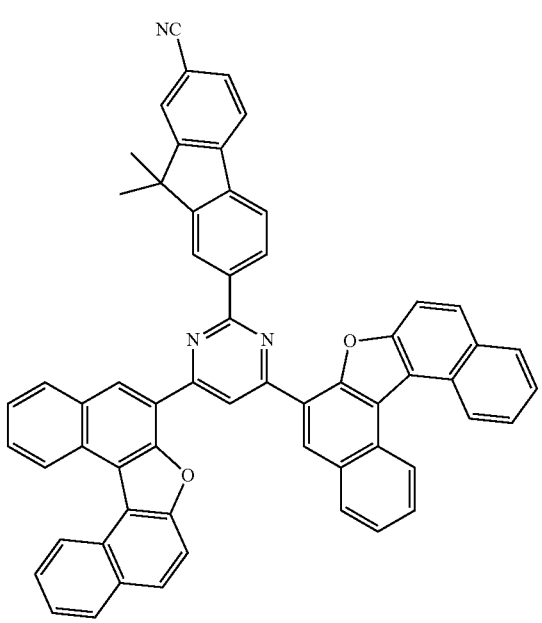

69

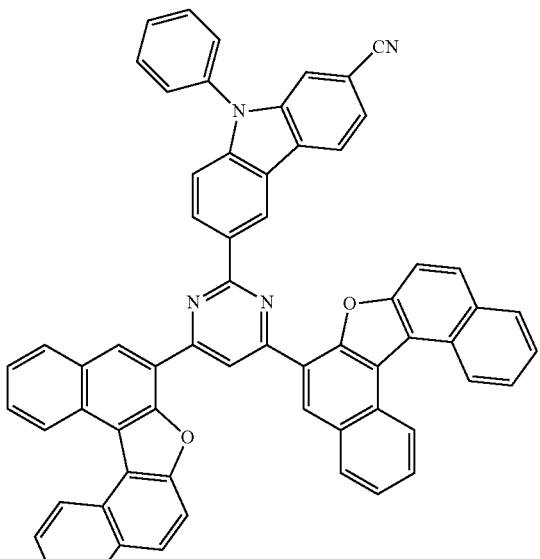

70

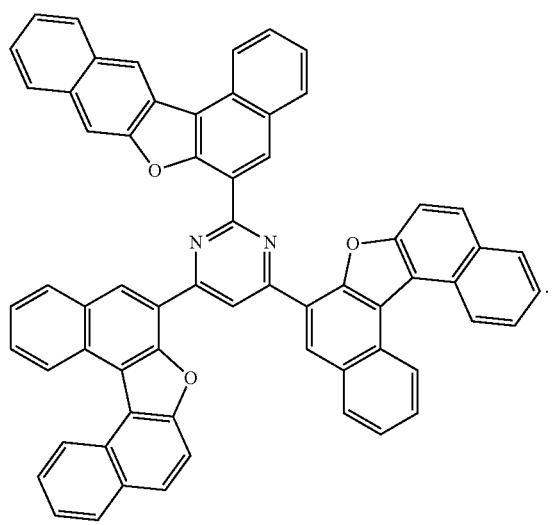

As used herein, the term "organic layer" may refer to a single layer and/or a plurality of layers disposed (e.g., positioned) between the first electrode and the second electrode in the organic light-emitting device. A material included in the "organic layer" is not limited to an organic material.

The drawing illustrates a schematic view of an organic light-emitting device 10 according to an example embodiment. The organic light-emitting device 10 may include a first electrode 110, an organic layer 150, and a second electrode 190.

Hereinafter, a structure of an organic light-emitting device according to an example embodiment and a method of manufacturing an organic light-emitting device according to an example embodiment will be described in connection with the drawing.

In some embodiments, a substrate may be additionally disposed (e.g., positioned) under the first electrode 110 or on the second electrode 190 in the organic light-emitting device 10 of the drawing. The substrate may be a glass substrate or a transparent plastic substrate, each with excellent mechanical strength, thermal stability, transparency, surface smoothness, ease of handling, and/or water resistance.

The first electrode 110 may be formed by, for example, depositing and/or sputtering a material for forming the first electrode 110 on the substrate. When the first electrode 110 is an anode, the material for forming the first electrode 110 may be selected from materials having a high work function, so as to facilitate hole injection. The first electrode 110 may be a reflective electrode, a semi-transmissive electrode, or a transmissive electrode. The material for forming the first electrode 110 may include indium tin oxide (ITO), indium zinc oxide (IZO), tin oxide ($SnO_2$), and/or zinc oxide (ZnO), each having transparency and excellent conductivity. In some embodiments, when the first electrode 110 is a semi-transmissive electrode or a reflective electrode, the material for forming the first electrode 110 may include at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including two or more layers. For example, the first electrode 110 may have a triple-layer structure of ITO/Ag/ITO, but the structure of the first electrode 110 is not limited thereto.

The organic layer 150 may be disposed (e.g., positioned) on the first electrode 110. The organic layer 150 includes an emission layer.

The organic layer 150 may further include a hole transport region between the first electrode 110 and the emission layer. The organic layer 150 may also include an electron transport region between the emission layer and the second electrode 190.

The hole transport region may include at least one selected from a hole injection layer (HIL), a hole transport layer (HTL), a buffer layer, and an electron blocking layer (EBL). The electron transport region may include at least one selected from a hole blocking layer (HBL), an electron transport layer (ETL), and an electron injection layer (EIL), but the hole transport region and the electron transport region are not limited thereto.

The hole transport region may have a single-layer structure formed of a single material, a single-layer structure formed of a plurality of different materials, or a multi-layer structure having a plurality of layers formed of a plurality of different materials.

For example, the hole transport region may have a single-layer structure formed of a plurality of different materials, or a structure of HIL/HTL, a structure of HIL/HTL/buffer layer, a structure of HIL/buffer layer, a structure of HTL/buffer layer, or a structure of HIL/HTL/EBL, wherein the layers of each of the structures are sequentially stacked from the first electrode 110 in this stated order, but the hole transport region is not limited thereto.

When the hole transport region includes an HIL, the HIL may be formed on the first electrode 110 by using one or more suitable methods, such as vacuum deposition, spin coating, casting, a Langmuir-Blodgett (LB) method, ink-jet printing, laser-printing, and/or laser-induced thermal imaging (LITI).

When the HIL is formed by vacuum deposition, the vacuum deposition may be performed at a deposition temperature in a range of about 100° C. to about 500° C., at a vacuum degree in a range of about $10^{-8}$ torr to about $10^{-3}$ torr, and at a deposition rate in a range of about 0.01 Å/sec to about 100 Å/sec, in consideration of a composition of the compound for forming the HIL and the structure of the suitable or desired HIL.

When the HIL is formed by spin coating, the spin coating may be performed at a coating rate in a range of about 2,000 rpm to about 5,000 rpm, and at a temperature in a range of about 80° C. to about 200° C., in consideration of a composition of the compound for forming the HIL and the structure of the suitable or desired HIL.

When the hole transport region includes an HTL, the HTL may be formed on the first electrode 110 or on the HIL by using one or more suitable methods, such as vacuum deposition, spin coating, casting, a LB method, ink-jet printing, laser-printing, and/or LITI. When the HTL is formed by vacuum deposition and/or by spin coating, the deposition conditions and/or the coating conditions may be inferred based on the deposition conditions and/or the coating conditions for forming the HIL.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS):

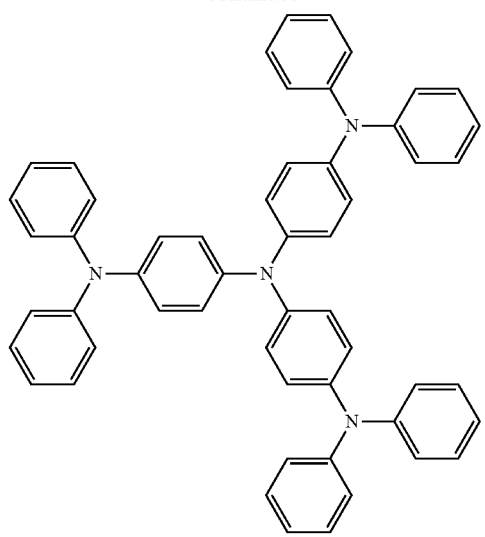

TDATA

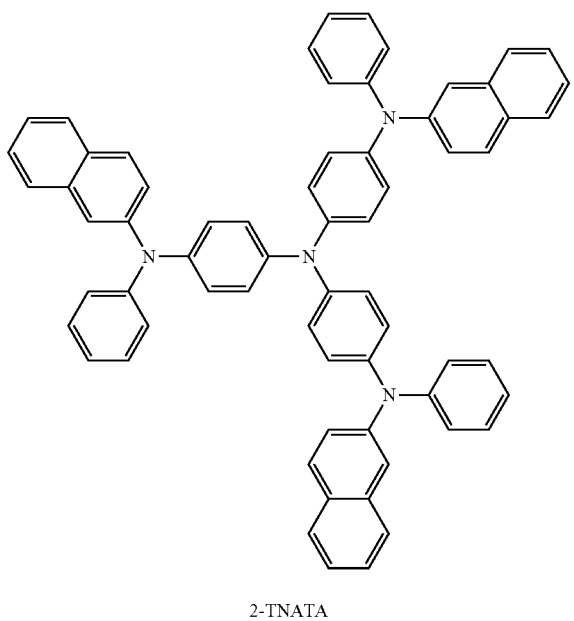

2-TNATA

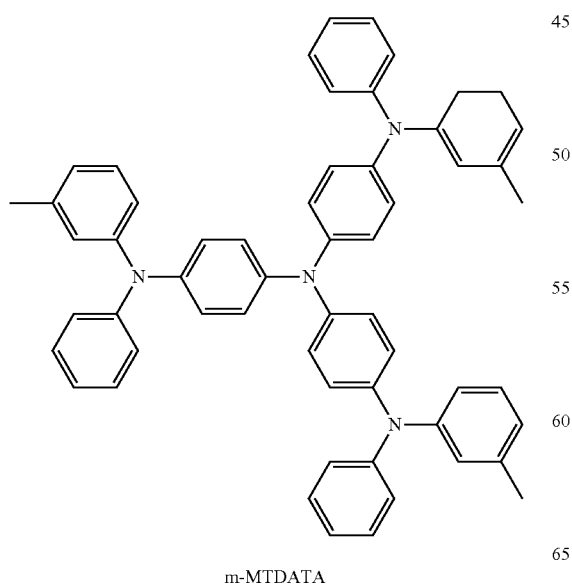

m-MTDATA

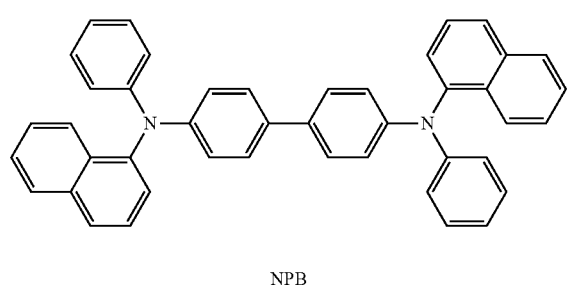

NPB

-continued

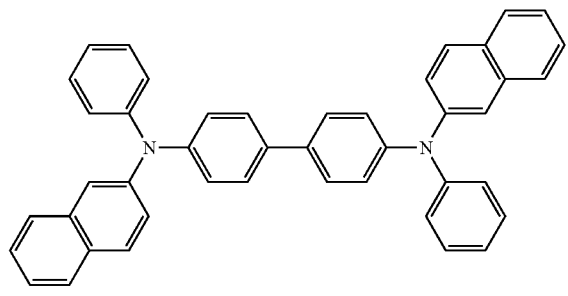

β-NPB

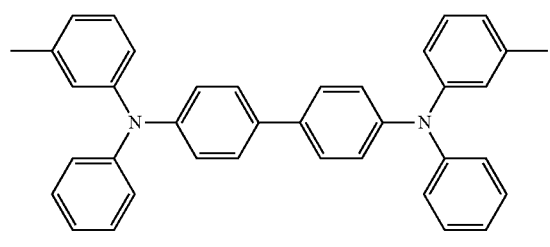

TPD

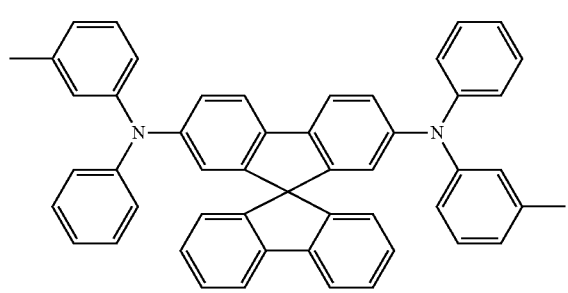

Spiro-TPD

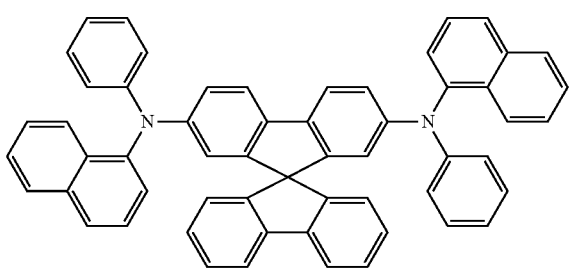

Spiro-NPB

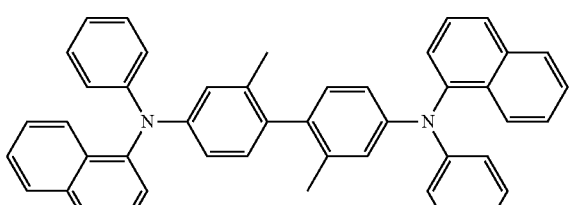

methylated NPB

-continued

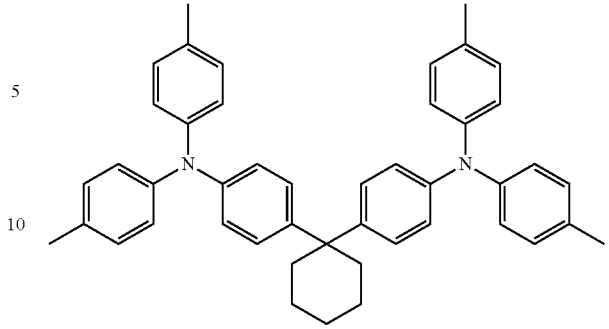

TAPC

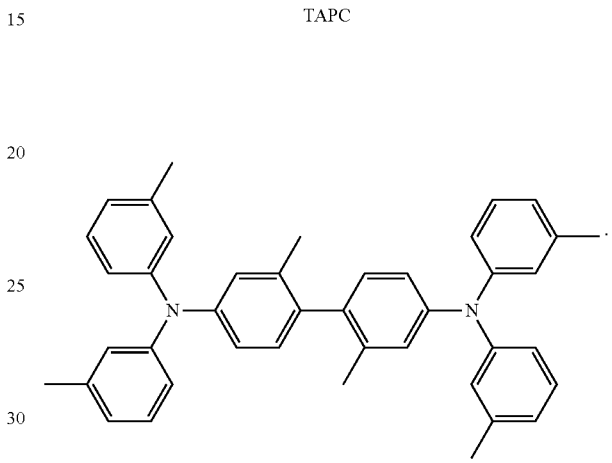

HMTPD

A thickness of the hole transport region may be in a range of about 100 Å to about 10,000 Å, for example, about 100 Å to about 1,000 Å. When the hole transport region includes both an HIL and an HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When thicknesses of the hole transport region, the HIL, and the HTL are within any of these ranges, hole transporting properties may be suitable or satisfactory without a substantial increase in a driving voltage.

The hole transport region may further include a charge-generating material to improve conductive properties, in addition to the materials described above. The charge-generating material may be homogeneously or non-homogeneously dispersed throughout the hole transport region.

The charge-generating material may include, for example, a p-dopant. The p-dopant may be selected from a quinone derivative, a metal oxide, and a cyano group-containing compound. Non-limiting examples of the p-dopant include quinone derivatives (such as tetracyanoquinonedimethane (TCNQ) and/or 2,3,5,6-tetrafluoro-tetracyano-1,4-benzo-quinonedimethane (F4-TCNQ)); metal oxides (such as tungsten oxide and/or molybdenum oxide), and Compound HT-D1 below, but the p-dopant is not limited thereto:

Compound HT-D1

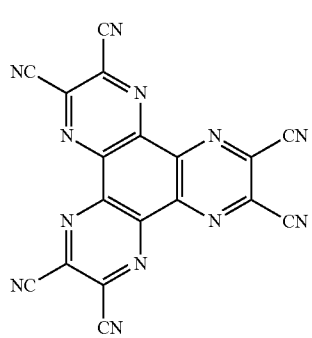

F4-TCNQ

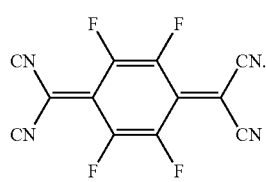

The hole transport region may include a buffer layer. The buffer layer may compensate for an optical resonance distance of light according to a wavelength of the light emitted from the emission layer, and thus, may help improve light-emission efficiency. In this regard, any suitable material that is included in the hole transport region may be used as a material that is included in the buffer layer. The EBL may help reduce and/or prevent electrons from being injected from the electron transport region.

The emission layer may be formed on the first electrode 110 or on the hole transport region by using one or more suitable methods, such as vacuum deposition, spin coating, casting, a LB method, ink-jet printing, laser-printing, and/or LITI. When the emission layer is formed by vacuum deposition and/or by spin coating, the deposition conditions and/or the coating conditions may be inferred based on the deposition conditions and/or the coating conditions for forming the HIL.

When the organic light-emitting device 10 is a full-color organic light-emitting device, the emission layer may be patterned into a red emission layer, a green emission layer, and a blue emission layer, according to an individual sub-pixel. Alternatively, the emission layer may have a structure of a red emission layer, a green emission layer, and a blue emission layer, each of which layers are sequentially stacked in the stated order. In this regard, a material emitting red light, a material emitting green light, and a material emitting blue light may have a mixed structure without having division of layers, thereby emitting white light.

The emission layer may include a host and a dopant.

The host may include, for example, at least one selected from TPBi, TBADN, ADN (also referred to herein as "DNA"), CBP, CDBP, and TCP:

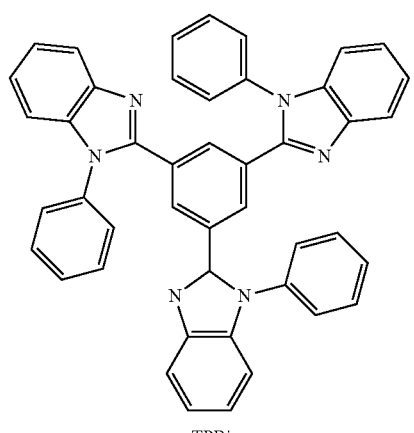

TPBi

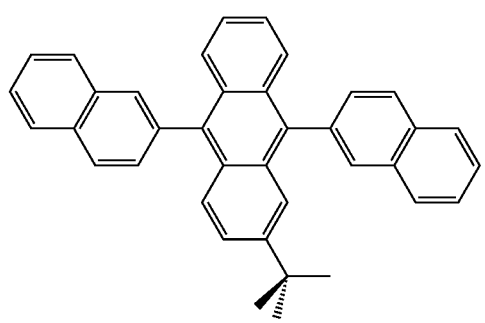

TBADN

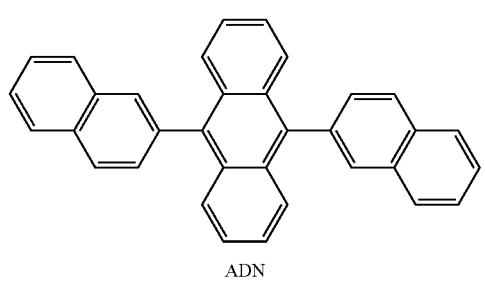

ADN

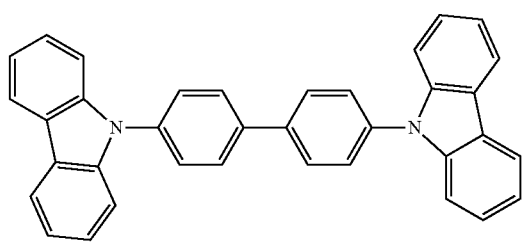

CBP

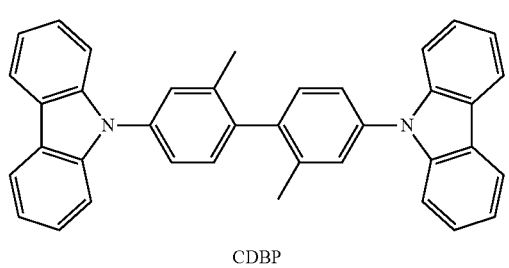

CDBP

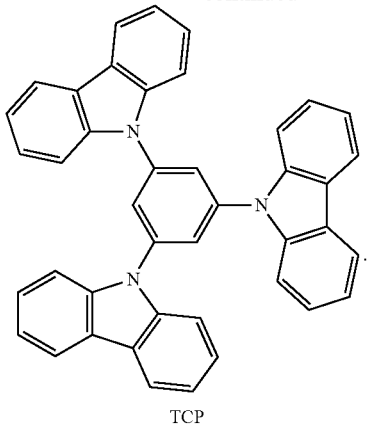

TCP

In some embodiments, the host may include a compound represented by Formula 301:

$$Ar_{301}\text{-}[(L_{301})_{xb1}\text{-}R_{301}]_{xb2}.$$ Formula 301

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1\text{-}C_{60}$ alkyl group, a $C_2\text{-}C_{60}$ alkenyl group, a $C_2\text{-}C_{60}$ alkynyl group, a $C_1\text{-}C_{60}$ alkoxy group, a $C_3\text{-}C_{10}$ cycloalkyl group, a $C_2\text{-}C_{10}$ heterocycloalkyl group, a $C_3\text{-}C_{10}$ cycloalkenyl group, a $C_2\text{-}C_{10}$ heterocycloalkenyl group, a $C_6\text{-}C_{60}$ aryl group, a $C_6\text{-}C_{60}$ aryloxy group, a $C_6\text{-}C_{60}$ arylthio group, a $C_1\text{-}C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may each independently be selected from hydrogen, a $C_1\text{-}C_{60}$ alkyl group, a $C_2\text{-}C_{60}$ alkenyl group, a $C_6\text{-}C_{60}$ aryl group, and a $C_1\text{-}C_{60}$ heteroaryl group), $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1\text{-}C_{20}$ alkyl group, a $C_1\text{-}C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, $R_{301}$ may be selected from:

a $C_1\text{-}C_{20}$ alkyl group and a $C_1\text{-}C_{20}$ alkoxy group;

a $C_1\text{-}C_{20}$ alkyl group and a $C_1\text{-}C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1\text{-}C_{20}$ alkyl group, a $C_1\text{-}C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A:

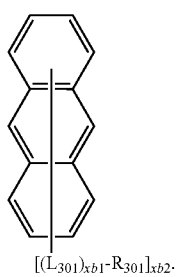

Formula 301A $[(L_{301})_{xb1}$-$R_{301}]_{xb2}$.

Descriptions of substituents of Formula 301A may be inferred based on the descriptions provided above.

The compound of Formula 301 may include at least one of Compounds H1 to H42. In compounds H1 to H42, "D" may refer to deuterium.

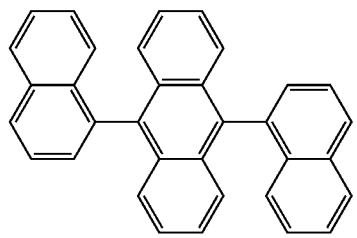

H1

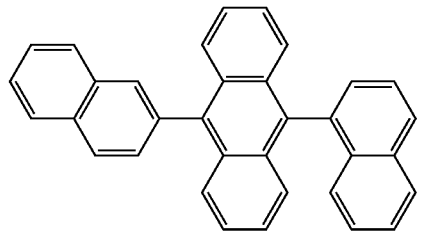

H2

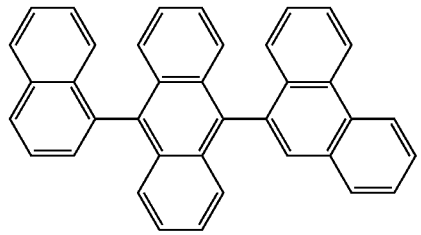

H3

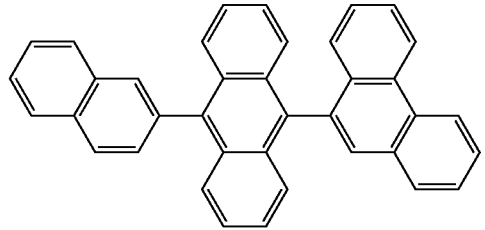

H4

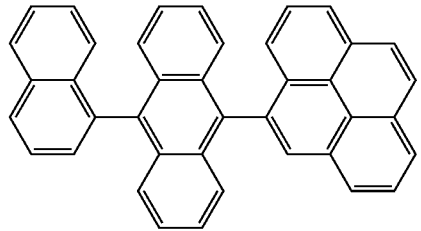

H5

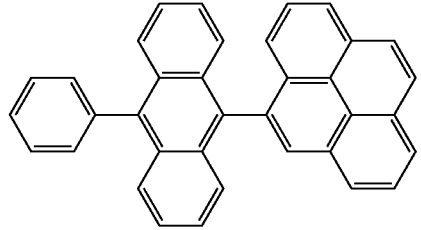

H6

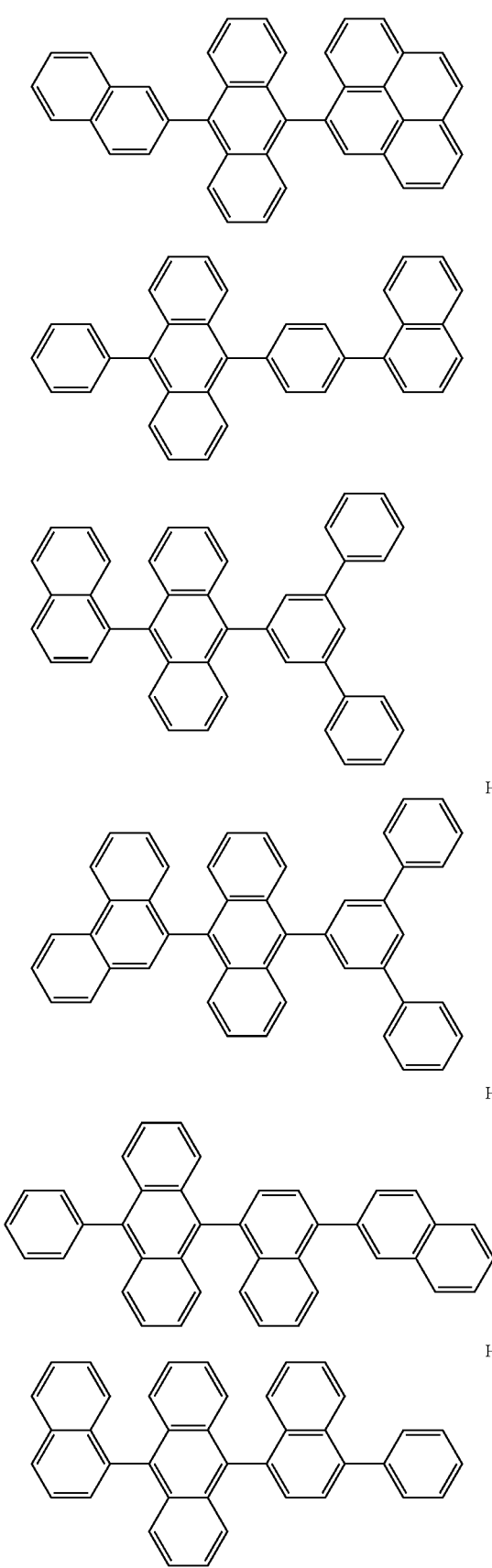
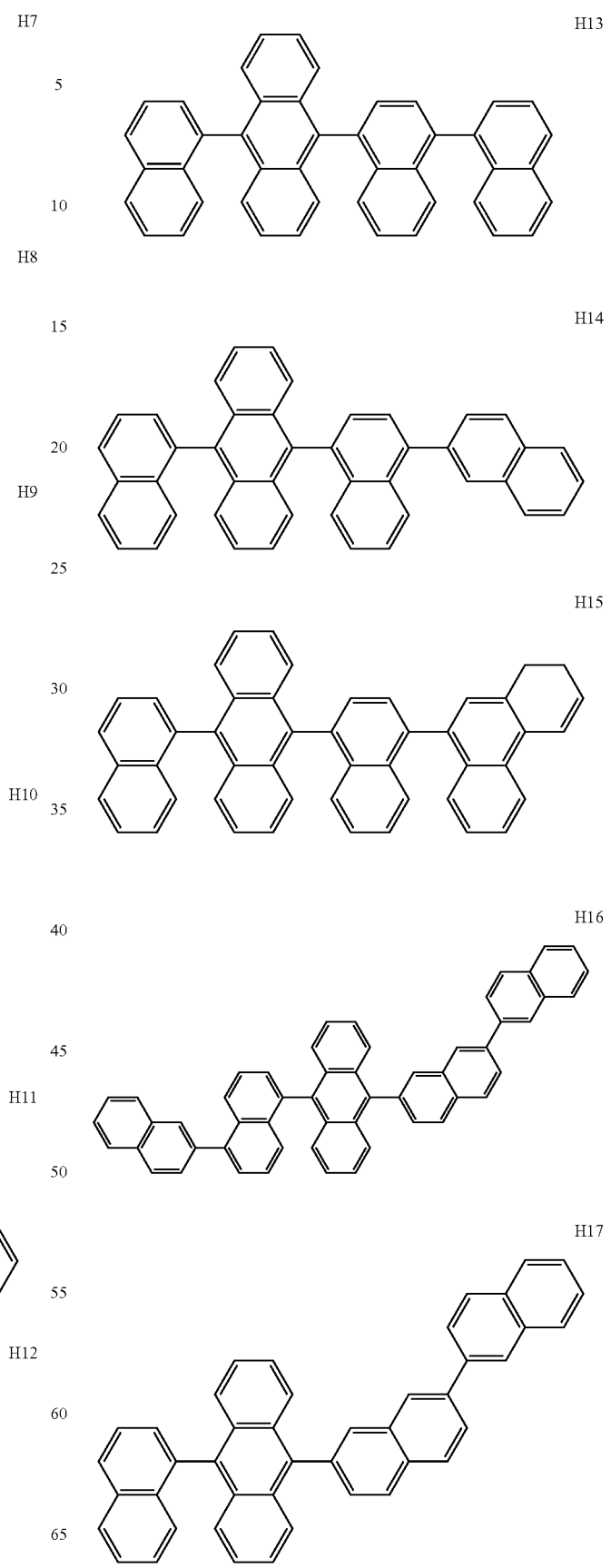

-continued
H18
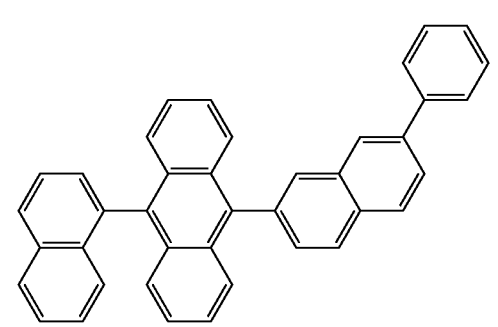
H19
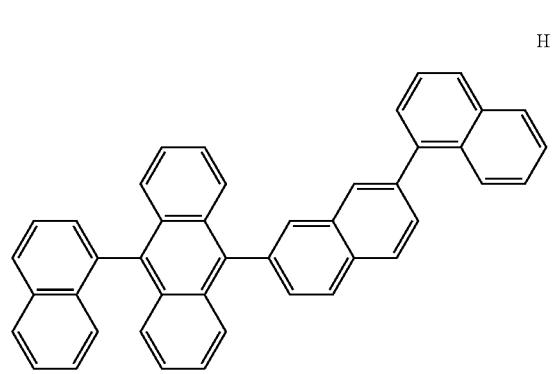
H20
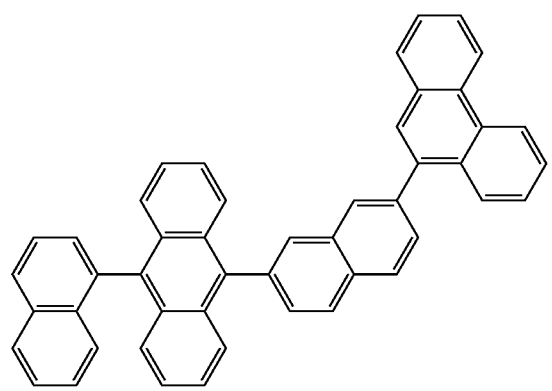
H21
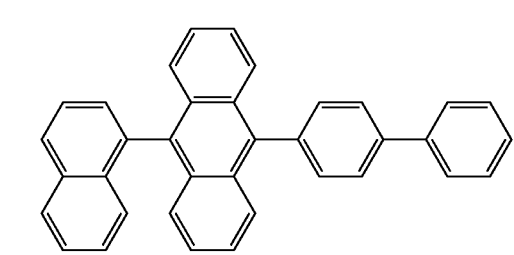
H22
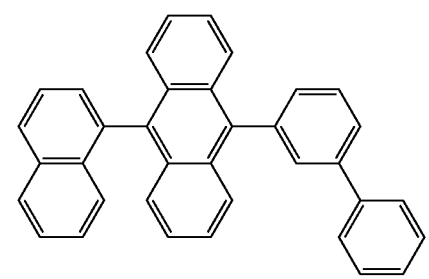
-continued
H23
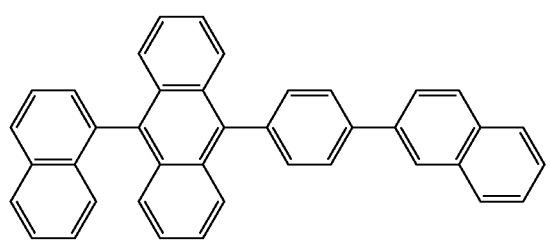
H24
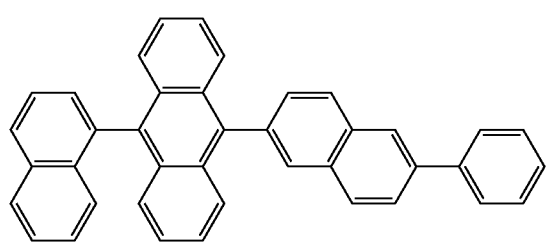
H25
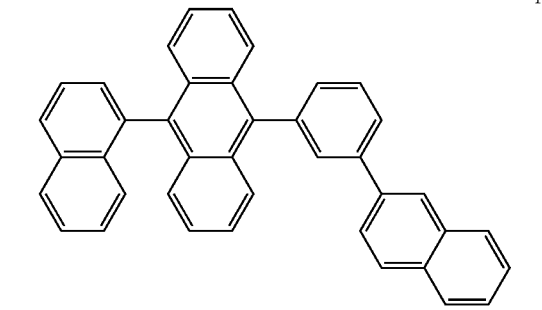
H26
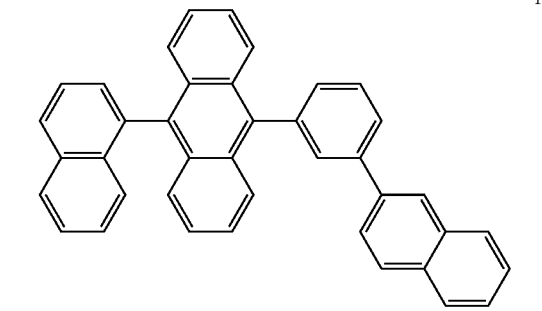
H27
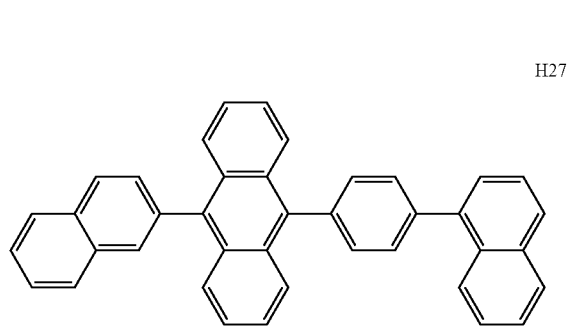

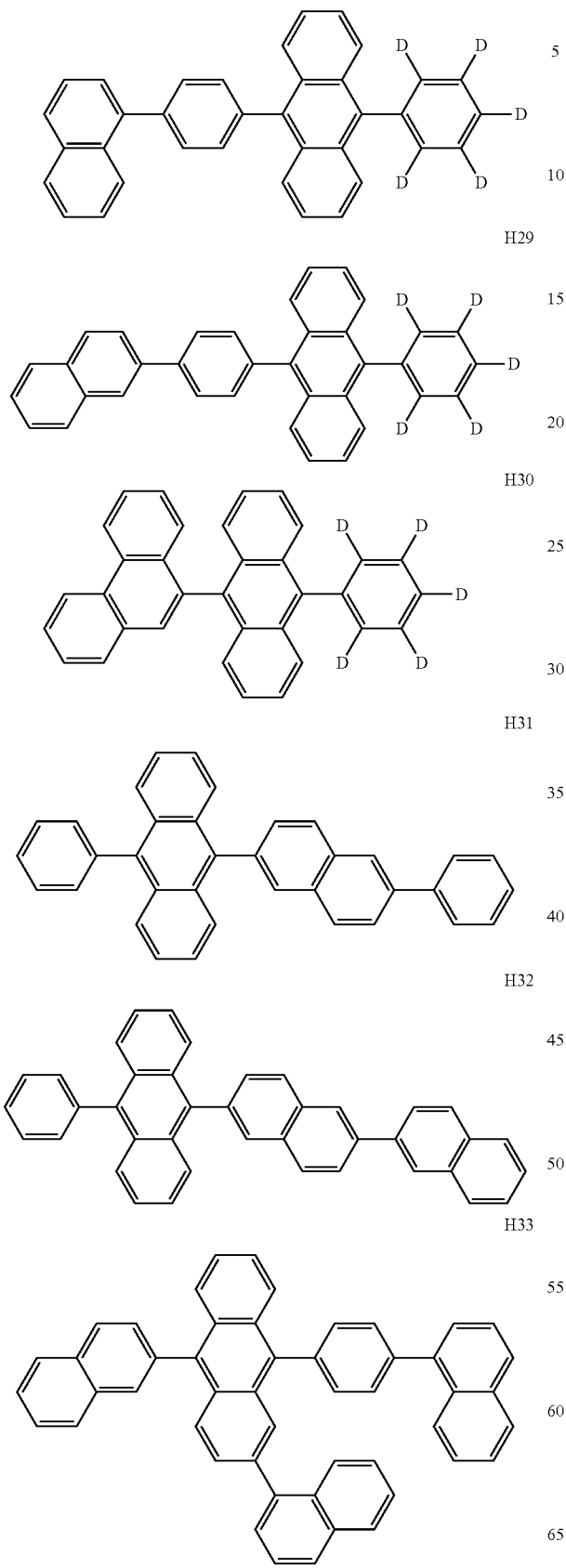

H37
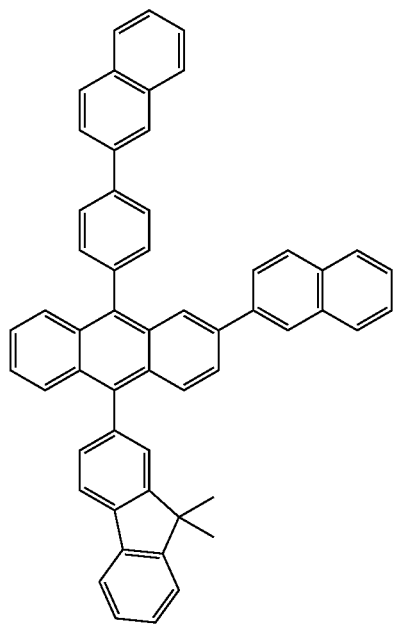
H38
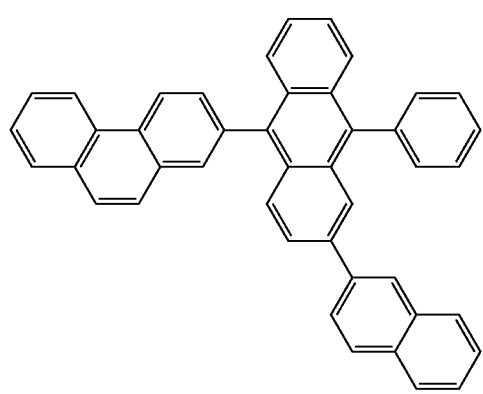
H39
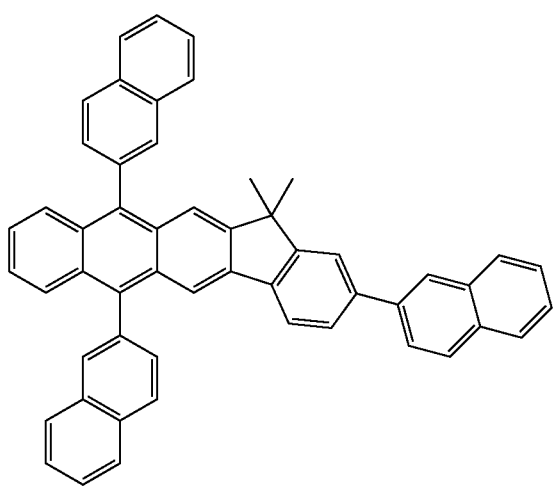
H40
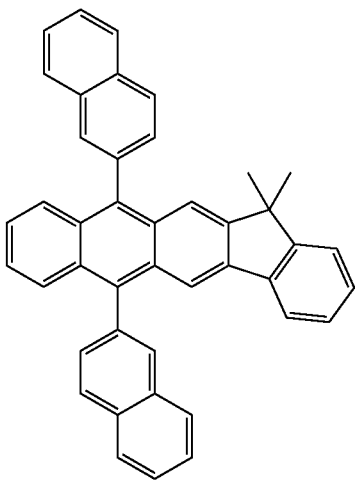
H41
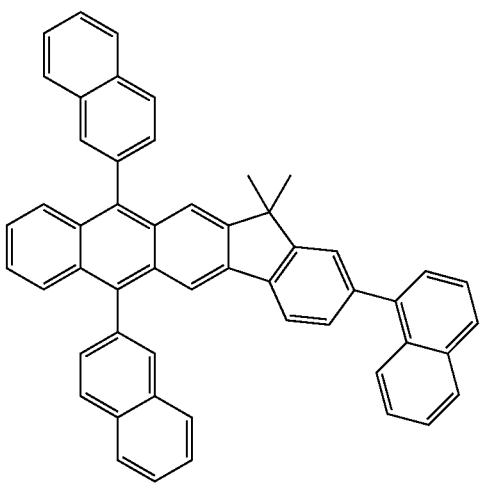
H42
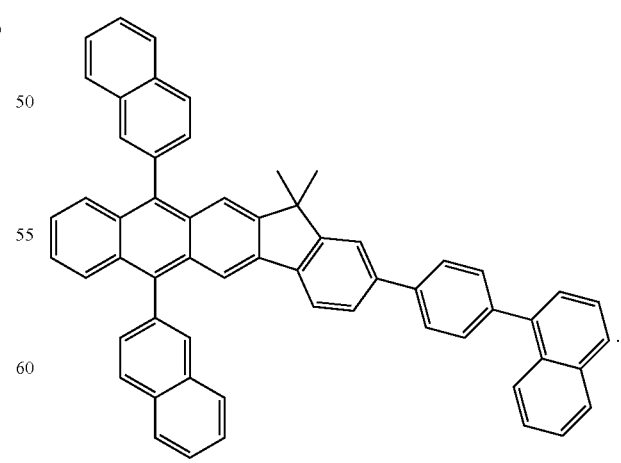
In some embodiments, the host may include at least one of Compounds H43 to H49:

H43
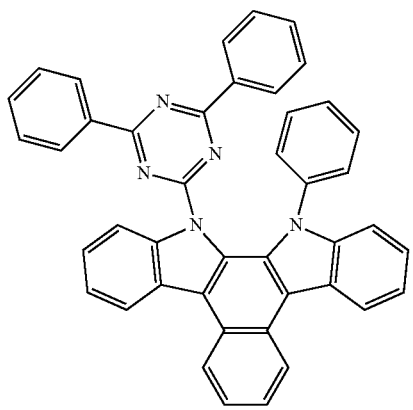
H44
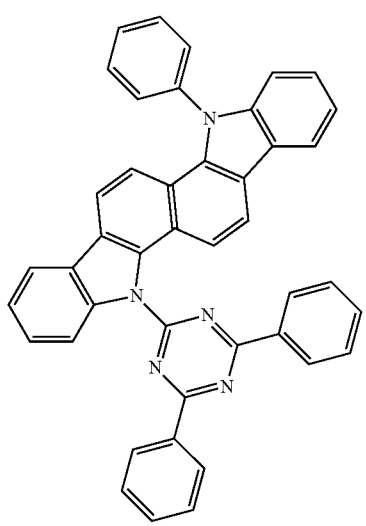
H45
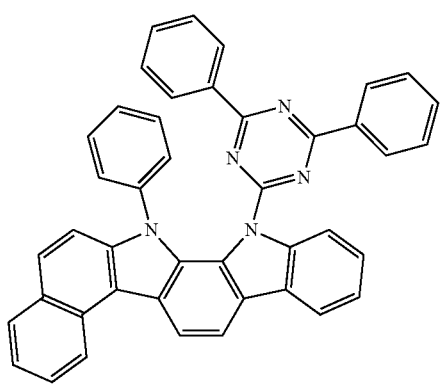
H46
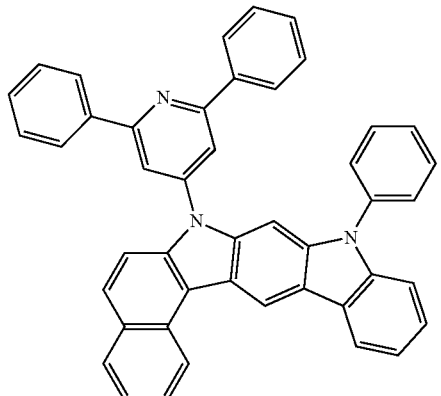
H47
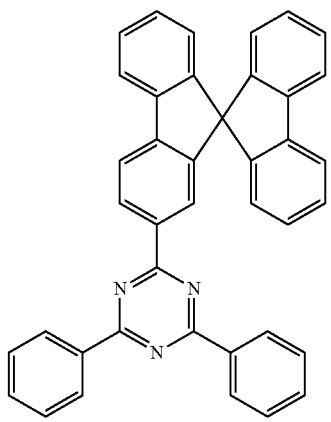
H48
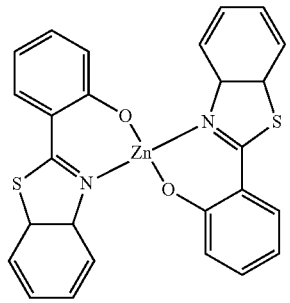
H49
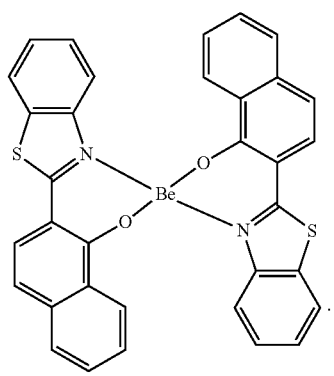
The dopant may include at least one selected from a fluorescent dopant and a phosphorescent dopant.
The phosphorescent dopant may include an organic metal complex represented by Formula 401:

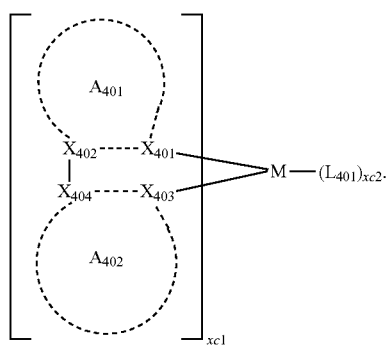

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may each independently be nitrogen or carbon, rings $A_{401}$ and $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group (e.g., non-aromatic condensed polycyclic group), a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), wherein $Q_{401}$ to $Q_{407}$, $Q_{411}$ to $Q_{4177}$ and $Q_{421}$ to $Q_{427}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group;

$L_{401}$ may be an organic ligand, xc1 may be 1, 2, or 3, and xc2 may be 0, 1, 2, or 3.

In Formula 401, $L_{401}$ may be a monovalent organic ligand, a divalent organic ligand, or a trivalent organic ligand. For example, in Formula 401, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monoxide ligand, a nitrile ligand, a cyano group ligand, and a phosphorus ligand (e.g., phosphine and/or phosphite).

When $A_{401}$ in Formula 401 has two or more substituents, two or more substituents of $A_{401}$ may be bonded (e.g., coupled) to each other to form a saturated ring or an unsaturated ring.

When $A_{402}$ in Formula 401 has two or more substituents, two or more substituents of $A_{402}$ may be bonded (e.g., coupled) to each other to form a saturated ring or an unsaturated ring.

When xc1 in Formula 401 is 2 or more, a plurality of ligands

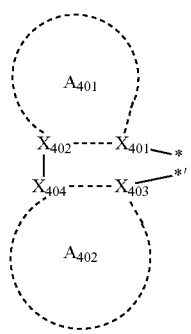

in Formula 401 may be identical to or different from each other. When xc1 in Formula 401 is 2 or more, $A_{401}$ and $A_{402}$ of one ligand may each independently be respectively bonded (e.g., coupled) to $A_{401}$ and $A_{402}$ of other neighboring ligands, either directly (e.g., via a bond such as a single bond) or via a linking group (e.g., a $C_1$-$C_5$ alkylene group, —N(R')— (wherein R' may be a $C_1$-$C_{10}$ alkyl group or a $C_6$-$C_{20}$ aryl group), and/or —C(=O)—).

The phosphorescent dopant may include at least one of Compounds PD1 to PD74:

PD1

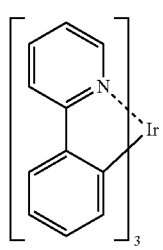

PD2

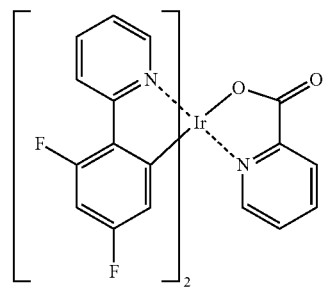

PD3

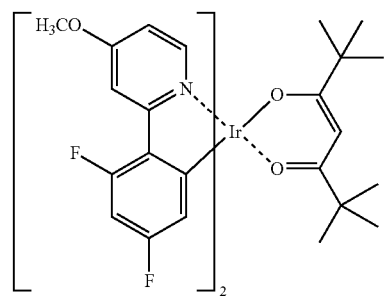

PD4

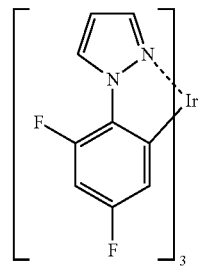

PD5

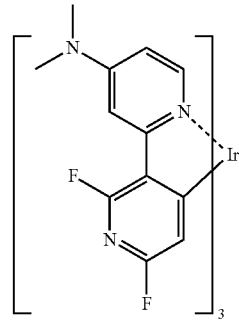

PD6

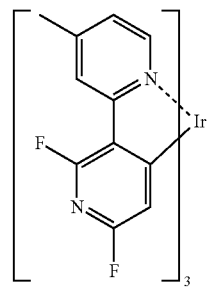

-continued
PD7
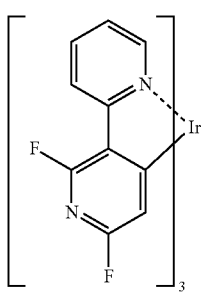
PD8
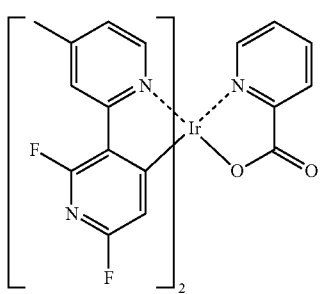
PD9
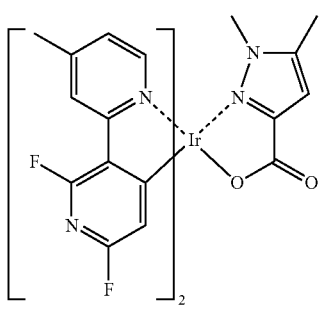
PD10
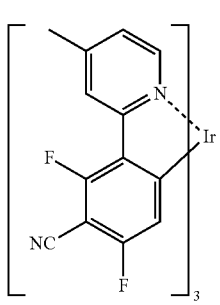
PD11
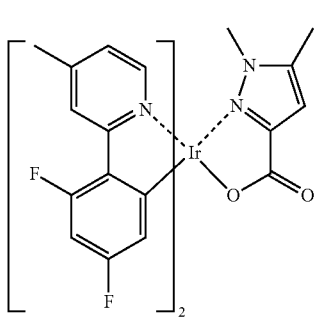
-continued
PD12
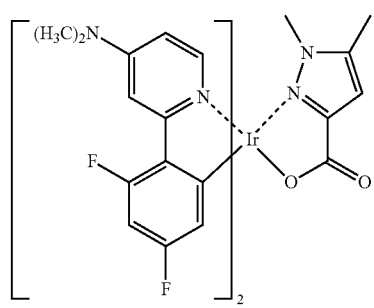
PD13
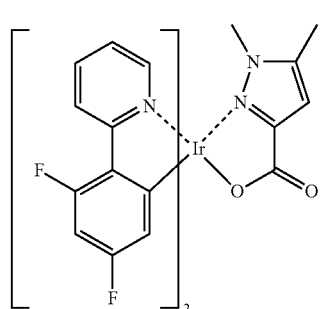
PD14
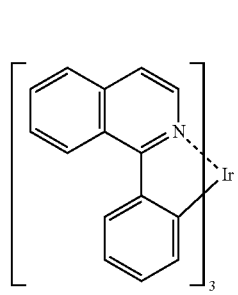
PD15
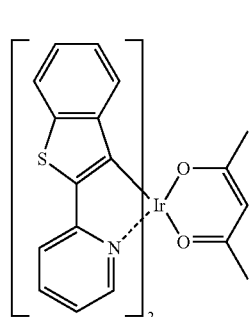
PD16
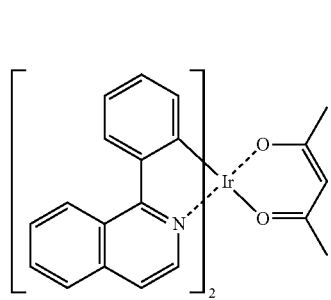

PD17 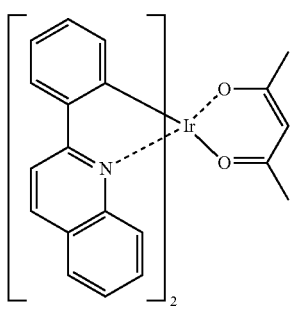
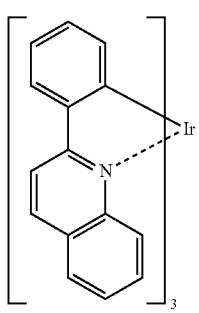
PD19 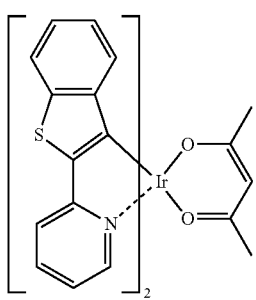
PD20 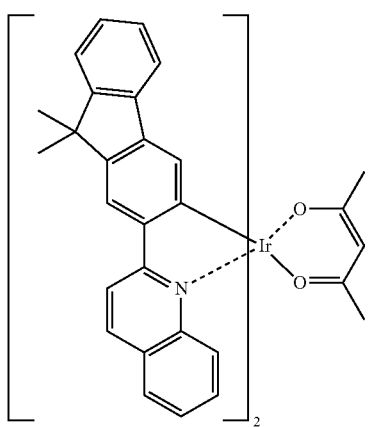
PD21 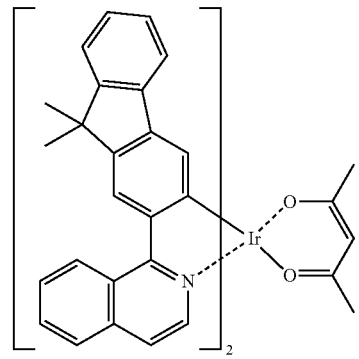
PD22 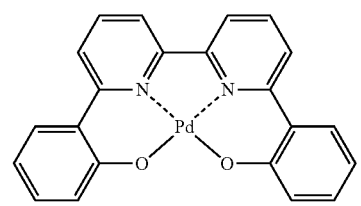
PD23 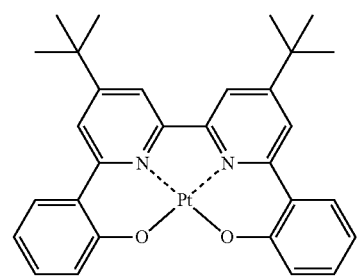
PD24 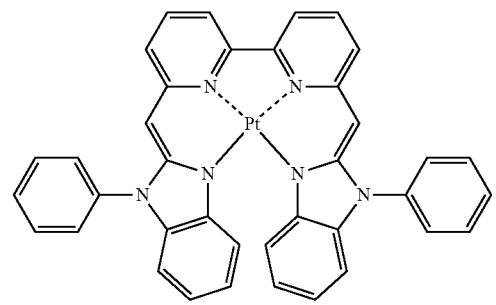
PD25 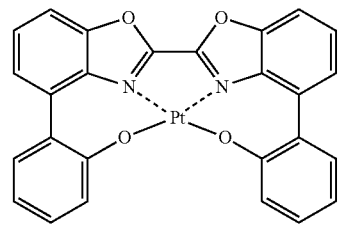
PD26 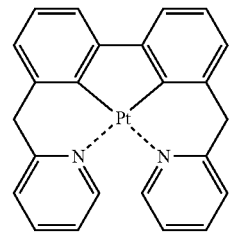

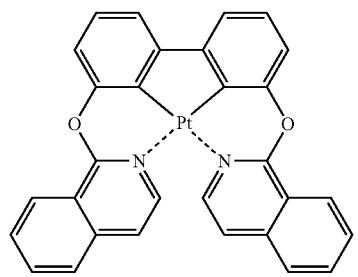
PD27
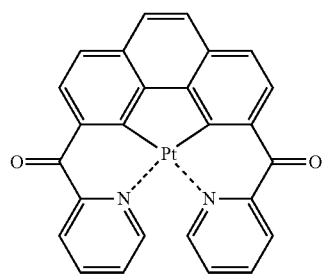
PD28
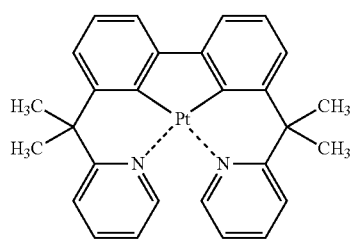
PD29
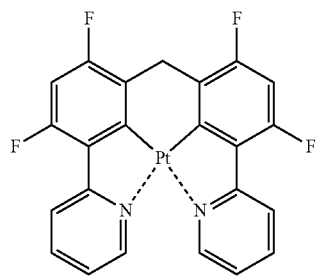
PD30
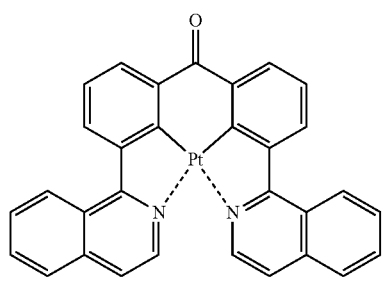
PD31
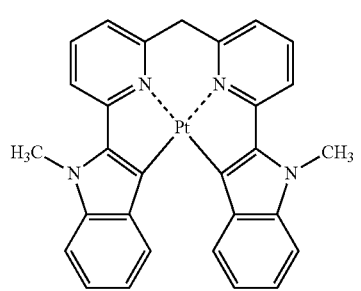
PD32
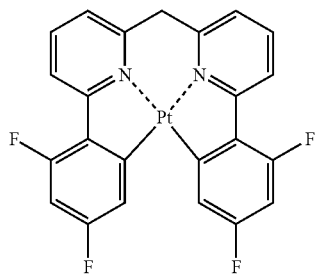
PD33
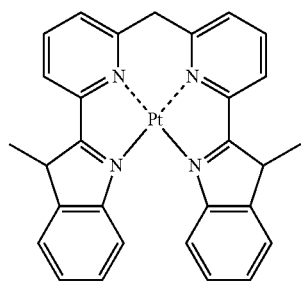
PD34
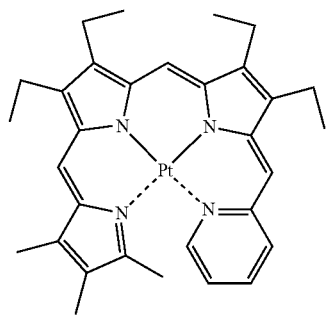
PD35
PD36
PD37

PD38
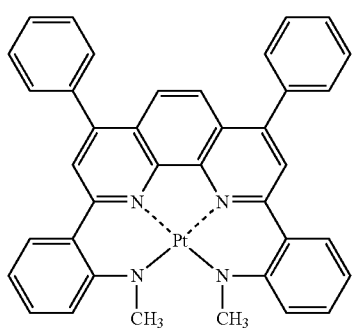
PD39
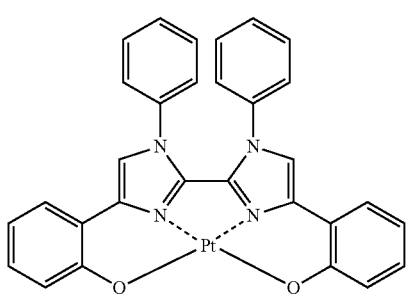
PD40
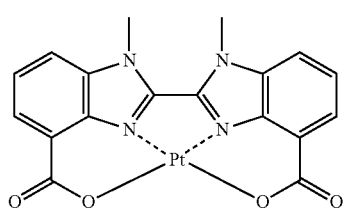
PD41
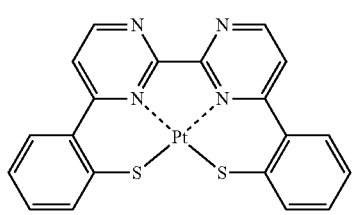
PD42
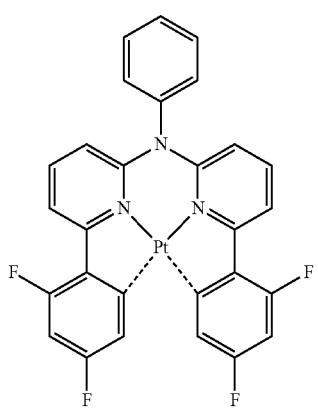
PD43
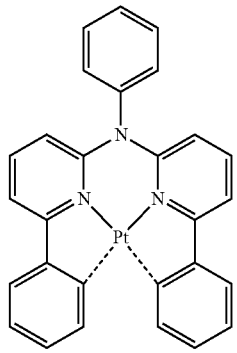
PD44
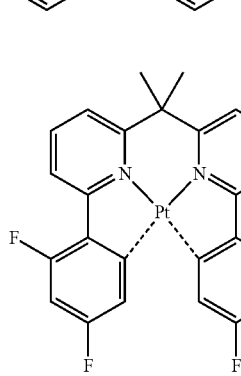
PD45
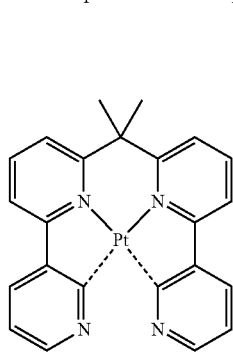
PD46
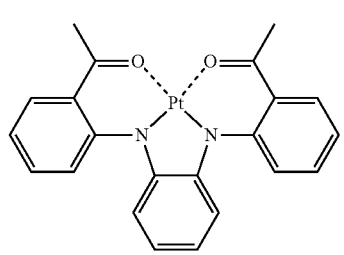
PD47
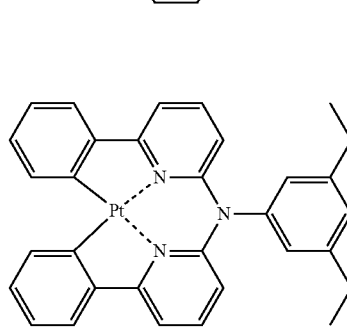

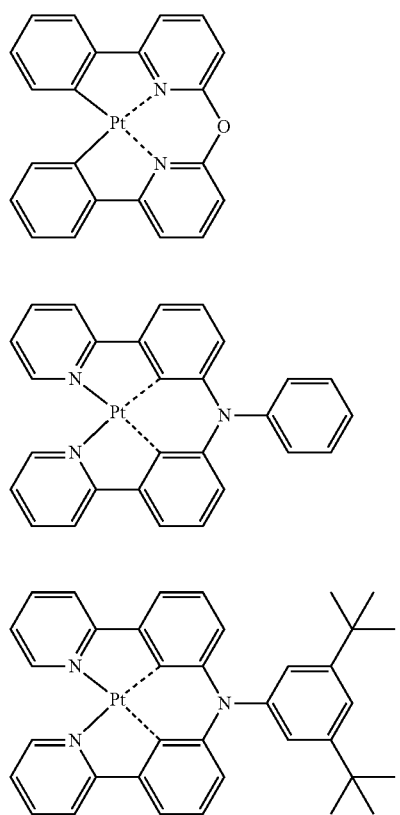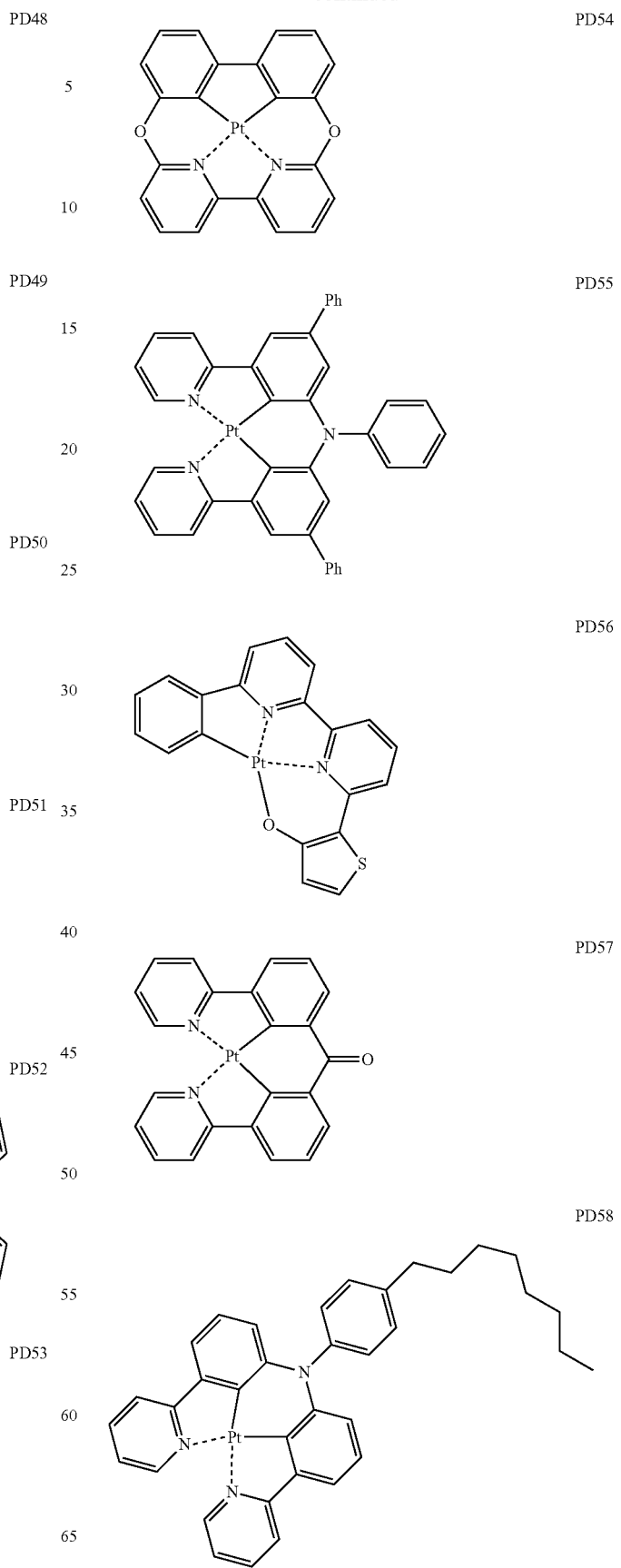

PD59 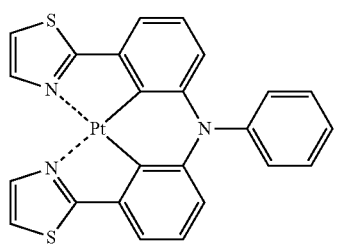
PD60 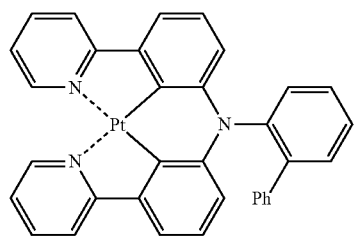
PD61 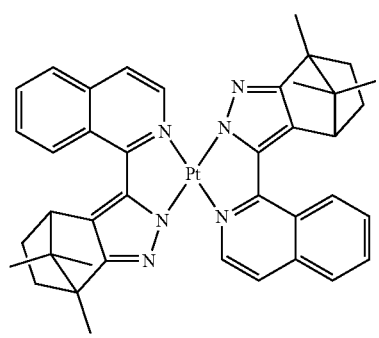
PD62 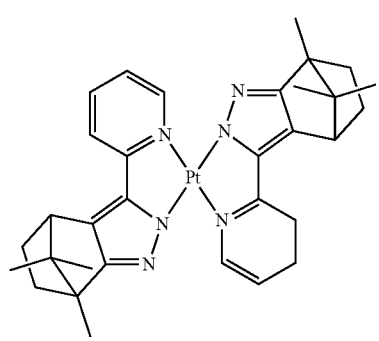
PD63 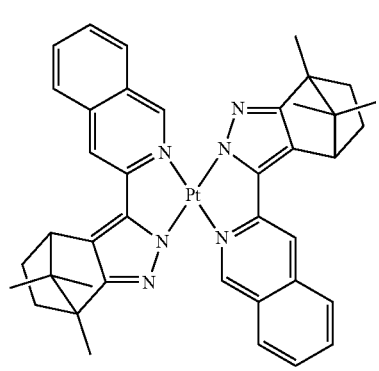
PD64 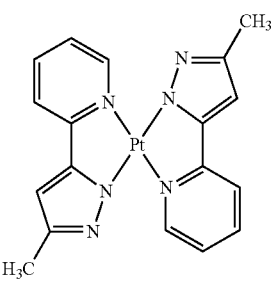
PD65 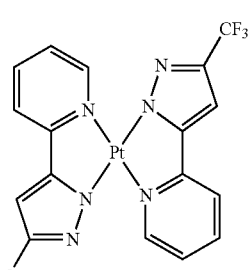
PD66 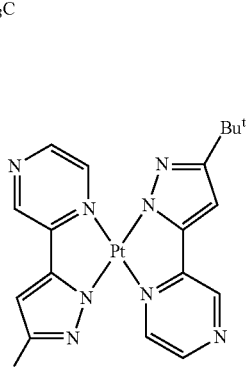
PD67 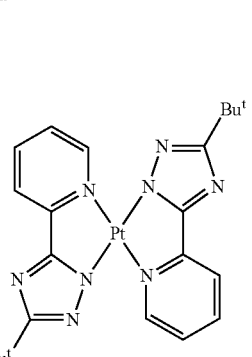
PD68 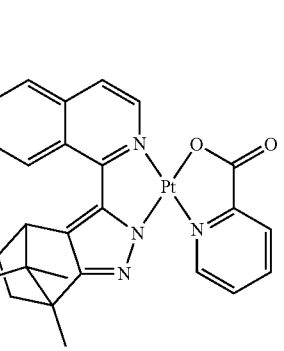

PD69 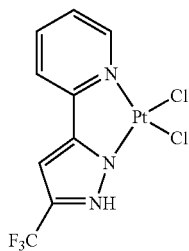
PD70 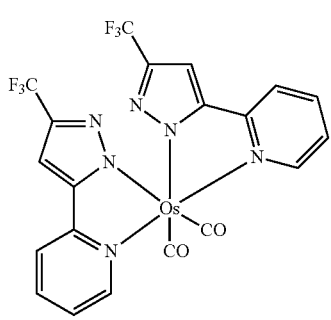
PD71 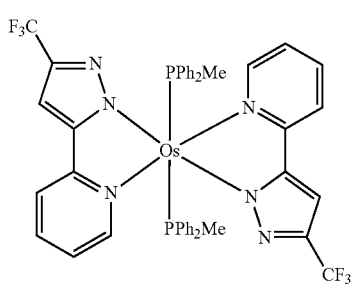
PD72 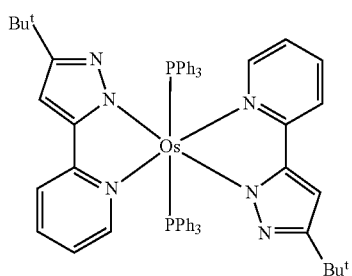
PD73 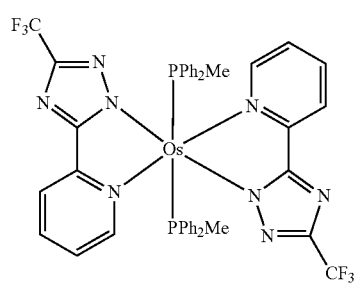
PD74 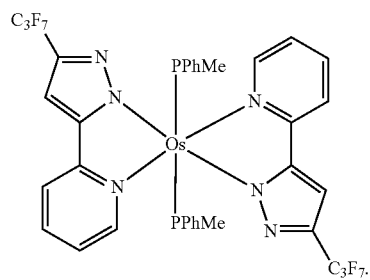
In some embodiments, the phosphorescent dopant may include PtOEP:
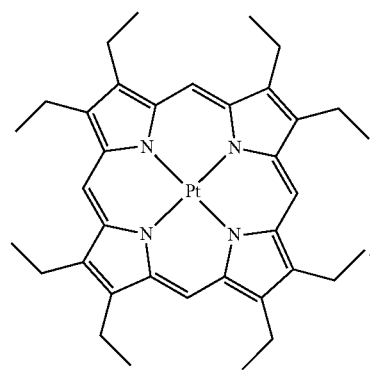
PtOEP
The fluorescent dopant may include at least one selected from DPVBi, DPAVBi, TBPe, DCM, DCJTB, Coumarin 6, and C545T:
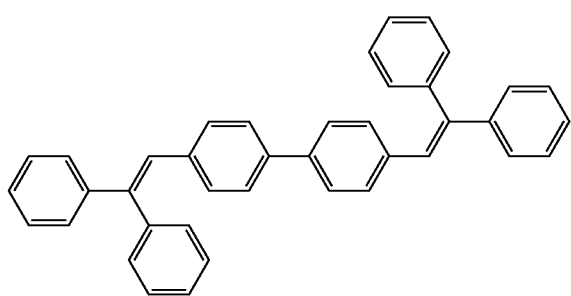
DPVBi

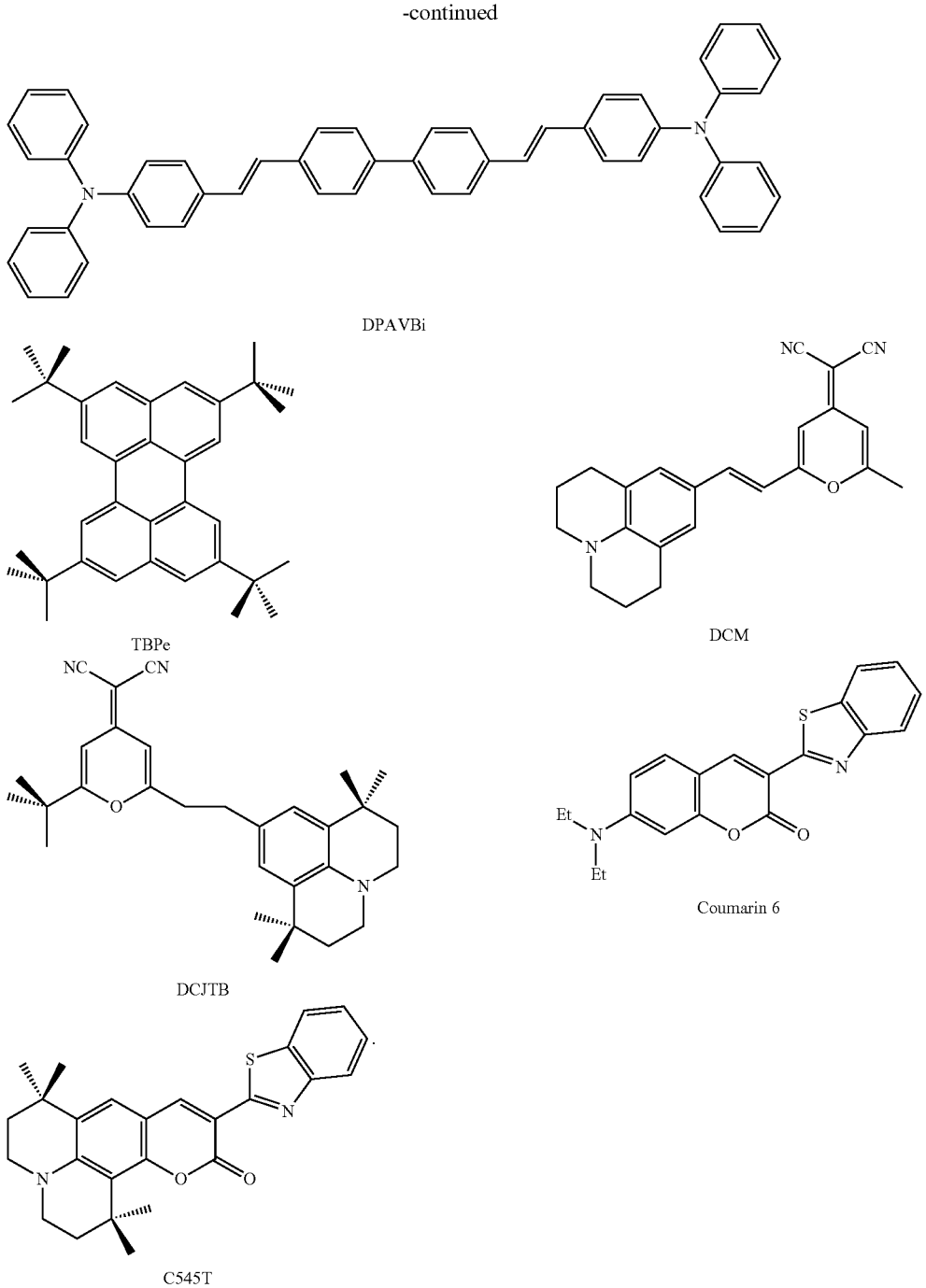

In some embodiments, the fluorescent dopant may include a compound represented by Formula 501:

Formula 501

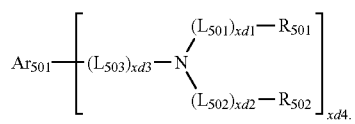

In Formula 501,

Ar$_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{501}$ to $L_{503}$ may each independently be defined the same as $L_{301}$ in the present specification, $R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xd4 may be selected from 1, 2, 3, and 4.

The fluorescent dopant may include at least one of Compounds FD1 to FD8:

FD1

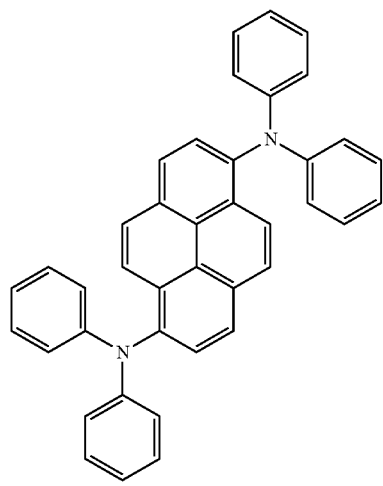

-continued

FD2

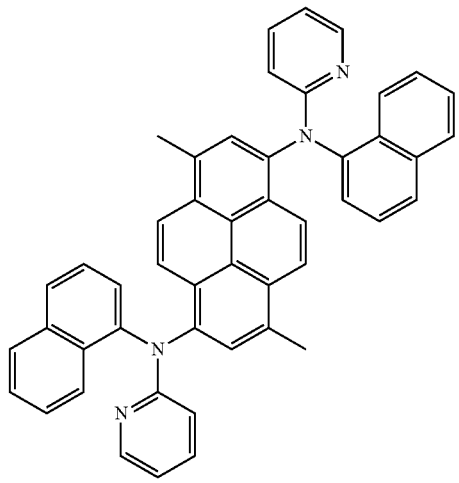

FD3

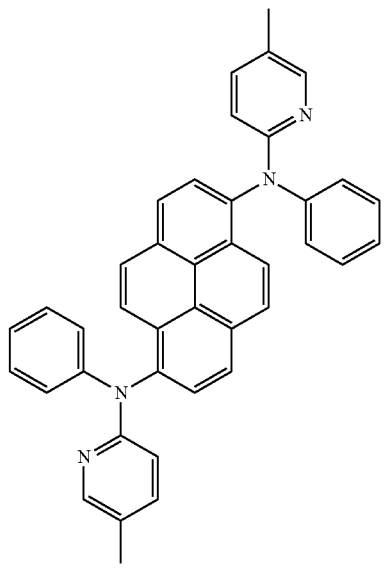

FD4

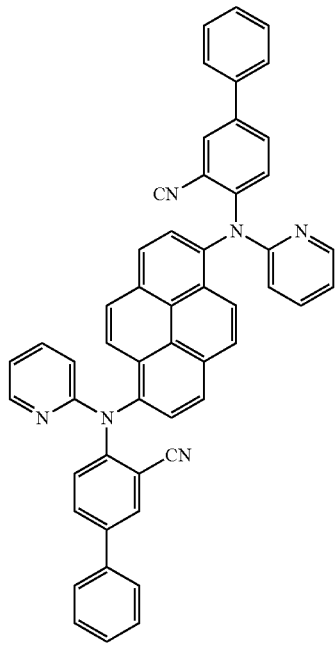

-continued

FD5
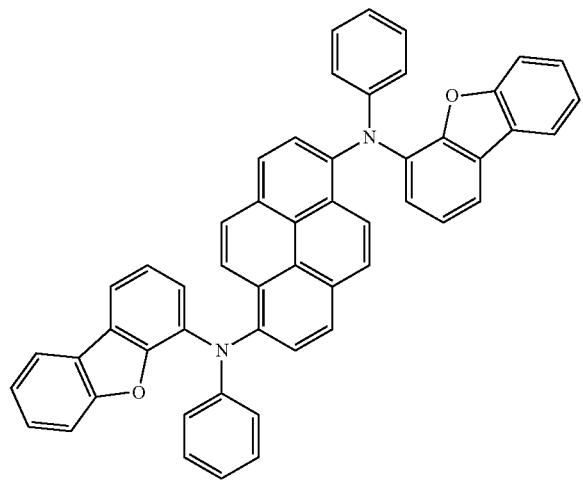

FD6
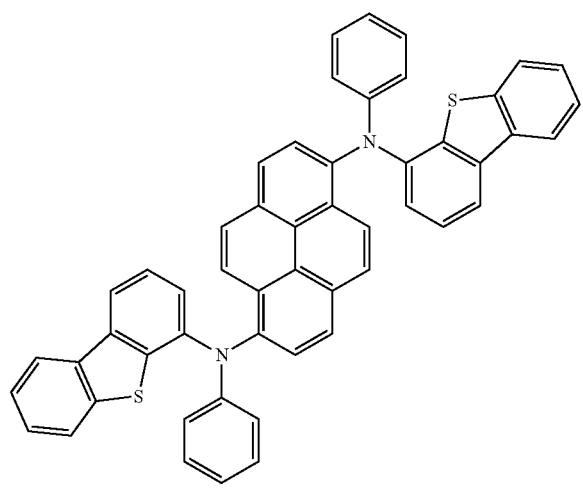

FD7
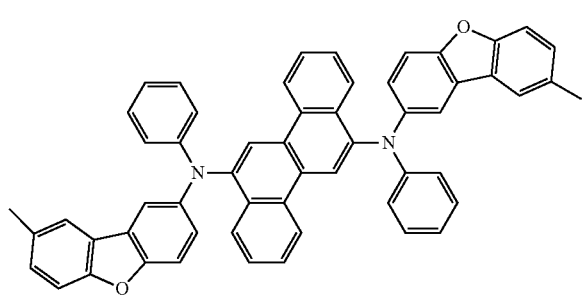

FD8
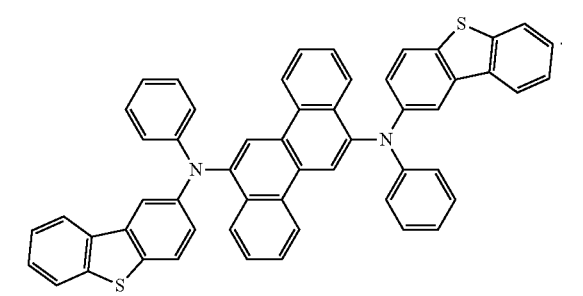

An amount of the dopant included in the emission layer may be from about 0.01 to about 15 parts by weight, based on 100 parts by weight of the host.

A thickness of the emission layer may be from about 100 Å to about 1,000 Å, for example, about 200 Å to about 600 Å. When the thickness of the emission layer is within any of these ranges, excellent emission characteristics may be obtained without a substantial increase in driving voltage.

The electron transport region may be disposed (e.g., positioned) on the emission layer.

The electron transport region may include at least one selected from an HBL, an ETL, and an EIL.

When the electron transport region includes an HBL, the HBL may be formed on the emission layer by using one or more suitable methods, such as vacuum deposition, spin coating, casting, a Langmuir-Blodgett (LB) method, ink-jet printing, laser-printing, and/or laser induced thermal imaging (LITI). When the HBL is formed by vacuum deposition and/or by spin coating, the deposition conditions and/or the coating conditions may be inferred based on the deposition conditions and/or coating conditions for forming the HIL.

The HBL may include, for example, at least one selected from BCP and Bphen:

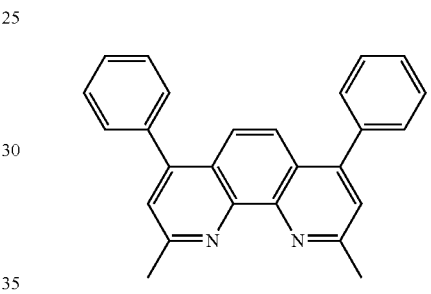

BCP

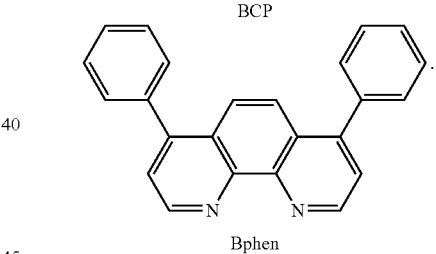

Bphen

A thickness of the HBL may be from about 20 Å to about 1,000 Å, for example, about 30 Å to about 300 Å. When the thickness of the HBL is within any of these ranges, excellent hole blocking characteristics may be obtained without a substantial increase in driving voltage.

The electron transport region may have a structure of ETL/EIL or a structure of HBL/ETL/EIL, wherein the layers of each structure are sequentially stacked in the stated order from the emission layer.

According to an example embodiment, the organic layer 150 may include the electron transport region between the emission layer and the second electrode 190, and the electron transport region may include an ETL. The ETL may consist of a plurality of layers. For example, the electron transport region may include a first ETL and a second ETL.

According to an example embodiment, the electron transport region may include the compound of Formula 1.

According to an example embodiment, the electron transport layer (ETL) may include the compound of Formula 1.

A thickness of the ETL may be from about 100 Å to about 1,000 Å, for example, about 150 Å to about 500 Å. When the thickness of the ETL is within any of these ranges, excellent electron transporting characteristics may be obtained without a substantial increase in driving voltage.

The ETL may further include, in addition to the materials described above, a metal-containing material.

The metal-containing material may include a Li complex. The Li complex may include, for example, Compound ET-D1 (e.g., lithium quinolate (LiQ)) and/or Compound ET-D2:

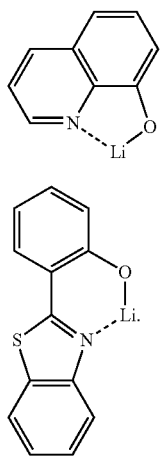

ET-D1

ET-D2

The electron transport region may include an EIL that facilitates electron injection from the second electrode 190.

The EIL may be formed on the ETL by using one or more suitable methods, such as vacuum deposition, spin coating, casting, a LB method, ink-jet printing, laser-printing, and/or LITI. When the EIL is formed by vacuum deposition and/or by spin coating, the deposition conditions and/or the coating conditions may be inferred based on the deposition conditions and/or the coating conditions for forming the HIL.

The EIL may include at least one selected from LiF, NaCl, CsF, Li$_2$O, BaO, and LiQ.

A thickness of the EIL may be from about 1 Å to about 100 Å, for example, from about 3 Å to about 90 Å. When the thickness of the EIL is within any of these ranges, suitable or satisfactory electron injecting characteristics may be obtained without a substantial increase in driving voltage.

The second electrode 190 may be disposed (e.g., positioned) on the organic layer 150. The second electrode 190 may be a cathode, which is an electron injection electrode. Here, a material for forming the second electrode 190 may be a material having a low work function, for example, a metal, an alloy, an electrically conductive compound, or a mixture thereof. Non-limiting examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may include ITO and/or IZO. The second electrode 190 may be a reflective electrode, a semi-transmissive electrode, or a transmissive electrode.

The organic layer 150 of the organic light-emitting device 10 may be formed by a deposition method using compounds according to example embodiments of the present disclosure, or by a wet coating method using solutions of compounds according to example embodiments of the present disclosure.

The organic light-emitting device 10 according to an example embodiment may be included in various flat panel display apparatuses, for example, in a passive matrix OLED display apparatus and/or an active matrix OLED display apparatus. For example, when the organic light-emitting device 10 is utilized in the active matrix OLED display apparatus, the first electrode of the organic light-emitting device 10 may be disposed (e.g., positioned) on a side of the substrate, and may be a pixel electrode that is electrically connected (e.g., coupled) to source and drain electrodes of a thin film transistor. In some embodiments, the organic light-emitting device 10 may be utilized in a flat panel display apparatus that can display images on both sides of the screen.

Hereinbefore, the organic light-emitting device 10 has been described in connection with the drawing. However, the organic light-emitting device 10 is not limited to the embodiments described above.

Hereinafter, representative substituents of the substituents used in the present specification are defined (carbon numbers recited for the substituents are non-limiting and do not limit characteristics of the substituents, and and unless stated otherwise, the definition of the substituent is consistent with a general definition thereof).

A $C_1$-$C_{60}$ alkyl group as used herein may refer to a linear or branched aliphatic hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein may refer to a divalent group having the same structure as the $C_1$-$C_{60}$ alkyl group.

A $C_1$-$C_{60}$ alkoxy group as used herein may refer to a monovalent group represented by —OA$_{101}$ (wherein A$_{101}$ is the $C_1$-$C_{60}$ alkyl group), and non-limiting examples thereof include a methoxy group, an ethoxy group, and an iso-propoxy group.

A $C_2$-$C_{60}$ alkenyl group as used herein may refer to a hydrocarbon group having at least one carbon double bond at one or more positions along the hydrocarbon chain of the $C_2$-$C_{60}$ alkyl group (e.g., in a middle chain or at either terminal end of the $C_2$-$C_{60}$ alkyl group), and non-limiting examples thereof include an ethenyl group, a propenyl group, and a butenyl group. A $C_2$-$C_{60}$ alkenylene group as used herein may refer to a divalent group having the same structure as the $C_2$-$C_{60}$ alkenyl group.

A $C_2$-$C_{60}$ alkynyl group as used herein may refer to a hydrocarbon group having at least one carbon triple bond at one or more positions along the hydrocarbon chain of the $C_2$-$C_{60}$ alkyl group (e.g., in a middle chain or at either terminal end of the $C_2$-$C_{60}$ alkyl group), and non-limiting examples thereof are an ethynyl group and a propynyl group. A $C_2$-$C_{60}$ alkynylene group as used herein may refer to a divalent group having the same structure as the $C_2$-$C_{60}$ alkynyl group.

A $C_3$-$C_{10}$ cycloalkyl group as used herein may refer to a monovalent hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group as used herein may refer to a divalent group having the same structure as the $C_3$-$C_{10}$ cycloalkyl group.

A $C_2$-$C_{10}$ heterocycloalkyl group as used herein may refer to a monovalent monocyclic group having at least one heteroatom selected from N, O, P, and S as a ring-forming atom and 1 to 10 carbon atoms, and non-limiting examples thereof include a tetrahydrofuranyl group and a tetrahydrothiophenyl group. A $C_2$-$C_{10}$ heterocycloalkylene group as used herein may refer to a divalent group having the same structure as the $C_2$-$C_{10}$ heterocycloalkyl group.

A $C_3$-$C_{10}$ cycloalkenyl group as used herein may refer to a monovalent monocyclic group that has 3 to 10 carbon atoms and at least one double bond in the ring thereof and does not have aromaticity, and non-limiting examples thereof include a cyclopentenyl group, a cyclohexenyl group, and a cycloheptenyl group. A $C_3$-$C_{10}$ cycloalkenylene group as used herein may refer to a divalent group having the same structure as the $C_3$-$C_{10}$ cycloalkenyl group.

A $C_2$-$C_{10}$ heterocycloalkenyl group as used herein may refer to a monovalent monocyclic group that has at least one heteroatom selected from N, O, P, and S as a ring-forming atom, 1 to 10 carbon atoms, and at least one double bond in its ring. Non-limiting examples of the $C_2$-$C_{10}$ heterocycloalkenyl group include a 2,3-hydrofuranyl group and a 2,3-hydrothiophenyl group. A $C_2$-$C_{10}$ heterocycloalkenylene group as used herein may refer to a divalent group having the same structure as the $C_2$-$C_{10}$ heterocycloalkenyl group.

A $C_6$-$C_{60}$ aryl group as used herein may refer to a monovalent group having a carbocyclic aromatic system having 6 to 60 carbon atoms, and a $C_6$-$C_{60}$ arylene group as used herein may refer to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include two or more rings, the respective rings may be fused to each other.

A $C_1$-$C_{60}$ heteroaryl group as used herein may refer to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein may refer to a divalent group having a carbocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group include two or more rings, the respective rings may be fused to each other.

A $C_6$-$C_{60}$ aryloxy group as used herein may refer to a monovalent group represented by —$OA_{102}$ (wherein $A_{102}$ is the $C_6$-$C_{60}$ aryl group), and a $C_6$-$C_{60}$ arylthio group as used herein may refer to a monovalent group represented by —$SA_{103}$ (wherein $A_{103}$ is the $C_6$-$C_{60}$ aryl group).

A monovalent non-aromatic condensed polycyclic group as used herein may refer to a monovalent group that has two or more rings condensed to each other, has carbon atoms only as ring-forming atoms (e.g., 8 to 60 carbon atoms), and does not have overall aromaticity. A non-limiting example of the monovalent non-aromatic condensed polycyclic group is a fluorenyl group. A divalent non-aromatic condensed polycyclic group as used herein may refer to a divalent group having the same structure as the monovalent non-aromatic condensed polycyclic group.

A monovalent non-aromatic condensed heteropolycyclic group as used herein may refer to a monovalent group that has two or more rings condensed to each other, has at least one heteroatom selected from N, O, P, and S as a ring-forming atom, in addition to carbon atoms (e.g., 2 to 60 carbon atoms), and does not have overall aromaticity. A non-limiting example of the monovalent non-aromatic condensed heteropolycyclic group is a carbazolyl group. A divalent non-aromatic condensed heteropolycyclic group used herein may refer to a divalent group having the same structure as the monovalent non-aromatic condensed heteropolycyclic group.

At least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_1$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{16})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_1$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "Ph" as used herein may refer to a phenyl group, the term "Me" as used herein may refer to a methyl group, the term "Et" as used herein may refer to an ethyl group, and the term "ter-Bu" or "Bu$^t$" as used herein may refer to a tert-butyl group.

Hereinafter an organic light-emitting device according to embodiments of the present disclosure will be described in more detail with reference to Synthesis Examples and Examples.

SYNTHESIS EXAMPLES

Synthesis Example 1: Synthesis of Compound 1

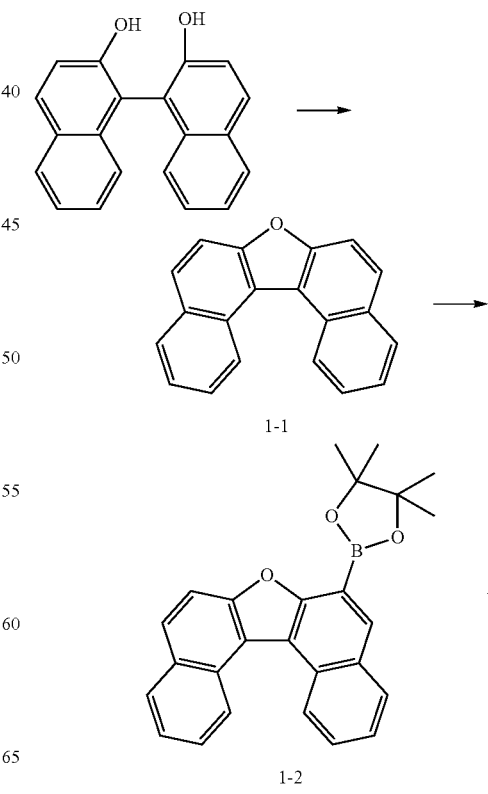

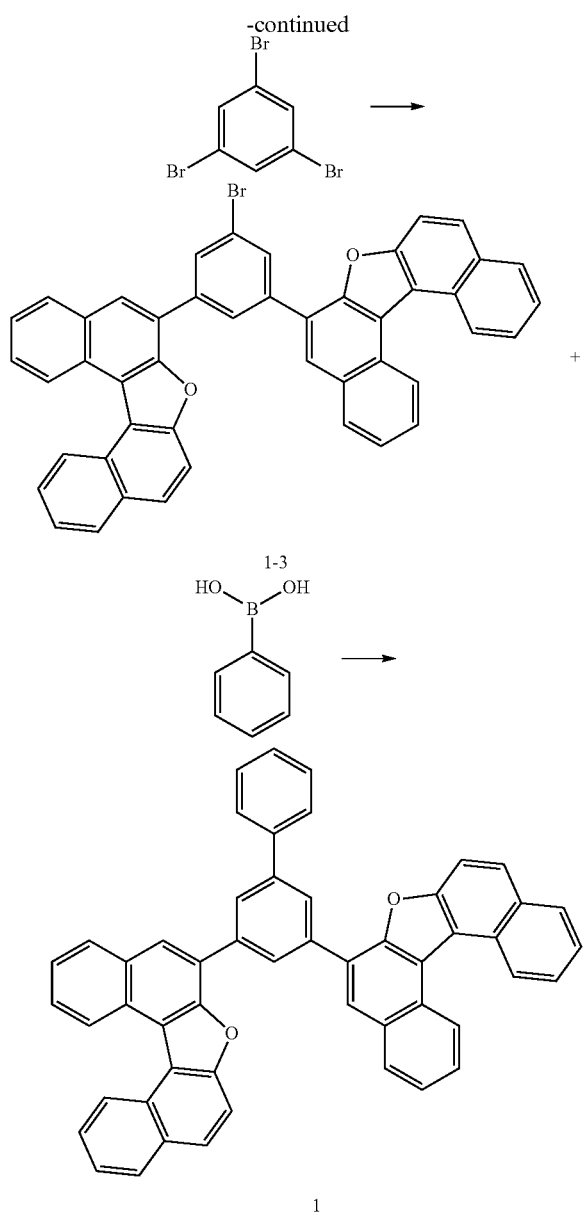

was added thereto at a temperature of −78° C. An hour later, 3.64 mL (18.2 mmol) of 2-isopropoxy-4,4,5,5-tetramethyl-1,3,2-dioxaborolane was added thereto at the same temperature, and then, the mixed solution was stirred at room temperature for 5 hours. Next, water was added thereto and the reaction mixture was extracted three times, each time with 30 mL of diethyl ether. A diethyl ether layer obtained therefrom was dried using MgSO$_4$ and concentrated under a reduced pressure. The resulting product obtained therefrom was separated-purified by silica gel chromatography, so as to obtain 4.97 g (yield: 90%) of Intermediate 1-2. Intermediate 1-2 was identified via LC-MS.

$C_{26}H_{23}BO_3$: M$^+$394.3

Synthesis of Intermediate 1-3

7.88 g (20 mmol) of Intermediate 1-2, 3.15 g (10 mmol) of tribromobenzene, 1.16 g (1 mmol) of Pd(PPh$_3$)$_4$, and 8.28 g (60 mmol) of K$_2$CO$_3$ were dissolved in 120 mL of a THF/H$_2$O solution (mixed at a volume ratio of 2/1), and then, the mixed solution was stirred at a temperature of 80° C. for 16 hours. After the reaction solution was cooled room temperature, the reaction solution was extracted three times, each time with 40 mL of water and 50 mL of ethyl ether. An organic layer obtained therefrom was dried using magnesium sulfate. The residues obtained by evaporating solvents therefrom were separated-purified by silica gel chromatography, so as to obtain 4.14 g (yield: 60%) of Intermediate 1-3. Intermediate 1-3 was identified via LC-MS.

$C_{46}H_{25}BrO_2$: M$^+$688.1

Synthesis of Compound 1

4.97 g (10 mmol) of Intermediate 1-3, 1.22 g (10 mmol) of phenylboronic acid, 0.58 g (0.5 mmol) of Pd(PPh$_3$)$_4$, and 4.14 g (30 mmol) of K$_2$CO$_3$ were dissolved in 80 mL of a THF/H$_2$O solution (mixed at a volume ratio of 2/1), and then, the mixed solution was stirred at a temperature of 80° C. for 12 hours. After the reaction solution was cooled room temperature, the reaction solution was extracted three times, each time with 30 mL of water and 30 mL of ethylacetate. An organic layer obtained therefrom was dried using magnesium sulfate. The residues obtained by evaporating solvents therefrom were separated-purified by silica gel chromatography, so as to obtain 5.49 g (yield: 80%) of Compound 1. Compound 1 was identified via Mass spectrometry/Fast atom bombardment (MS/FAB) and $^1$H NMR.

$C_{52}H_{30}O_2$: M$^+$ cal.: 686.22. found: 686.32.
$^1$H NMR (400 MHz, CDCl$_3$) δ (ppm) 8.86-8.82 (m, 4H), 8.21-8.20 (m, 3H), 8.00 (d, 2H), 7.96 (s, 2H), 7.90 (m, 4H), 7.84-7.69 (m, 8H), 7.47-7.37 (m, 7H)

Synthesis Example 2: Synthesis of Compound 5

Synthesis of Intermediate 1-1

5.73 g (20 mmol) of (1,1'-binaphthalene)-2,2'-diol and 4.10 g (20 mmol) of p-TsOH were dissolved in 150 mL of toluene, and then, the mixed solution was stirred at a temperature of 100° C. for 12 hours. After a resultant product from the stirring was cooled to room temperature, a potassium carbonate solution was added thereto. An organic layer was extracted therefrom using 60 mL of ethylacetate three times, and then, dried using magnesium sulfate. The residues obtained by evaporating solvents therefrom were separated-purified by silica gel chromatography, so as to obtain 3.76 g (yield: 70%) of Intermediate 1-1. Intermediate 1-1 was identified via Liquid chromatography-mass spectrometry (LC-MS).

$C_{20}H_{12}O$: M$^+$268.3

Synthesis of Intermediate 1-2

3.76 g (14 mmol) of Intermediate 1-1 was dissolved in 80 mL of THF, and then, 5.6 mL (2.5M in Hexane) of n-BuLi

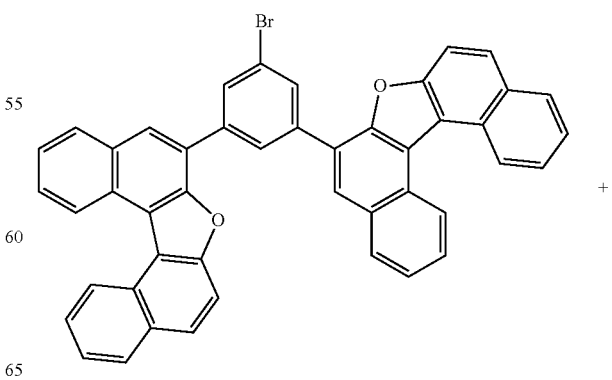

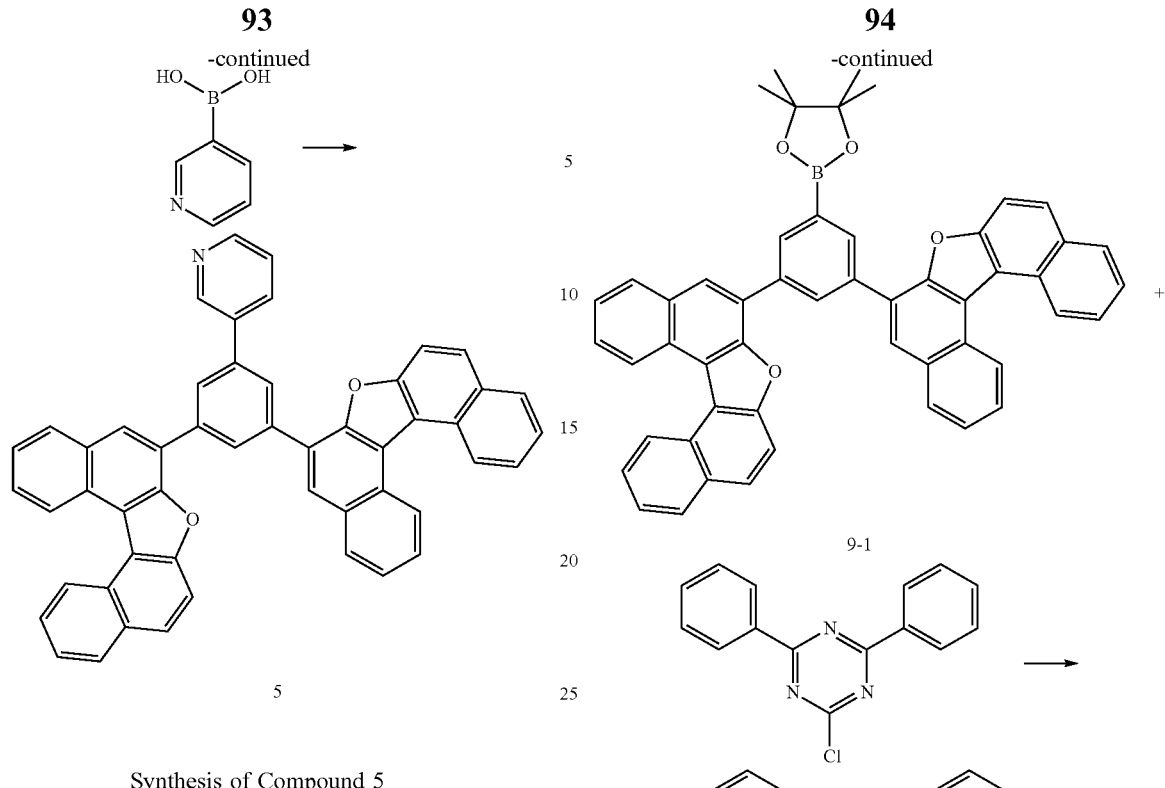

Synthesis of Compound 5

4.97 g (10 mmol) of Intermediate 1-3, 1.23 g (10 mmol) of pyridin-3-yl-boronic acid, 0.58 g (0.5 mmol) of Pd(PPh$_3$)$_4$, and 4.14 g (30 mmol) of K$_2$CO$_3$ were dissolved in 80 mL of a THF/H$_2$O solution (at a volume ratio of 2/1), and then, the mixed solution was stirred at a temperature of 80° C. for 12 hours. After the reaction solution was cooled room temperature, the reaction solution was extracted three times, each wime with 30 mL of water and 30 mL of ethylacetate. An organic layer obtained therefrom was dried using magnesium sulfate. The residues obtained by evaporating solvents therefrom were separated-purified by silica gel chromatography, so as to obtain 5.02 g (yield: 73%) of Compound 5. Compound 5 was identified via MS/FAB and $^1$H NMR.

$C_{51}H_{29}NO_2$: M$^+$ cal.: 687.22. found: 687.32.

$^1$H NMR (400 MHz, CDCl$_3$) δ (ppm) 8.93 (s, 1H), 8.86-8.82 (m, 4H), 8.60 (d, 1H), 8.21 (s, 2H), 8.16 (s, 1H), 8.06 (d, 1H), 8.00 (d, 2H), 7.92-7.72 (m, 12H), 7.46-7.43 (m, 5H)

Synthesis Example 3: Synthesis of Compound 9

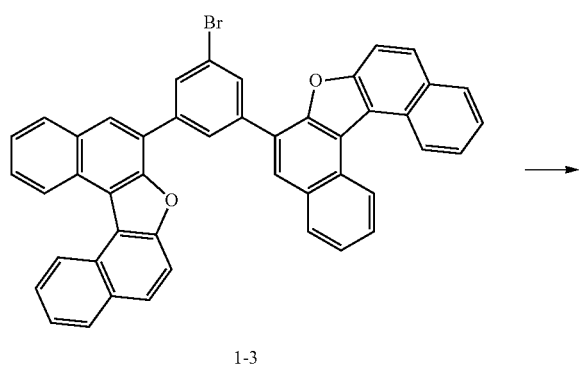

Synthesis of Intermediate 9-1

6.90 g (10 mmol) of Intermediate 1-3 was dissolved in 30 mL of THF, and then, 4 mL of normal butyllithium (n-BuLi) (2.5 M in Hexane) was added thereto at a temperature of −78° C. An hour later, 2.24 ml (11 mmol) of 2-isopropoxy-4,4,5,5-tetramethyl-1,3,2-dioxaborolane was added thereto at the same temperature, and then, the mixed solution was stirred at room temperature for 5 hours. Next, water was added thereto and the reaction mixture was extracted three times, each time with 30 mL of diethyl ether. A diethyl ether layer obtained therefrom was dried using MgSO$_4$ and concentrated under a reduced pressure. The resulting product obtained therefrom was separated-purified by silica gel chromatography, so as to obtain 4.93 g (yield: 67%) of Intermediate 9-1 as white solid. Intermediate 9-1 was identified via LC-MS.

$C_{52}H_{37}BO_4$: M$^+$ 736.5

Synthesis of Compound 9

7.36 g (10 mmol) of Intermediate 9-1, 2.68 g (10 mmol) of 2-chloro-4,6-diphenyl-1,3,5-triazine, 0.58 g (0.5 mmol) of Pd(PPh$_3$)$_4$, and 4.14 g (30 mmol) of K$_2$CO$_3$ were dissolved in 60 mL of a THF/H2O solution (mixed at a volume ratio of 2/1), and then, the mixed solution was stirred at 80° C. temperature for 16 hours. After the reaction solution was cooled room temperature, 40 mL of water was added thereto. The reaction solution was extracted three times, each time with 50 mL of ethyl ether. An organic layer obtained therefrom was dried using magnesium sulfate. The residues obtained by evaporating solvents therefrom were separated-purified by silica gel chromatography, so as to obtain 5.05 g (yield: 60%) of Compound 9. Compound 9 was identified via MS/FAB and $^1$H NMR.

C$_{61}$H$_{35}$N$_3$O$_2$: M$^+$ cal.: 841.27. found: 841.37.

$^1$H NMR (400 MHz, CDCl$_3$) δ (ppm) 8.86-8.78 (m, 8H), 8.70 (s, 2H), 8.38 (s, 2H), 8.17 (s, 1H), 8.00 (d, 2H), 7.92-7.72 (m, 10H), 7.55-7.41 (m, 10H)

Synthesis Example 4: Synthesis of Compound 14

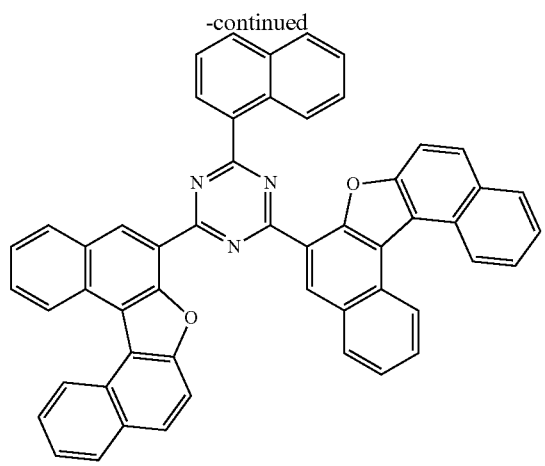

14

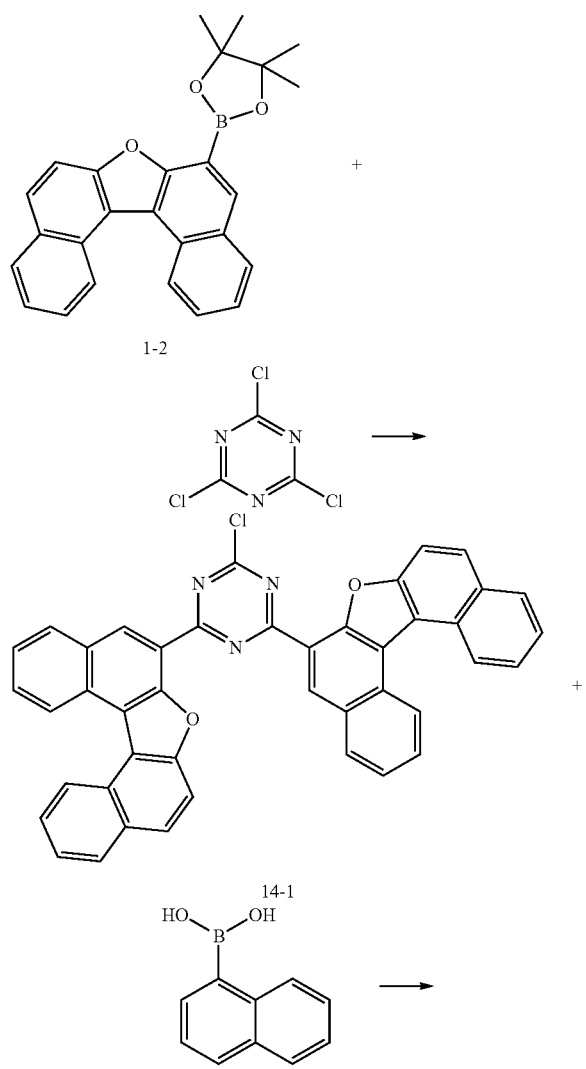

Synthesis of Intermediate 14-1

7.88 g (20 mmol) of Intermediate 1-2, 1.84 g (10 mmol) of cyanuric chloride, 1.16 g (1 mmol) of Pd(PPh$_3$)$_4$, and 8.28 g (60 mmol) of K$_2$CO$_3$ were dissolved in 120 mL of a THF/H$_2$O solution (at a volume ratio of 2/1), and then, the mixed solution was stirred at a temperature of 80° C. for 16 hours. After the reaction solution was cooled room temperature, 40 mL of water was added thereto. The reaction solution was extracted three times, each time with 50 mL of ethyl ether. An organic layer obtained therefrom was dried using magnesium sulfate. The residues obtained by evaporating solvents therefrom were separated-purified by silica gel chromatography, so as to obtain 3.37 g (yield: 52%) of Intermediate 14-1. Intermediate 14-1 was identified via LC-MS.

C$_{43}$H$_{22}$ClN$_3$O$_2$: M$^+$ 647.3

Synthesis of Compound 14

6.48 g (10 mmol) of Intermediate 14-1, 1.72 g (10 mmol) of 1-naphthylboronic acid, 0.58 g (0.5 mmol) of Pd(PPh$_3$)$_4$, and 4.14 g (30 mmol) of K$_2$CO$_3$ were dissolved in 80 mL of a THF/H$_2$O solution (mixed at a volume ratio of 2/1), and then, the mixed solution was stirred at a temperature of 80° C. for 16 hours. After the reaction solution was cooled room temperature, the reaction solution was extracted three times, each time with 30 mL of water and 30 mL of ethyl ether. An organic layer obtained therefrom was dried using magnesium sulfate. The residues obtained by evaporating solvents therefrom were separated-purified by silica gel chromatography, so as to obtain 5.47 g (yield: 74%) of Compound 14. Compound 14 was identified via MS/FAB and $^1$H NMR.

C$_{53}$H$_{29}$N$_3$O$_2$: M$^+$ cal.: 739.23. found: 739.33.

$^1$H NMR (400 MHz, CDCl$_3$) δ (ppm) 9.39 (s, 2H), 8.99 (d, 2H), 8.85 (d, 2H), 8.69 (d, 1H), 8.24-7.78 (m, 15H), 7.68-7.43 (m, 7H)

Synthesis Example 5: Synthesis of Compound 21

Synthesis Example 6: Synthesis of Compound 23

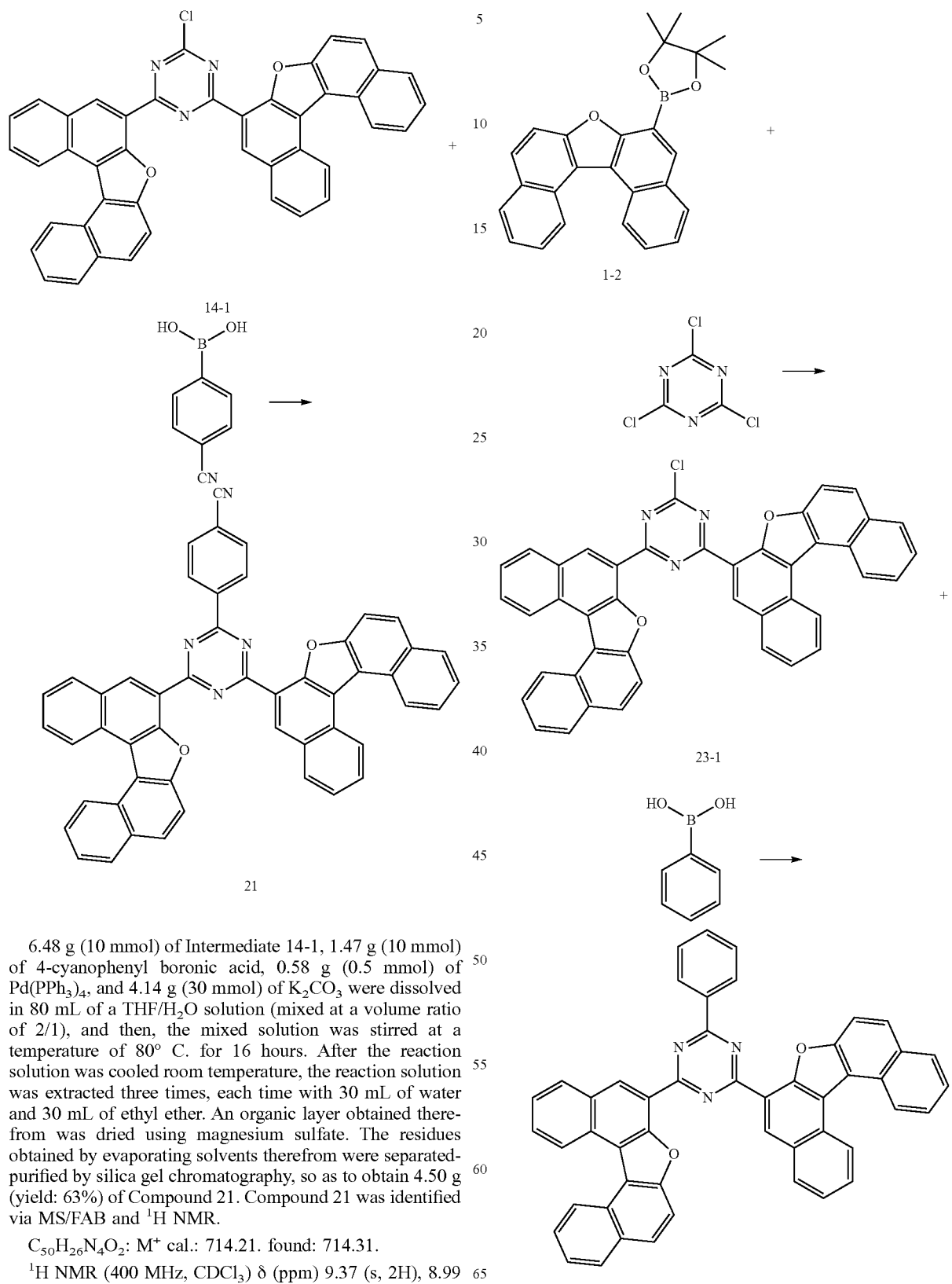

6.48 g (10 mmol) of Intermediate 14-1, 1.47 g (10 mmol) of 4-cyanophenyl boronic acid, 0.58 g (0.5 mmol) of Pd(PPh$_3$)$_4$, and 4.14 g (30 mmol) of K$_2$CO$_3$ were dissolved in 80 mL of a THF/H$_2$O solution (mixed at a volume ratio of 2/1), and then, the mixed solution was stirred at a temperature of 80° C. for 16 hours. After the reaction solution was cooled room temperature, the reaction solution was extracted three times, each time with 30 mL of water and 30 mL of ethyl ether. An organic layer obtained therefrom was dried using magnesium sulfate. The residues obtained by evaporating solvents therefrom were separated-purified by silica gel chromatography, so as to obtain 4.50 g (yield: 63%) of Compound 21. Compound 21 was identified via MS/FAB and $^1$H NMR.

C$_{50}$H$_{26}$N$_4$O$_2$: M$^+$ cal.: 714.21. found: 714.31.

$^1$H NMR (400 MHz, CDCl$_3$) δ (ppm) 9.37 (s, 2H), 8.99 (d, 2H), 8.85 (d, 2H), 8.61 (d, 2H), 8.21 (d, 2H), 7.92-7.78 (m, 12H), 7.57-7.43 (m, 4H)

Synthesis of Intermediate 23-1

7.88 g (20 mmol) of Intermediate 1-2, 1.83 g (10 mmol) of 2,4,6-trichloropyrimidine, 1.16 g (1 mmol) of Pd(PPh$_3$)$_4$, and 8.28 g (60 mmol) of K$_2$CO$_3$ were dissolved in 120 mL of a THF/H$_2$O solution (mixed at a volume ratio of 2/1), and then, the mixed solution was stirred at a temperature of 80° C. for 16 hours. After the reaction solution was cooled room temperature, 40 mL of water was added thereto. The reaction solution was extracted three times, each time with 50 mL of ethyl ether. An organic layer obtained therefrom was dried using magnesium sulfate. The residues obtained by evaporating solvents therefrom were separated-purified by silica gel chromatography, so as to obtain 2.91 g (yield: 45%) of Intermediate 23-1. Intermediate 23-1 was identified via LC-MS.

C$_{44}$H$_{23}$ClN$_2$O$_2$: M$^+$ 646.3

Synthesis of Compound 23

6.48 g (10 mmol) of Intermediate 23-1, 1.72 g (10 mmol) of phenylboronic acid, 0.58 g (0.5 mmol) of Pd(PPh$_3$)$_4$, and 4.14 g (30 mmol) of K$_2$CO$_3$ were dissolved in 80 mL of a THF/H$_2$O solution (mixed at a volume ratio of 2/1), and then, the mixed solution was stirred at a temperature of 80° C. for 12 hours. After the reaction solution was cooled room temperature, the reaction solution was extracted three times, each time with 30 mL of water and 30 mL of ethyl ether. An organic layer obtained therefrom was dried using magnesium sulfate. The residues obtained by evaporating solvents therefrom were separated-purified by silica gel chromatography, so as to obtain 4.82 g (yield: 70%) of Compound 23. Compound 23 was identified via MS/FAB and $^1$H NMR.

C$_{50}$H$_{28}$N$_2$O$_2$: M$^+$ cal.: 688.22. found: 688.32.

$^1$H NMR (400 MHz, CDCl$_3$) δ (ppm) 9.02 (s, 2H), 8.91 (d, 2H), 8.85 (d, 2H), 8.62-8.54 (m, 2H), 8.10-8.08 (m, 3H), 7.92-7.76 (m, 10H), 7.55-7.43 (m, 7H)

Synthesis Example 7: Synthesis of Compound 35

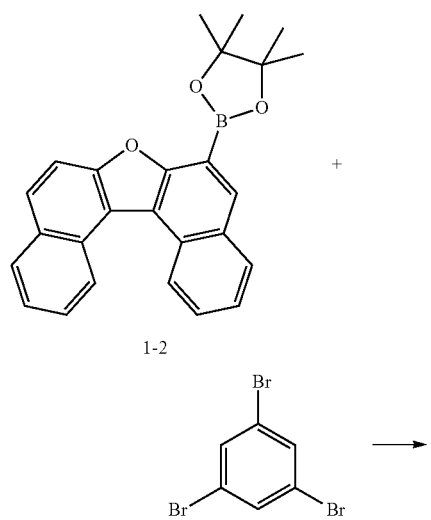

1-2

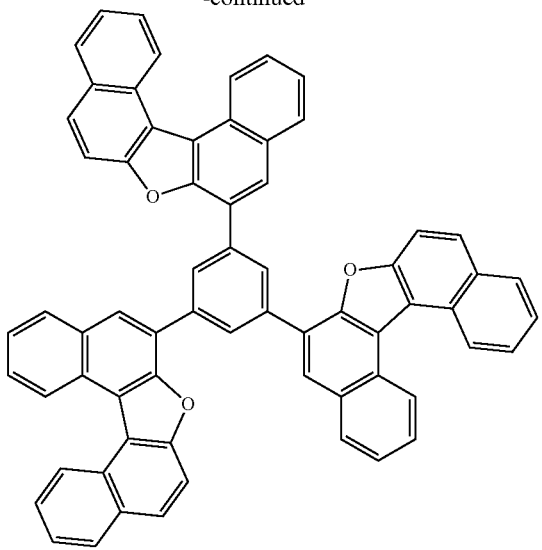

35

11.82 g (30 mmol) of Intermediate 1-2, 3.15 g (10 mmol) of tribromobenzene, 1.74 g (1.5 mmol) of Pd(PPh$_3$)$_4$, and 12.42 g (90 mmol) of K$_2$CO$_3$ were dissolved in 120 mL of a THF/H$_2$O solution (at a volume ratio of 2/1), and then, the mixed solution was stirred at a temperature of 80° C. for 16 hours. After the reaction solution was cooled room temperature, 40 mL of water was added thereto. The reaction solution was extracted three times, each time with 50 mL of ethyl ether. An organic layer obtained therefrom was dried using magnesium sulfate. The residues obtained by evaporating solvents therefrom were separated-purified by silica gel chromatography, so as to obtain 5.26 g (yield: 60%) of Intermediate 35. Intermediate 35 was identified via MS/FAB and $^1$H NMR.

C$_{66}$H$_{36}$O$_3$: M$^+$ cal.: 876.27. found: 876.37.

$^1$H NMR (400 MHz, CDCl$_3$) δ (ppm) 8.86-8.82 (m, 6H), 8.24 (s, 3H), 8.00 (d, 3H), 7.93-7.72 (m, 18H), 7.47-7.43 (m, 6H)

Synthesis Example 8: Synthesis of Compound 40

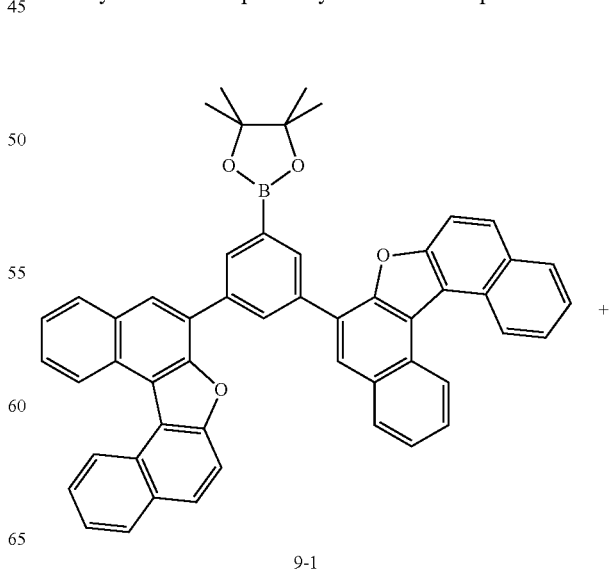

9-1

-continued

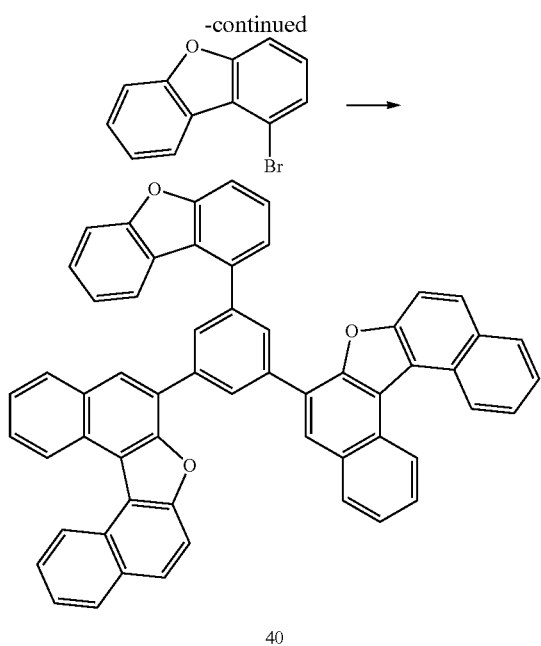

40

7.36 g (10 mmol) of Intermediate 9-1, 2.47 g (10 mmol) of 1-bromodibenzofuran, 0.58 g (0.5 mmol) of Pd(PPh$_3$)$_4$, and 4.14 g (30 mmol) of K$_2$CO$_3$ were dissolved in 60 mL of a THF/H$_2$O solution (mixed at a volume ratio of 2/1), and then, the mixed solution was stirred at a temperature of 80° C. for 16 hours. After the reaction solution was cooled room temperature, 40 mL of water was added thereto. The reaction solution was extracted three times, each time with 50 mL of ethyl ether. An organic layer obtained therefrom was dried using magnesium sulfate. The residues obtained by evaporating solvents therefrom were separated-purified by silica gel chromatography, so as to obtain 5.05 g (yield: 65%) of Compound 40. Compound 40 was identified via MS/FAB and $^1$H NMR.

C$_{58}$H$_{32}$O$_3$: M$^+$ cal.: 776.24. found: 776.34.

$^1$H NMR (400 MHz, CDCl$_3$) δ (ppm) 8.86-8.82 (m, 4H), 8.24 (s, 2H), 8.14-8.11 (m, 3H), 8.00 (d, 2H), 7.92-7.72 (m, 11H), 7.60-7.42 (m, 10H)

EXAMPLES

Example 1

A 15 Ω/cm$^2$ (1,200 Å) ITO glass substrate (manufactured by Corning, Inc.) was cut into a size of 50 mm×50 mm×0.7 mm and ultrasonically washed out with isopropyl alcohol and pure water, each for 5 minutes. The resulting ITO glass substrate was irradiated by UV for 30 minutes, cleaned by exposing to ozone, and then, transported to a vacuum evaporator.

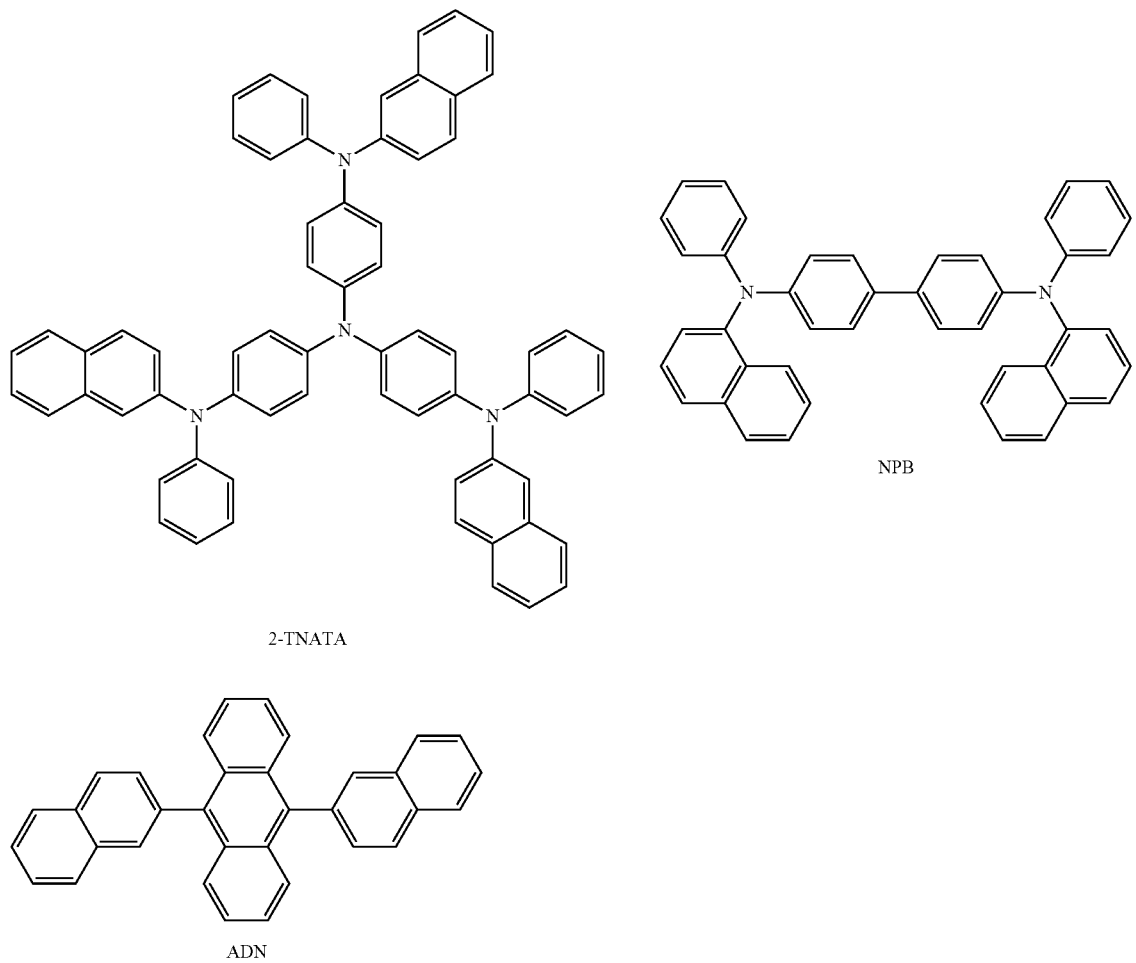

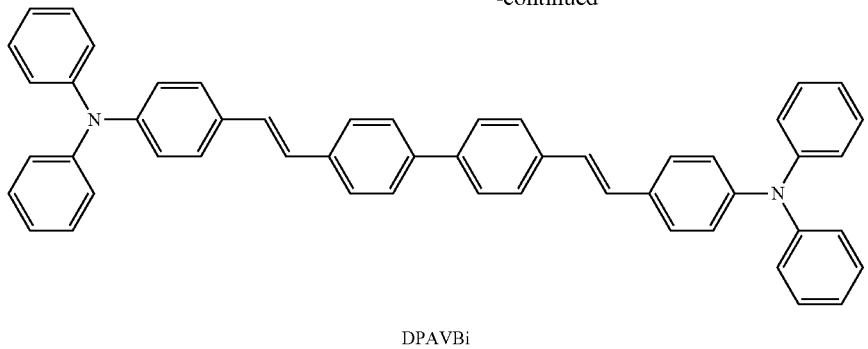

DPAVBi

2-TNATA was vacuum deposited on the ITO anode to form an HIL having a thickness of 600 Å. Next, 4,4'-bis[N-(1-naphthyl)-N-phenylamino]biphenyl (hereinafter, referred to as NPB), as a hole transporting compound, was vacuum deposited on the HIL to form an HTL having a thickness of 300 Å. Then, 9,10-di-naphthalene-2-yl-anthracene (hereinafter, referred to as ADN), as a blue fluorescent host, and 4,4'-bis[2-(4-(N,N-diphenylamino)phenyl)vinyl]biphenyl (hereinafter, referred to as DPAVBi), as a blue fluorescent dopant, were co-deposited at a weight ratio of 98:2 on the HTL to form an emission layer having a thickness of 300 Å.

Then, Compound 1 was deposited on the emission layer to form an ETL having a thickness of 300 Å, and LiF, as a halogenated alkali metal, was deposited on the ETL to form an EIL having a thickness of 10 Å. Al was deposited on the EIL to form a cathode (i.e., a LiF/Al electrode) having a thickness of 3,000 Å, thereby manufacturing an organic light-emitting device.

The organic light-emitting device of Example 1 exhibited a driving voltage of 5.80 V at a current density of 50 mA/cm$^2$, a light-emitting brightness of 3,050 cd/m$^2$, a light-emitting efficiency of 6.10 cd/A, and a half-lifespan (hr @100 mA/cm$^2$) of 322 hours.

Example 2

An organic light-emitting device was manufactured in the same (or substantially the same) manner as in Example 1, except that in forming the ETL, Compound 5 was used instead of Compound 1.

Example 3

An organic light-emitting device was manufactured in the same (or substantially the same) manner as in Example 1, except that in forming the ETL, Compound 9 was used instead of Compound 1.

Example 4

An organic light-emitting device was manufactured in the same (or substantially the same) manner as in Example 1, except that in forming the ETL, Compound 14 was used instead of Compound 1.

Example 5

An organic light-emitting device was manufactured in the same (or substantially the same) manner as in Example 1, except that in forming the ETL, Compound 21 was used instead of Compound 1.

Example 6

An organic light-emitting device was manufactured in the same (or substantially the same) manner as in Example 1, except that in forming the ETL, Compound 23 was used instead of Compound 1.

Example 7

An organic light-emitting device was manufactured in the same (or substantially the same) manner as in Example 1, except that in forming the ETL, Compound 35 was used instead of Compound 1.

Example 8

An organic light-emitting device was manufactured in the same (or substantially the same) manner as in Example 1, except that in forming the ETL, Compound 40 was used instead of Compound 1.

Comparative Example 1

An organic light-emitting device was manufactured in the same (or substantially the same) manner as in Example 1, except that in forming the ETL, Alq$_3$ was used instead of Compound 1.

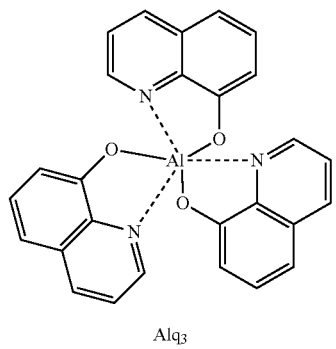

Alq$_3$

The organic light-emitting device prepared in Comparative Example 1 exhibited a driving voltage of 7.35 V at a current density of 50 mA/cm$^2$, a light-emitting brightness of 2,065 cd/m$^2$, a light-emitting efficiency of 4.13 cd/A, and a half-lifespan (hr @100 mA/cm$^2$) of 145 hours.

Comparative Example 2

An organic light-emitting device was manufactured in the same (or substantially the same) manner as in Example 1, except that in forming the ETL, Compound 100 was used instead of Compound 1.

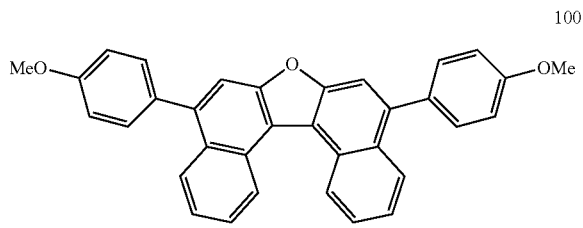 [SMILES: COc1ccc(-c2cc3oc4cc(-c5ccc(OC)cc5)c5ccccc5c4c3c3ccccc23)cc1]

The results and representative characteristics of the organic light-emitting devices prepared in Examples and Comparative Examples above are summarized in Table 1. As shown in Table 1, organic light-emitting devices including the compound of Formula 1 according to the above embodiments as the electron transporting material exhibited a driving voltage that was lower by 1 V or greater than that of the organic light-emitting device of Comparative Example 1, and showed significantly improved current-voltage-luminance (I-V-L) characteristics and excellent life span characteristics, as compared to those of the organic light-emitting devices including $Alq_3$ or Compound 100. Therefore, it is believed that the compound of Formula 1 had excellent characteristics and was suitable for use as the electron transport material.

TABLE 1

| | Material | Driving voltage (V) | Current density (mA/cm$^2$) | Brightness (cd/m$^2$) | Efficiency (cd/A) | Light emission color | Half-lifespan (hr@ 100 mA/cm$^2$) |
|---|---|---|---|---|---|---|---|
| Example 1 | Compound 1 | 5.80 | 50 | 3,050 | 6.10 | Blue | 322 |
| Example 2 | Compound 5 | 5.52 | 50 | 2,950 | 5.90 | Blue | 365 |
| Example 3 | Compound 9 | 5.74 | 50 | 3,190 | 6.38 | Blue | 310 |
| Example 4 | Compound 14 | 5.32 | 50 | 2,925 | 5.85 | Blue | 320 |
| Example 5 | Compound 21 | 5.36 | 50 | 3025 | 6.05 | Blue | 350 |
| Example 6 | Compound 23 | 5.55 | 50 | 3115 | 6.23 | Blue | 295 |
| Example 7 | Compound 35 | 5.95 | 50 | 3075 | 6.15 | Blue | 315 |
| Example 8 | Compound 40 | 5.67 | 50 | 3025 | 6.05 | Blue | 305 |
| Comparative Example 1 | Alq$_3$ | 7.35 | 50 | 2,065 | 4.13 | Blue | 145 |
| Comparative Example 2 | Compound 100 | 6.25 | 50 | 2,725 | 5.45 | Blue | 246 |

As described above, an organic light-emitting device including a compound represented by Formula 1 according to the one or more of the above embodiments may have excellent electron transporting capability and material stability, thereby being suitable as the electron transporting material. Thus, the organic light-emitting device including the compound of Formula 1 may have high efficiency, low driving voltage, high brightness, and long lifespan characteristics.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the drawing, it will be understood by those of ordinary skill in the art that various changes in form and details may be made therein without departing from the spirit and scope of the present disclosure as defined by the following claims and equivalents thereof.

What is claimed is:

1. A compound represented by Formula 1:

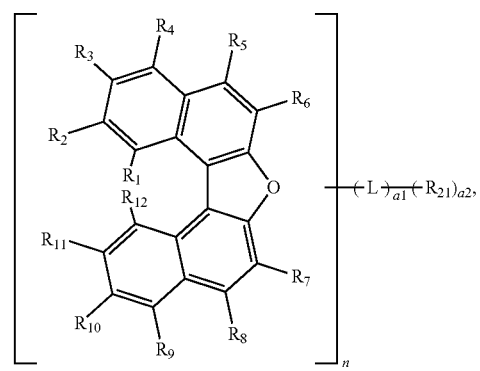

Formula 1 wherein, in Formula 1, $R_1$ to $R_{12}$ are each independently selected from a bond, hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{21}$ is selected from a halogen, a cyano group, a group represented by one of Formulae 3a to 3h:

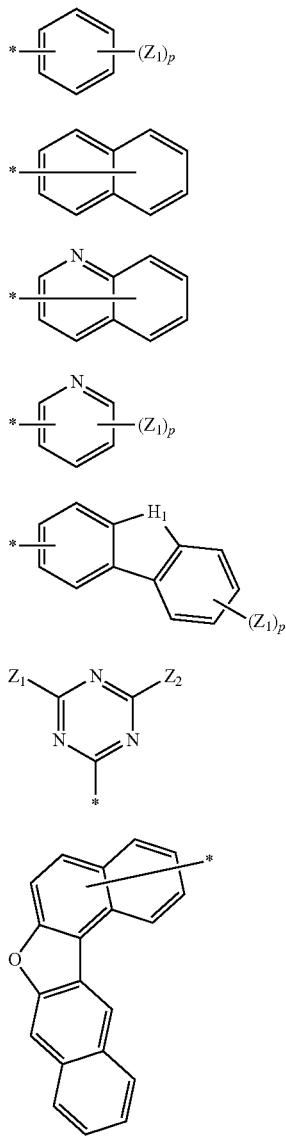

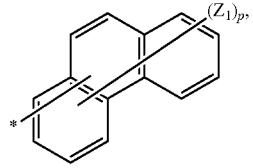

wherein, in Formulae 3a to 3h, $H_1$ is selected from $NR_{31}$, $CR_{32}R_{33}$, O, and S, $R_{31}$ to $R_{33}$, $Z_1$ and $Z_2$ are each independently selected from hydrogen, deuterium, a cyano group, a substituted or unsubstituted carbon $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p in Formula 3a is an integer selected from 1 to 5, p in Formulae 3d and 3e is an integer selected from 1 to 4, and p in Formula 3h is an integer selected from 1 to 9, and

* is a binding site to a neighboring atom,

L is selected from an unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n is an integer selected from 2 to 4, a1 and a2 are each independently an integer selected from 0 to 3, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, and $-B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, and $-B(Q_{26})(Q_{27})$, wherein $Q_{11}$ to $Q_{17}$ and $Q_{21}$ to $Q_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, wherein n number of

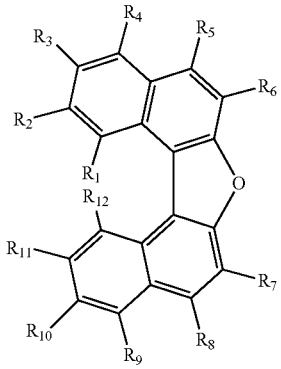

ligands are directly bonded to the L.

2. The compound of claim 1, wherein $R_1$ to $R_5$ and $R_7$ to $R_{12}$ are each independently hydrogen or deuterium, and $R_6$ is a bond, or wherein $R_1$ to $R_6$ and $R_8$ to $R_{12}$ are each independently hydrogen or deuterium, and $R_7$ is a bond.

3. The compound of claim 1, wherein $R_1$ to $R_4$ and $R_6$ to $R_{12}$ are each independently hydrogen or deuterium, and $R_5$ is a bond; or wherein $R_1$ to $R_7$ and $R_9$ to $R_{12}$ are each independently hydrogen or deuterium, and $R_8$ is a bond.

4. The compound of claim 1, wherein L is a substituted or unsubstituted $C_6$-$C_{60}$ arylene group or a substituted or unsubstituted $C_1$-$C_{60}$ heteroarylene group.

5. The compound of claim 1, wherein L is a group represented by one Formulae 2a to 2c:

2a

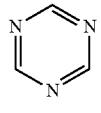

2b

2c

6. The compound of claim 1, wherein n is 2 or 3.

7. The compound of claim 1, wherein the compound represented by Formula 1 is represented by one of Formulae 2, 3, or 4:

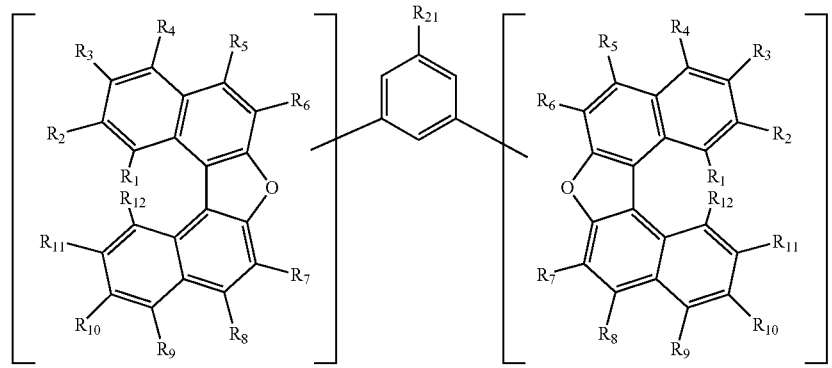

Formula 2

-continued
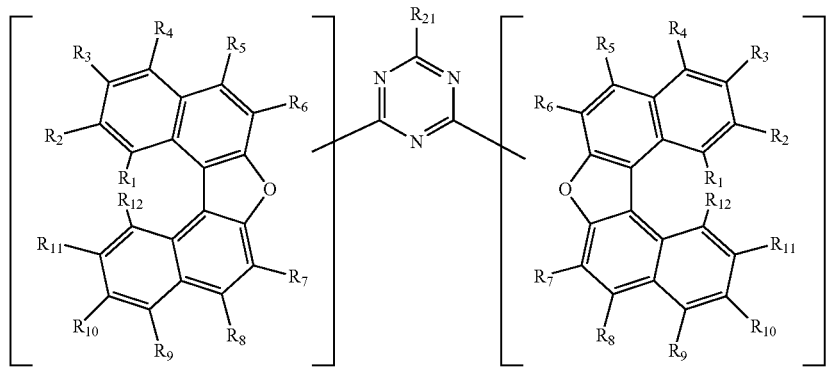
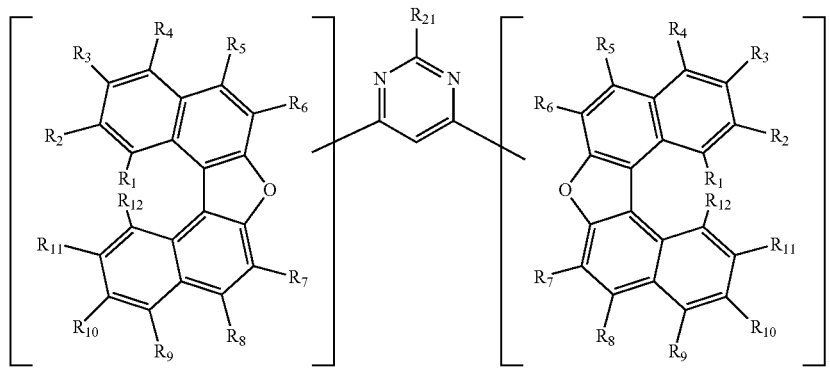
8. The compound of claim 1, wherein the compound represented by Formula 1 is represented by one of Formulae 5, 6, or 7:
Formula 5
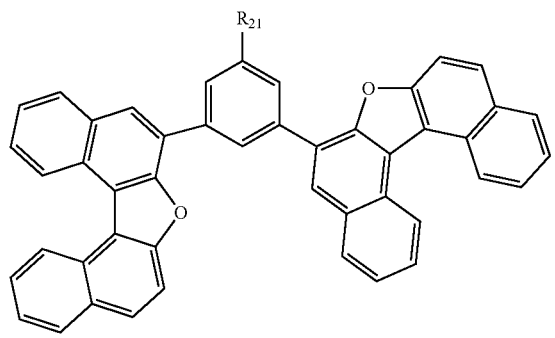
Formula 6
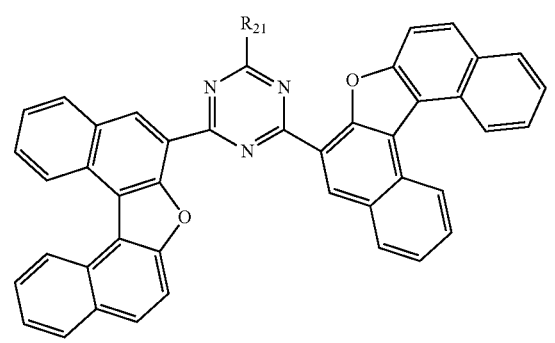
-continued
Formula 7
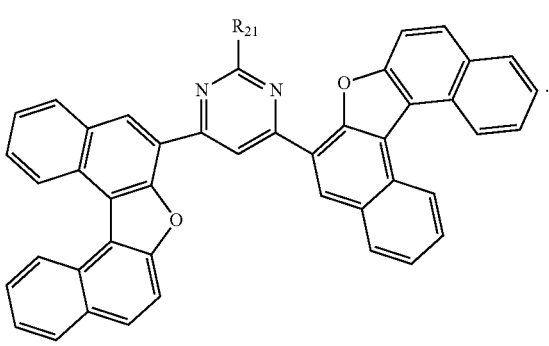
9. The compound of claim 1, wherein the compound represented by Formula 1 is one of the following Compounds 1 to 70:

1
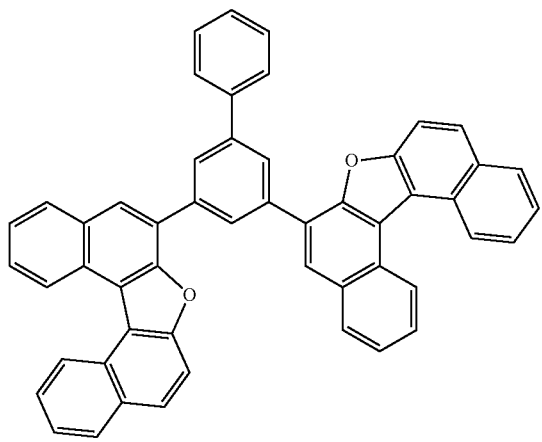
2
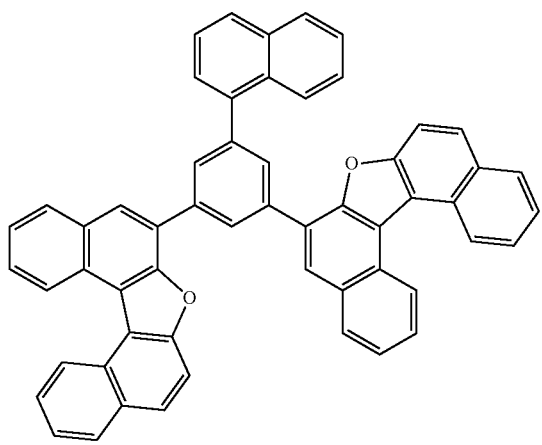
3
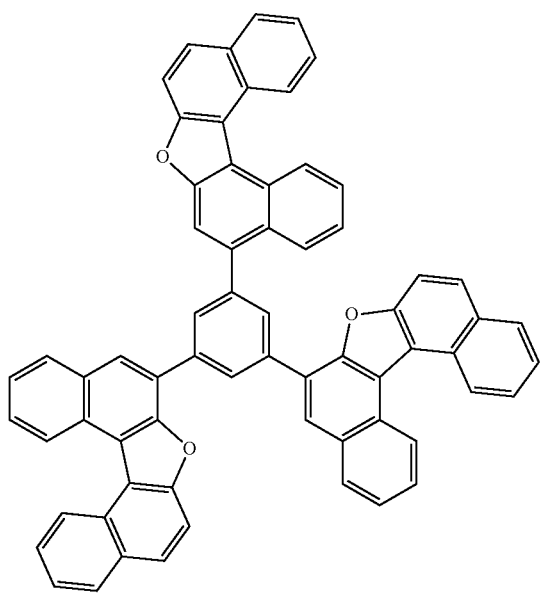
4
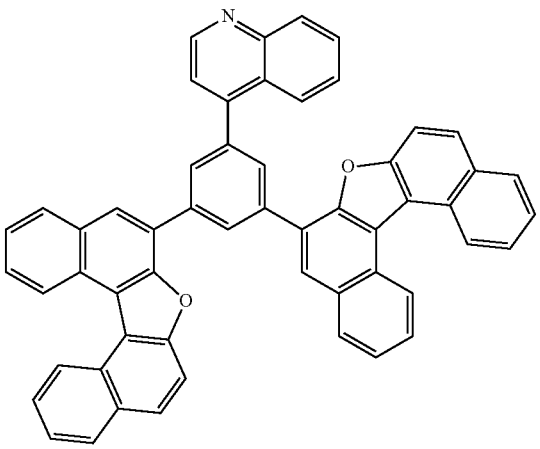
5
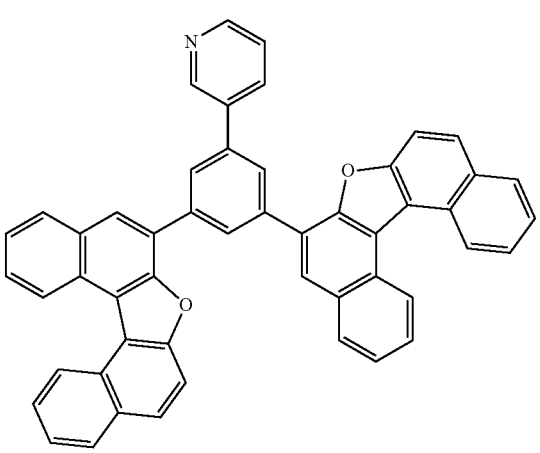
6
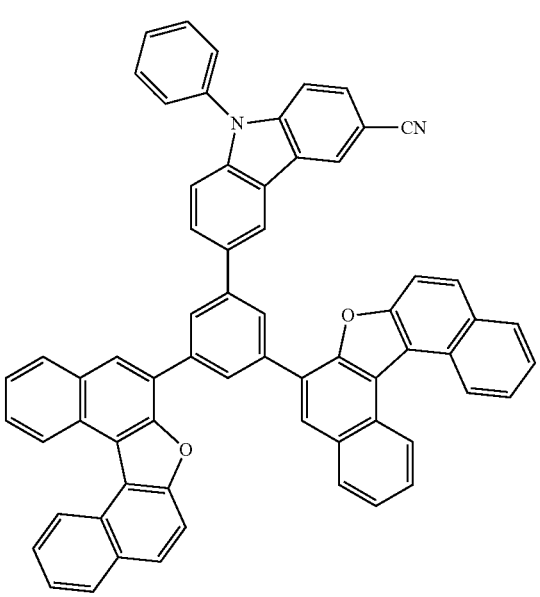

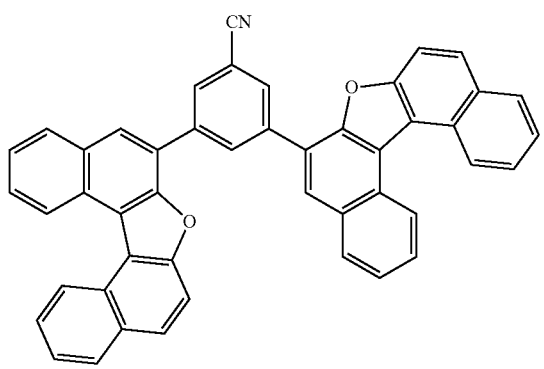
7
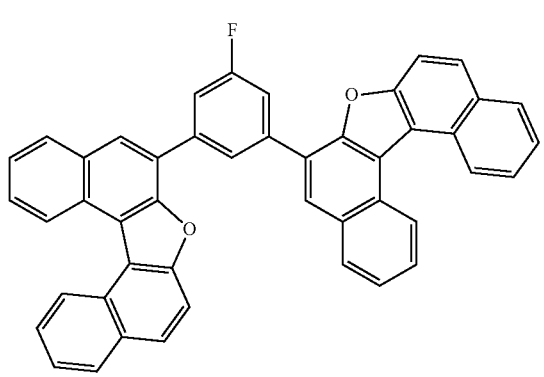
8
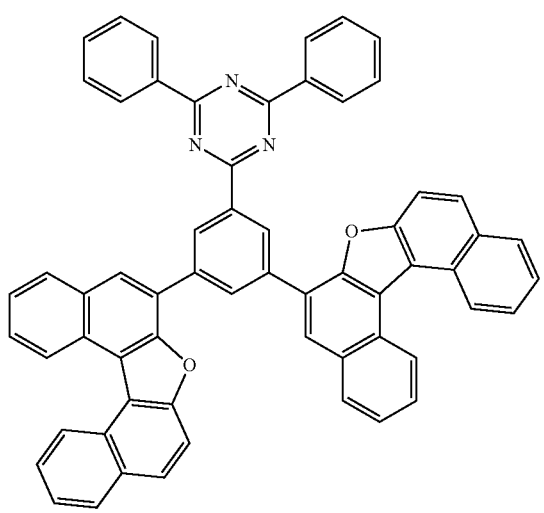
9
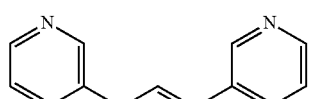
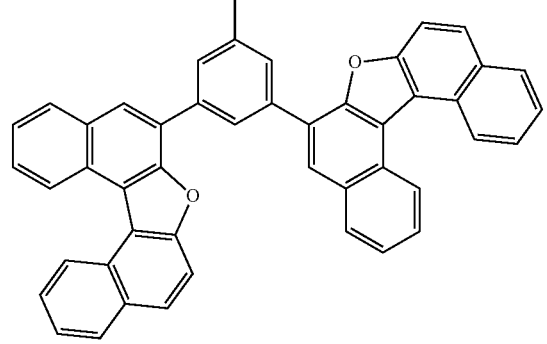
10
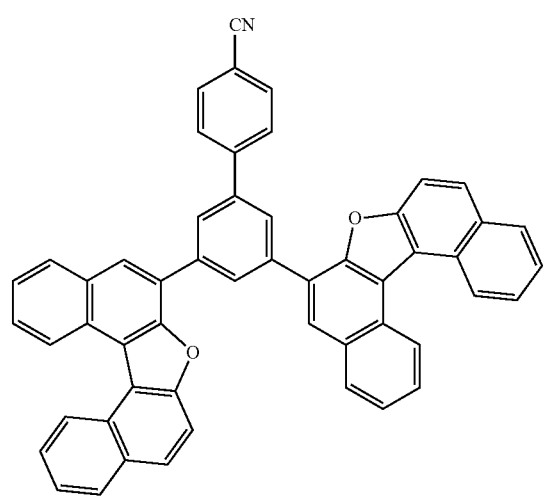
11
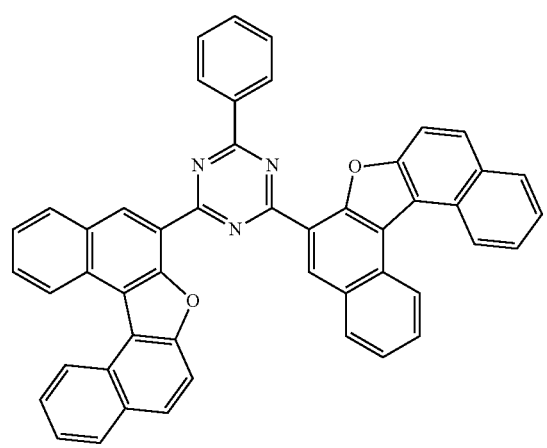
12

13
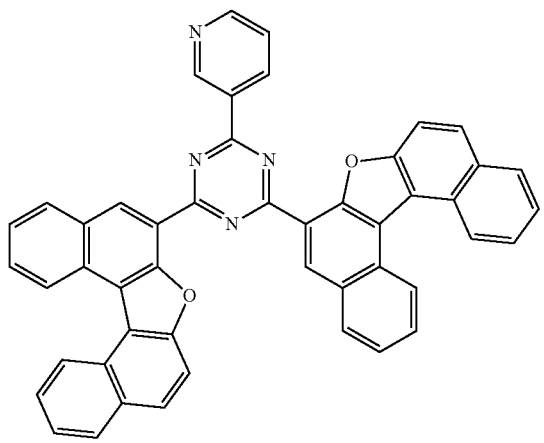
14
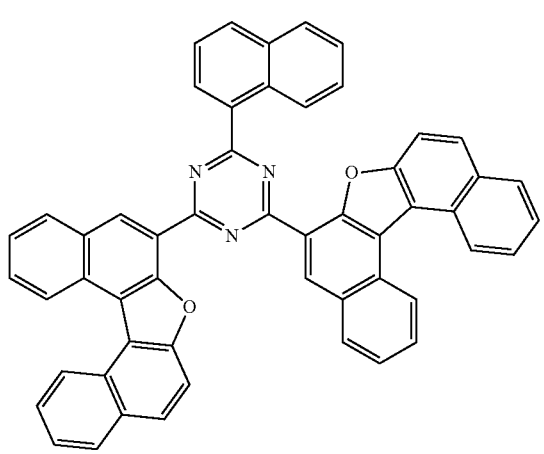
15
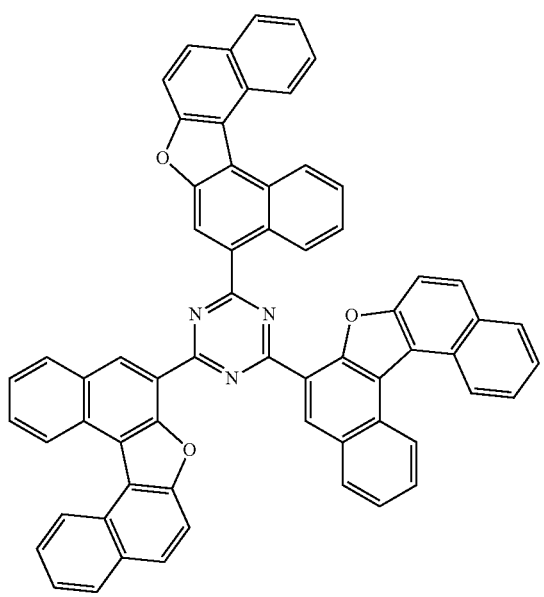
16
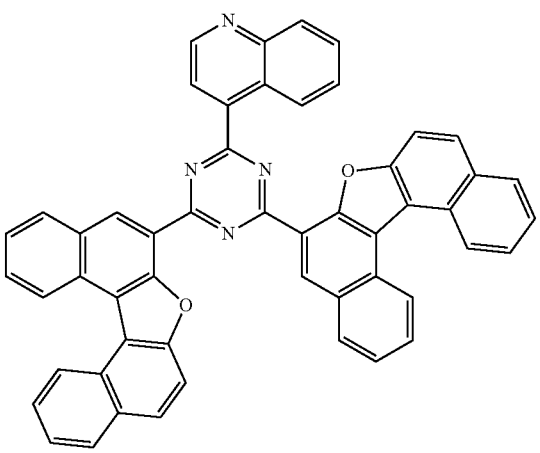
17
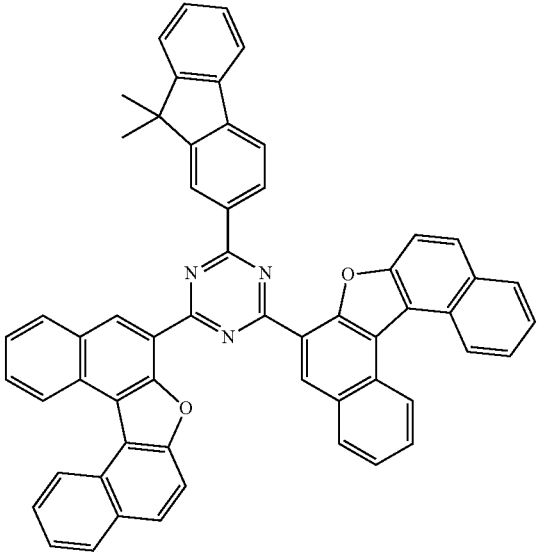
18
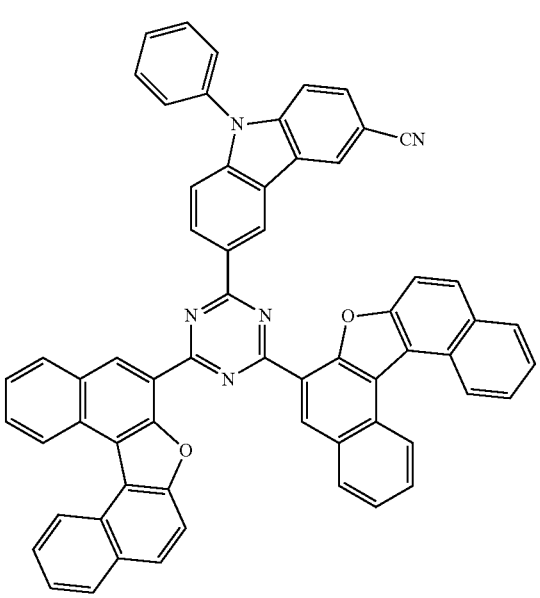

119
-continued
19
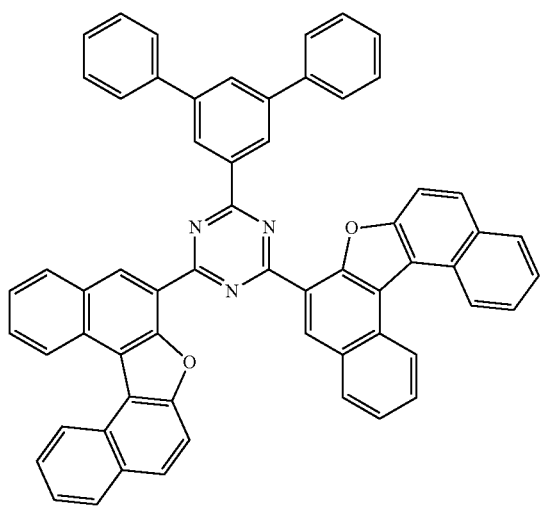
20
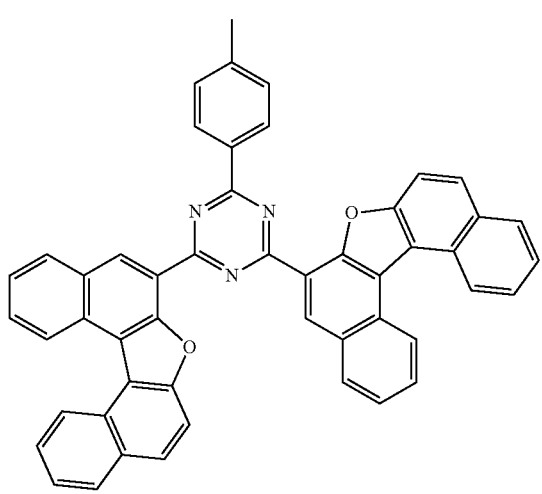
21
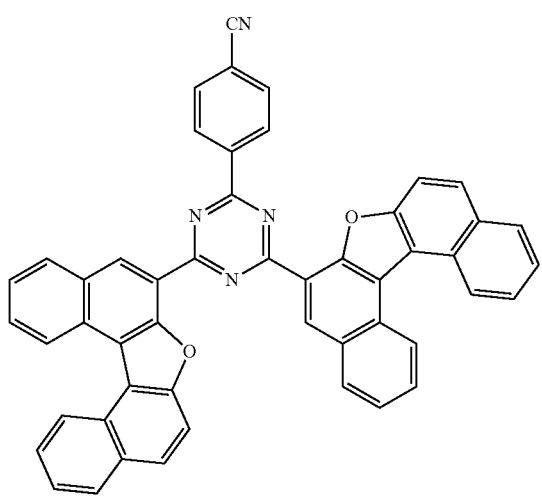
120
-continued
22
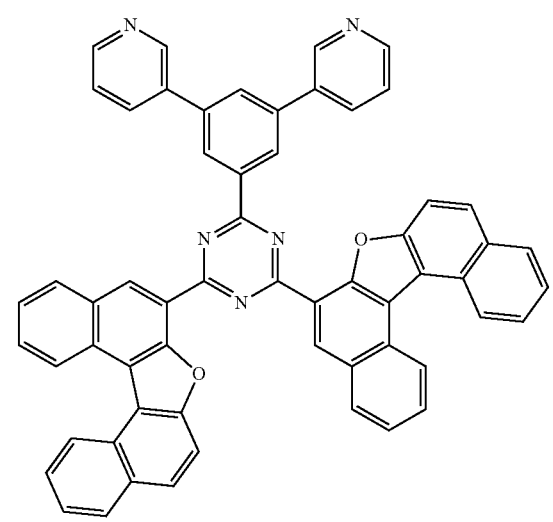
23
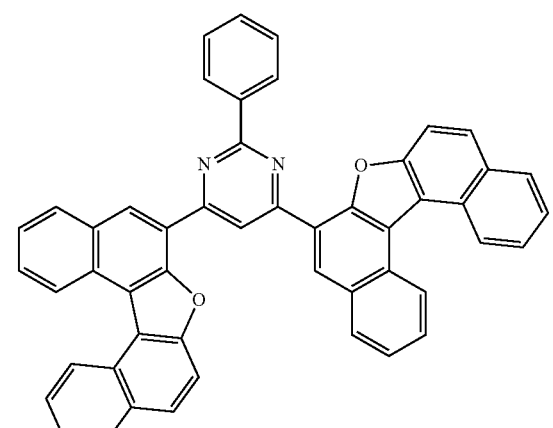
24
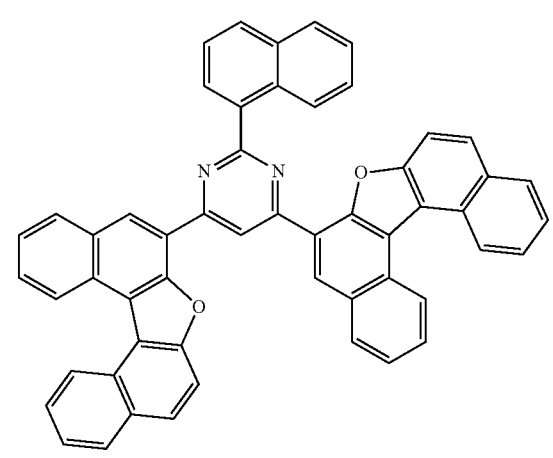

121
-continued
25
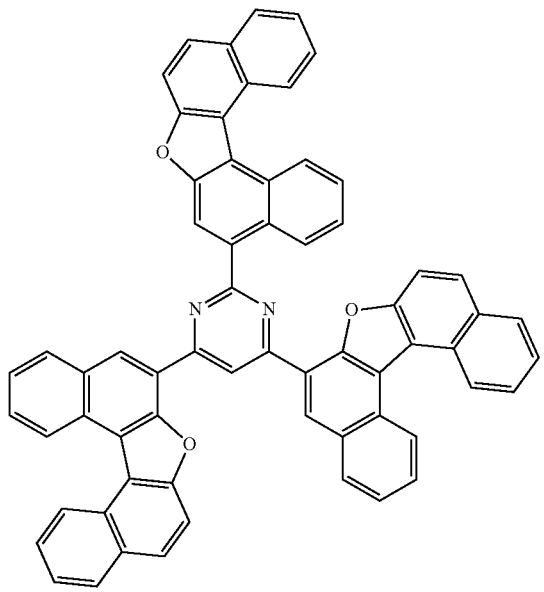
26
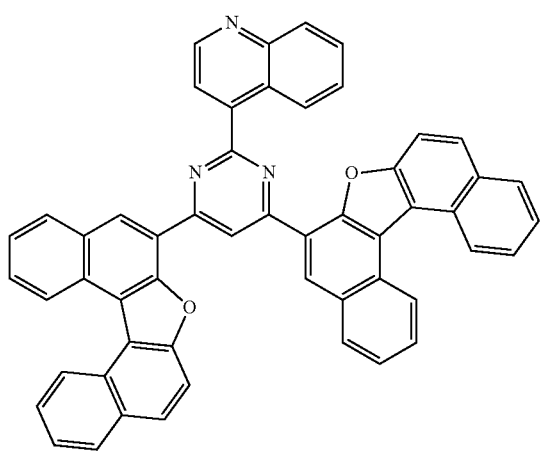
27
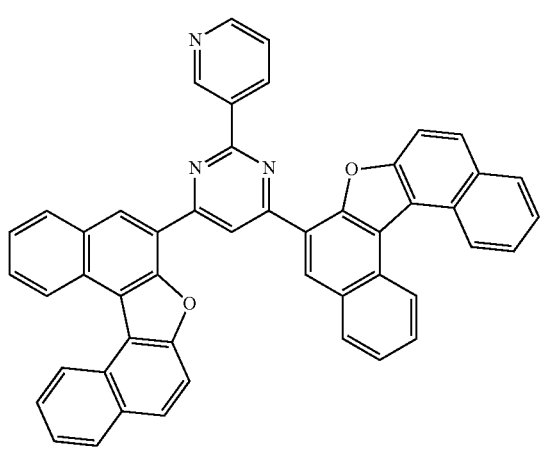
122
-continued
28
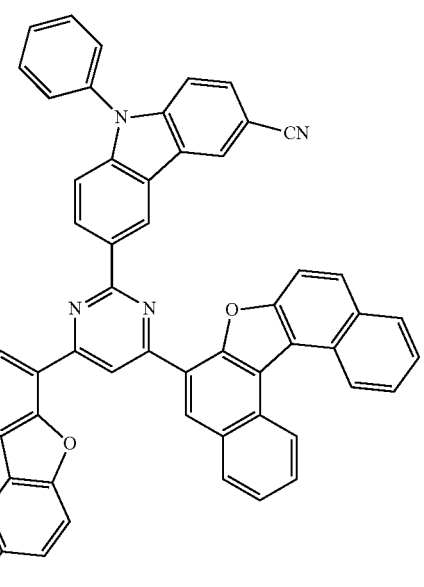
29
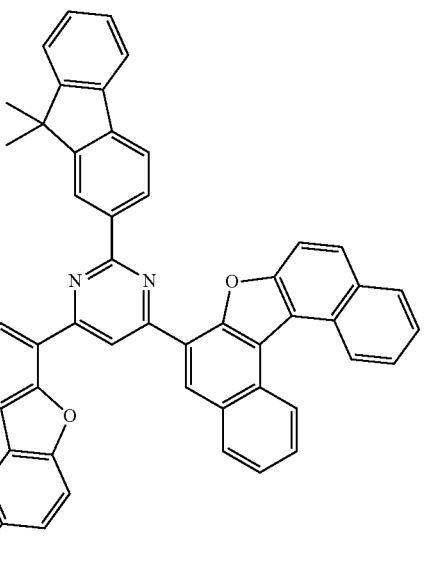

123
-continued
30
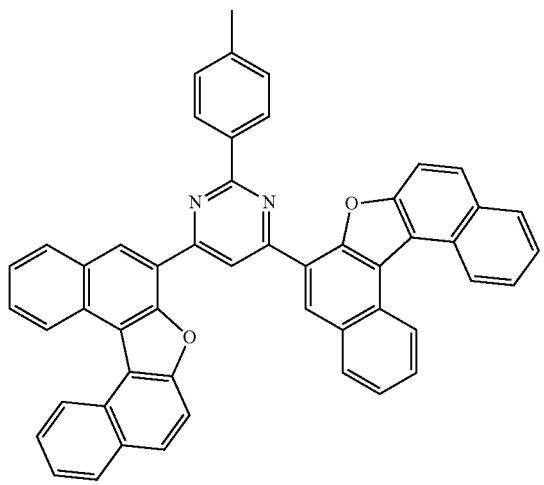
31
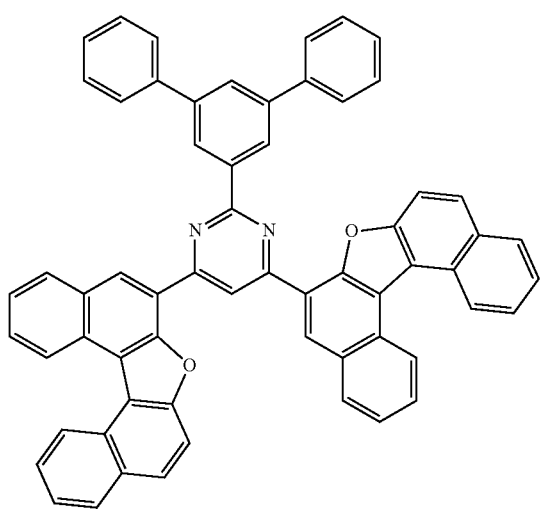
32
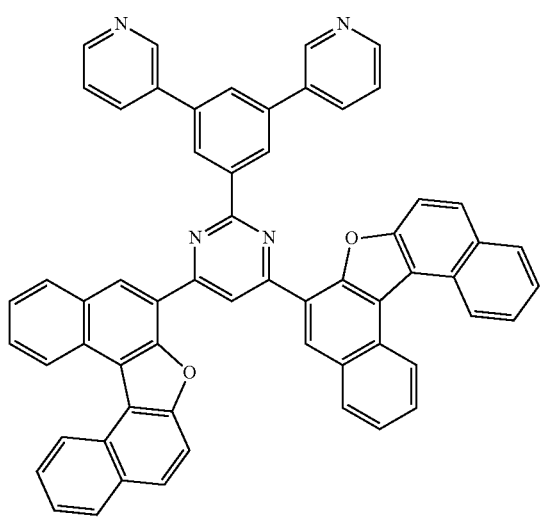
124
-continued
33
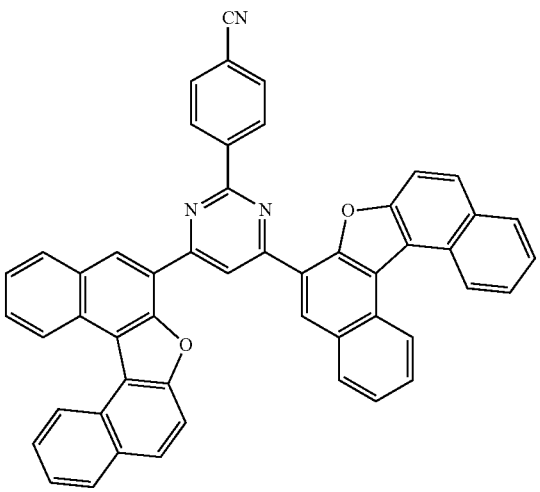
34
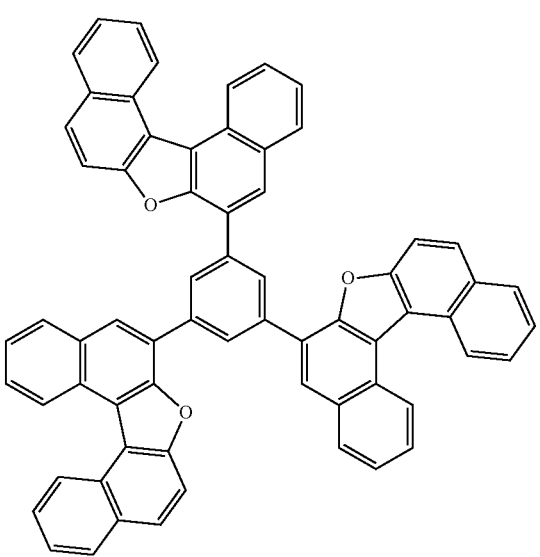
35

36
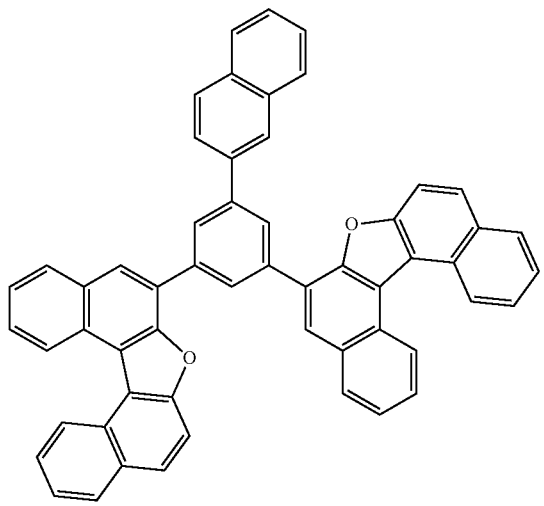
37
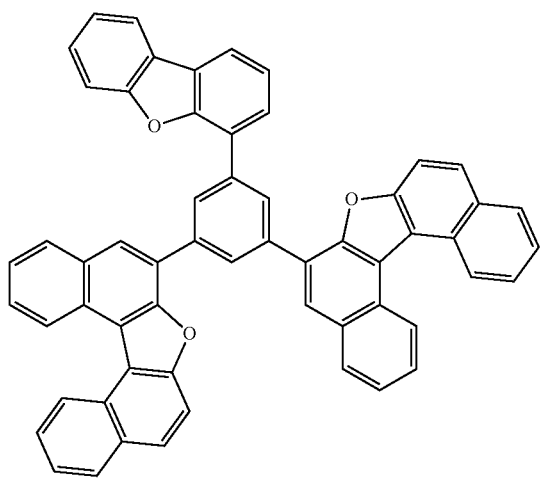
38
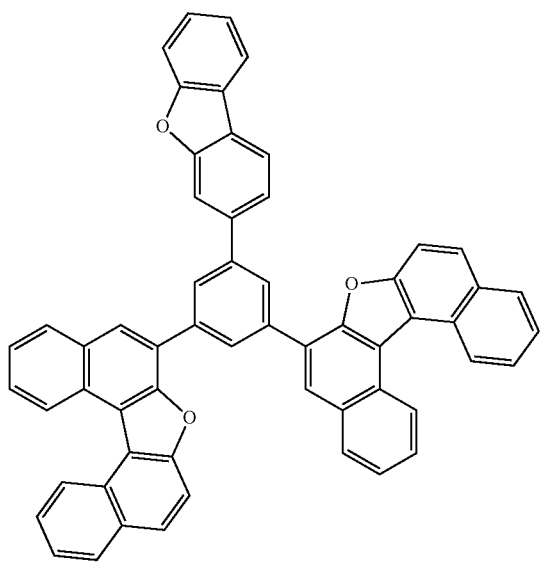
39
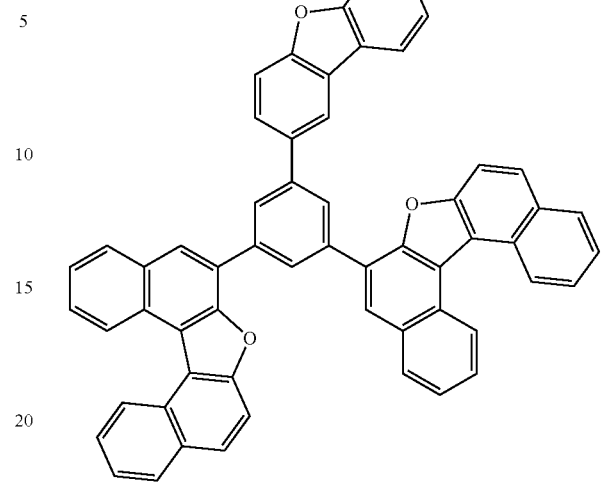
40
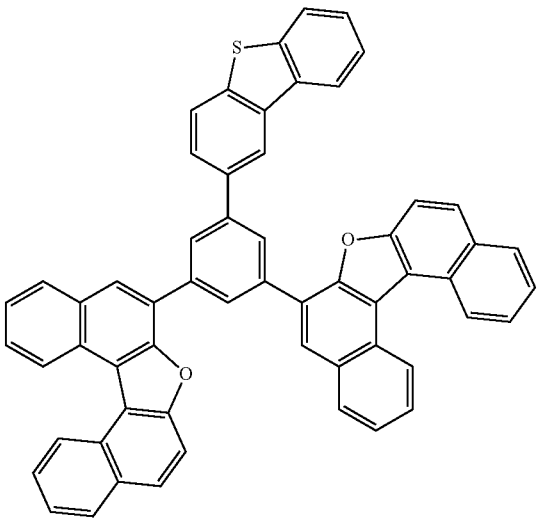
41

42
-continued
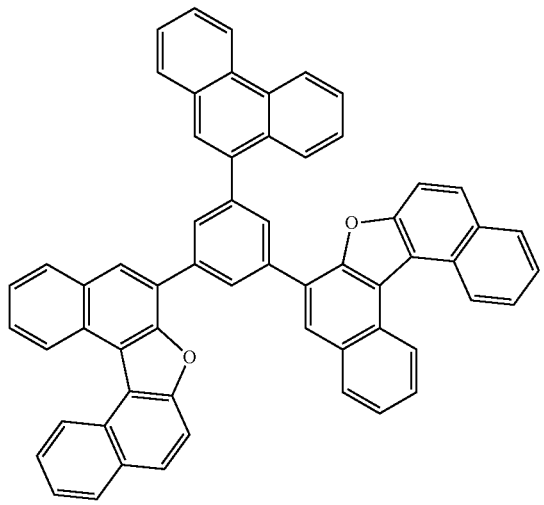
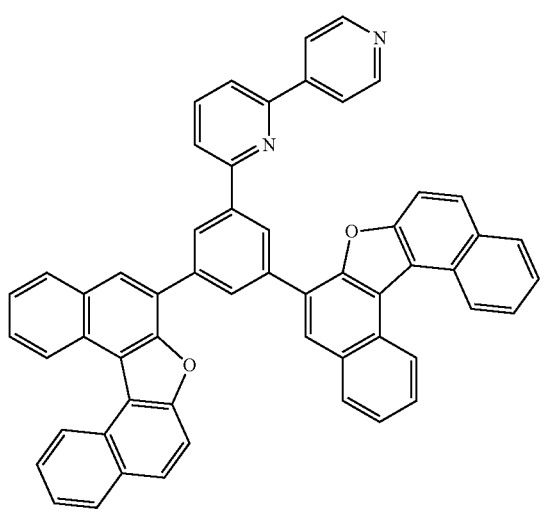
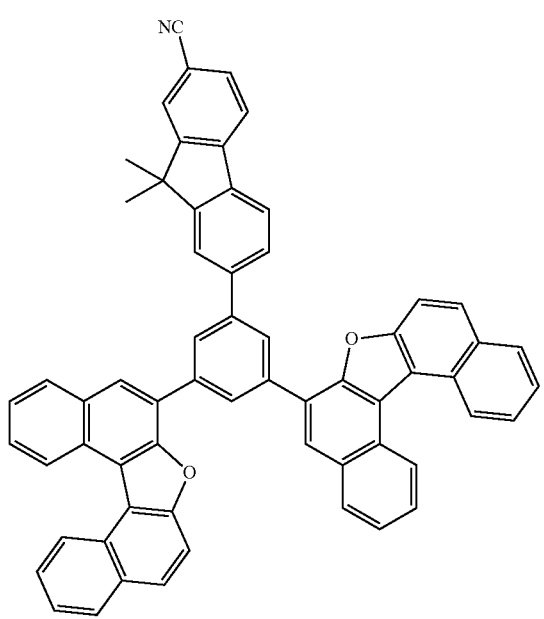
43
44
45
-continued
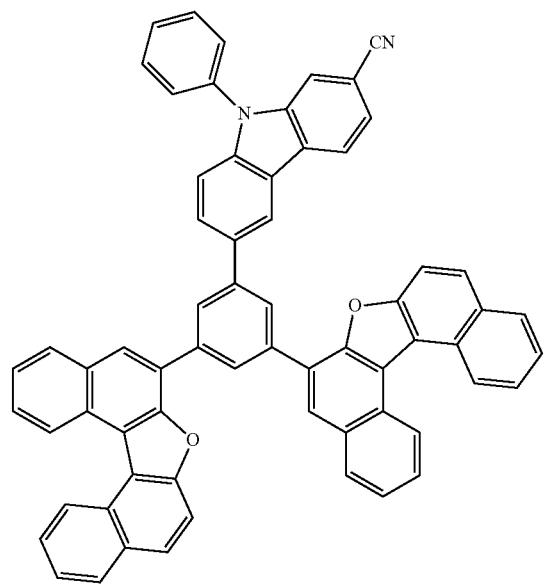
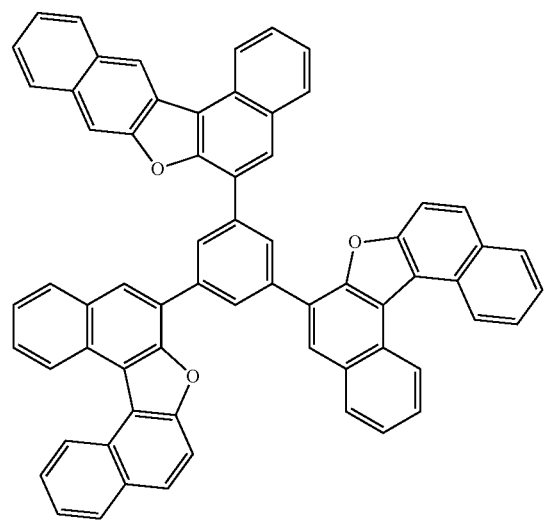
45
46

47
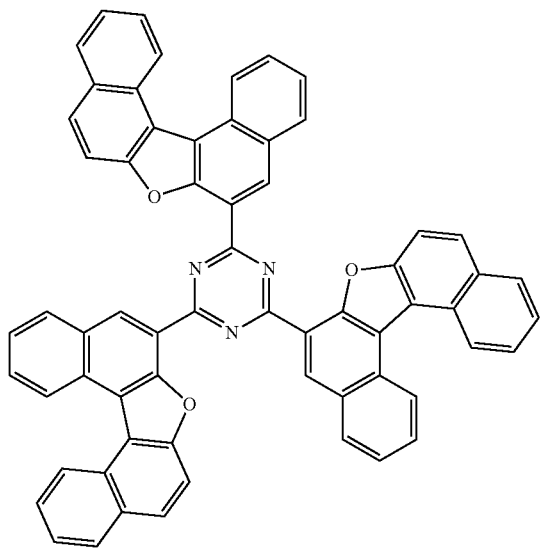
48
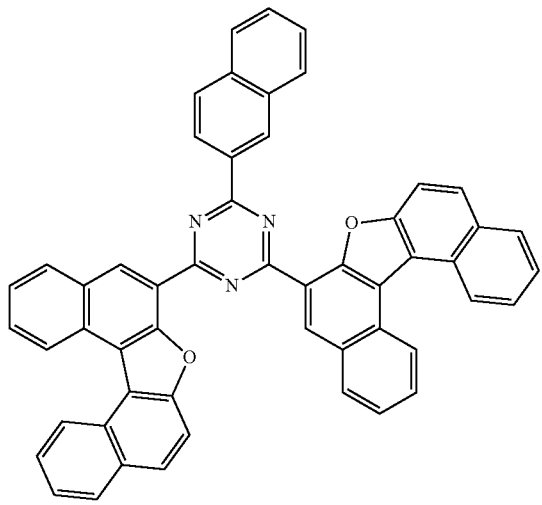
49
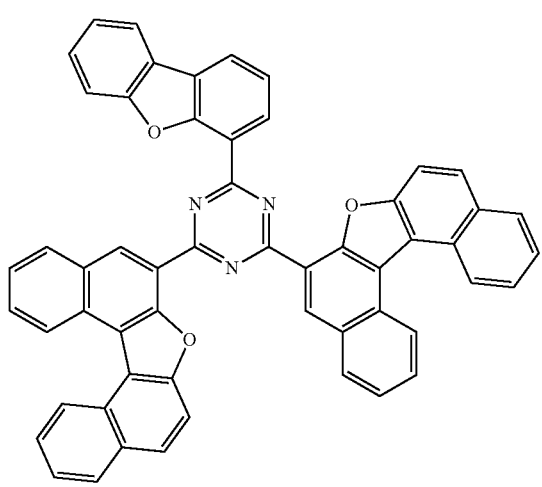
50
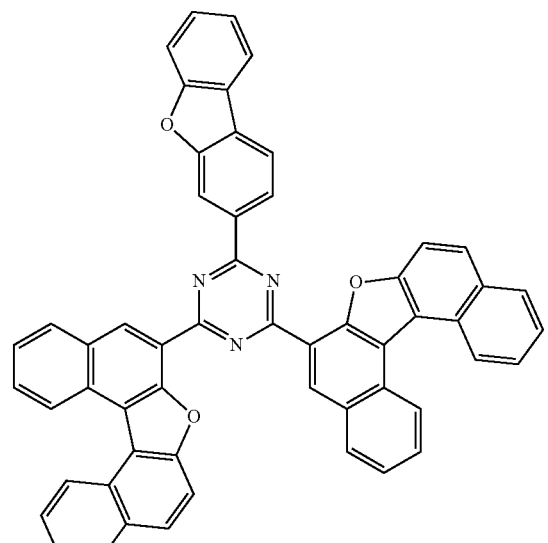
51
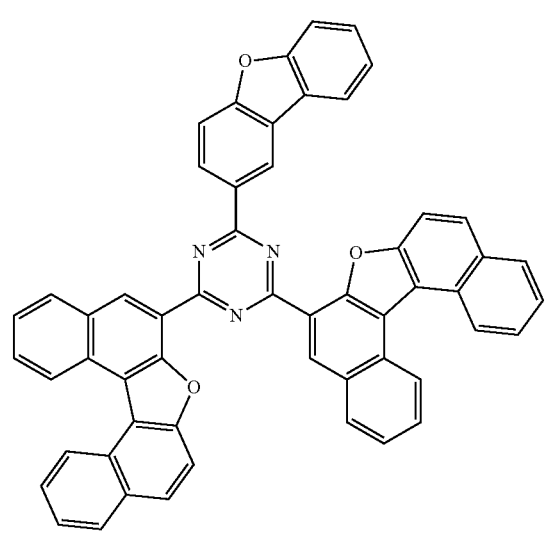
52
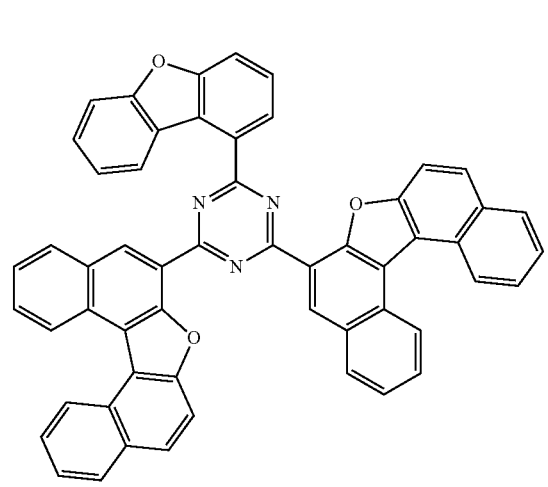

131
-continued
53
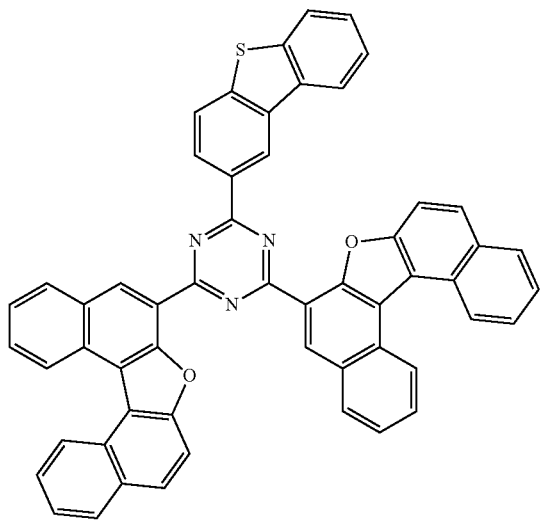
54
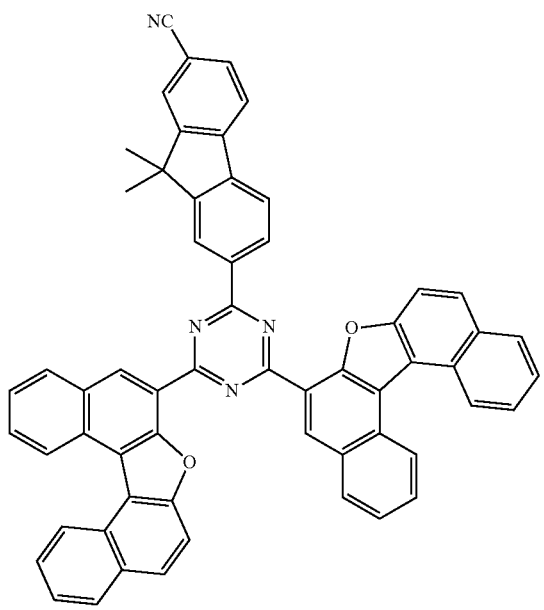
132
-continued
55
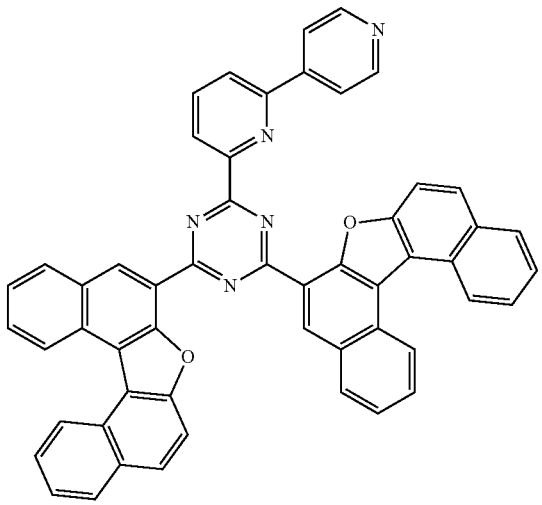
56
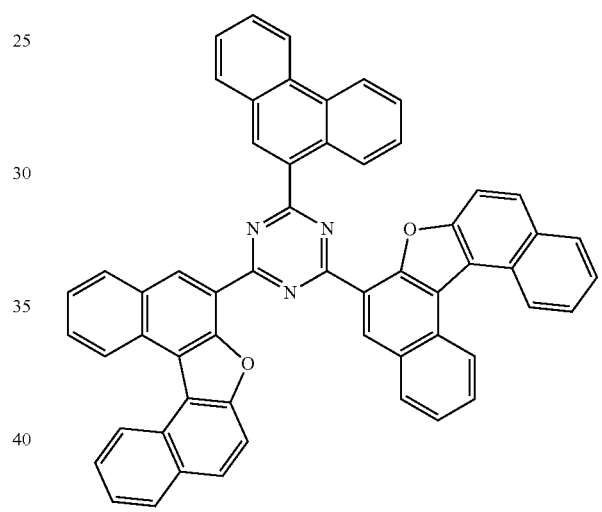
57
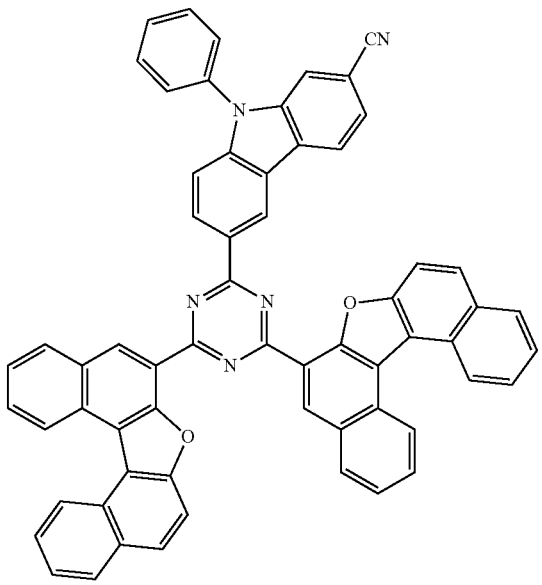

58
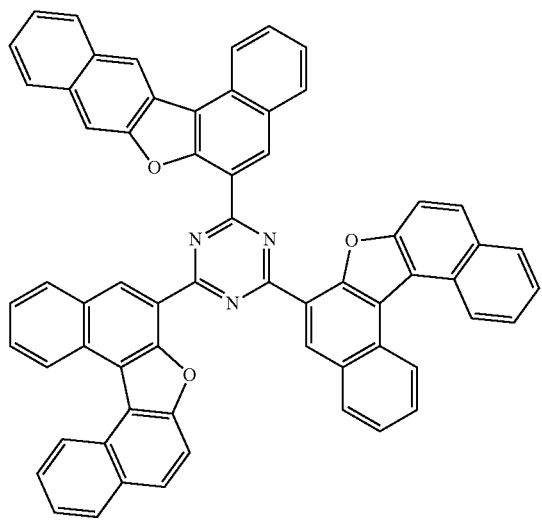
59
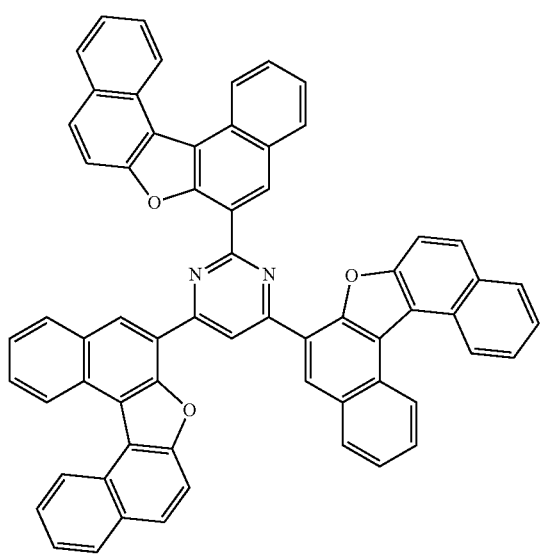
60
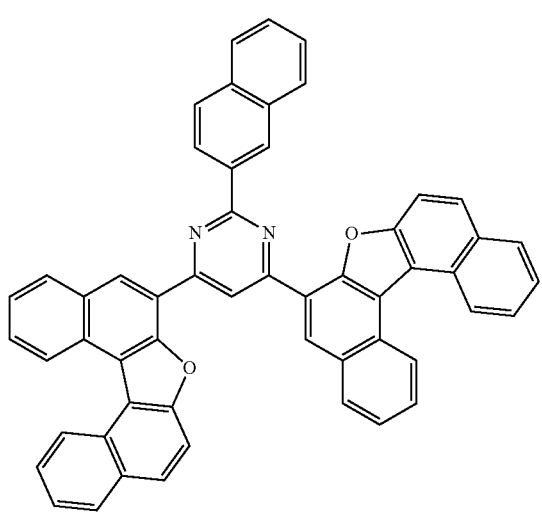
61
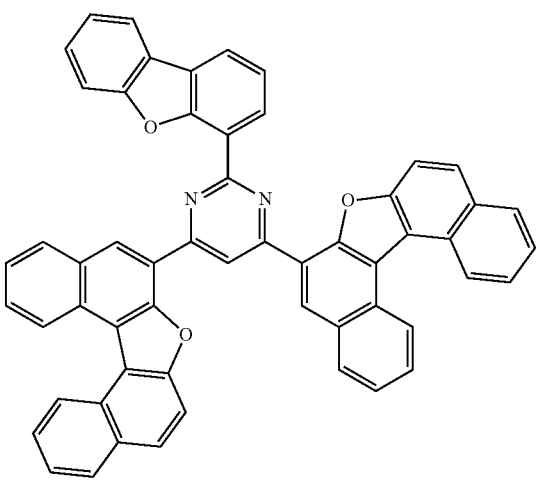
62
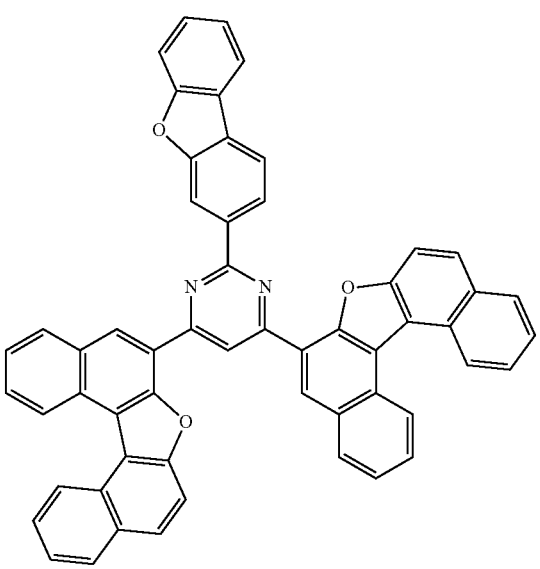
63
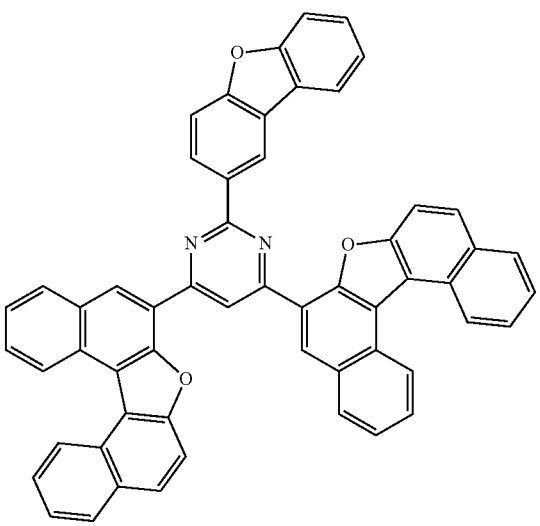

64
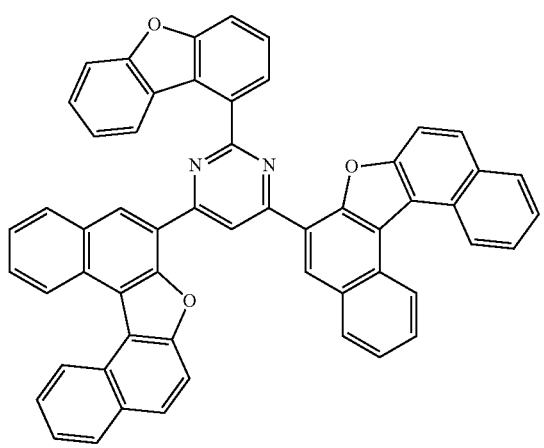
65
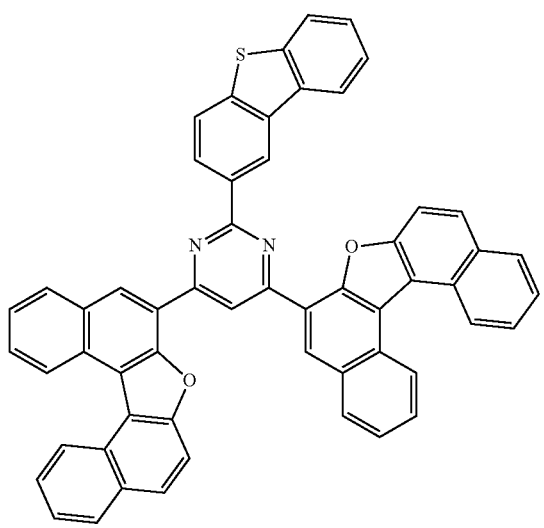
66
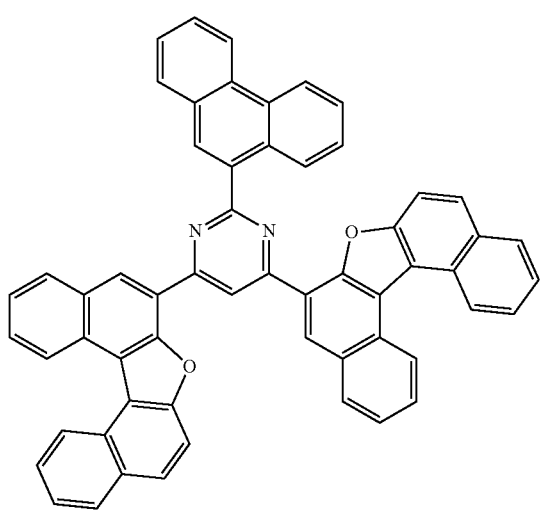
67
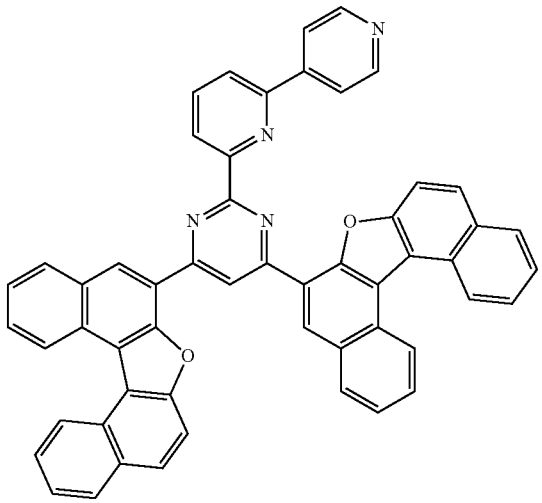
68
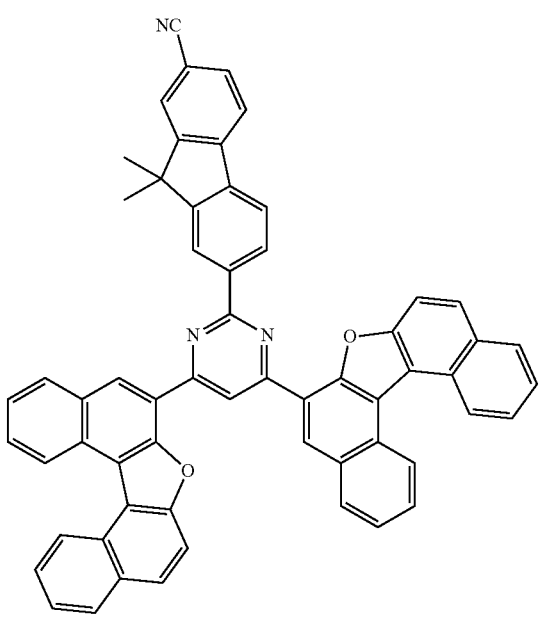

-continued

69

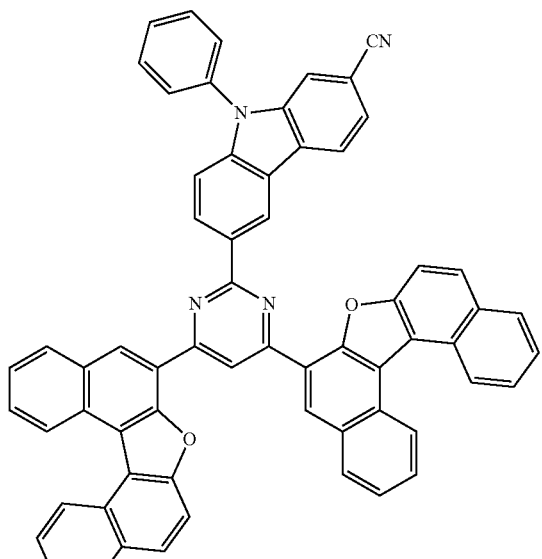

70

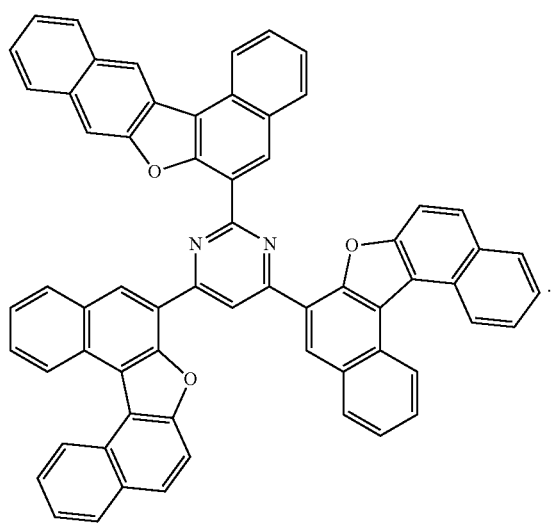

10. An organic light-emitting device comprising:
a first electrode;
a second electrode facing the first electrode; and
an organic layer between the first electrode and the second electrode, the organic layer comprising an emission layer,
wherein the organic layer comprises the compound of claim 1.

11. The organic light-emitting device of claim 10, wherein
the first electrode is an anode,
the second electrode is a cathode,
the organic layer further comprises:
i) a hole transport region between the first electrode and the emission layer, the hole transport region comprising at least one selected from a hole injection layer, a hole transport layer, and an electron blocking layer, and
ii) an electron transport region between the emission layer and the second electrode, the electron transport region comprising an electron transport layer and at least one selected from a hole blocking layer and an electron injection layer.

12. The organic light-emitting device of claim 11, wherein the electron transport region comprises the compound.

13. The organic light-emitting device of claim 11, wherein the electron transport layer comprises the compound.

14. The organic light-emitting device of claim 11, wherein the hole transport region comprises a charge-generating material.

15. The organic light-emitting device of claim 14, wherein the charge-generating material comprises a p-dopant.

16. The organic light-emitting device of claim 15, wherein the p-dopant is selected from a quinone derivative, a metal oxide, and a cyano-containing compound.

17. The organic light-emitting device of claim 11, wherein the electron transport region comprises a metal complex.

18. The organic light-emitting device of claim 11, wherein the electron transport region comprises Compound ET-D1 and/or Compound ET-D2:

ET-D1

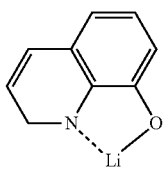

ET-D2

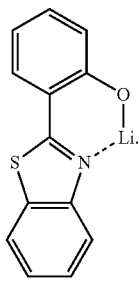

19. A display apparatus comprising:
a thin film transistor, the thin film transistor comprising a source electrode and a drain electrode; and
the organic light-emitting device of claim 10,
wherein the first electrode of the organic light-emitting device is electrically coupled to the source electrode or the drain electrode of the thin film transistor.

* * * * *